United States Patent
Ohashi et al.

(10) Patent No.: US 11,721,436 B2
(45) Date of Patent: Aug. 8, 2023

(54) CARE SCHEDULE PROPOSAL DEVICE

(71) Applicant: Kao Corporation, Tokyo (JP)

(72) Inventors: Kazuo Ohashi, Koshigaya (JP); Hideko Goshowaki, Shibuya-ku (JP)

(73) Assignee: Kao Corporation, Tokyo (JP)

(*) Notice: Subject to any disclaimer, the term of this patent is extended or adjusted under 35 U.S.C. 154(b) by 723 days.

(21) Appl. No.: 16/617,151

(22) PCT Filed: May 29, 2018

(86) PCT No.: PCT/JP2018/020615
§ 371 (c)(1),
(2) Date: Nov. 26, 2019

(87) PCT Pub. No.: WO2018/221535
PCT Pub. Date: Dec. 6, 2018

(65) Prior Publication Data
US 2021/0151177 A1    May 20, 2021

(30) Foreign Application Priority Data
May 30, 2017  (JP) .............. JP2017-107253

(51) Int. Cl.
*A61F 13/49*   (2006.01)
*G16H 40/67*   (2018.01)
(Continued)

(52) U.S. Cl.
CPC ............. *G16H 40/67* (2018.01); *A61B 5/208* (2013.01); *A61F 13/42* (2013.01); *G16H 20/00* (2018.01);
(Continued)

(58) Field of Classification Search
CPC ........ G16H 40/67; G16H 20/00; A61B 5/208; A61F 13/42; A61F 13/49; A61F 2013/15471; A61F 2013/424
See application file for complete search history.

(56) References Cited

U.S. PATENT DOCUMENTS 4,965,554 A * 10/1990 Darling ................ E04D 13/006
                                                73/40
5,137,033 A *  8/1992 Norton ...................... A61F 5/48
                                              340/573.5
(Continued)

FOREIGN PATENT DOCUMENTS

CN        1226855 A     8/1999
CN      101217923 A     7/2008
(Continued)

OTHER PUBLICATIONS

Margaret Heale, Continence Assessment, Types of Incontinence, and Care Planning (Year: 2019).*
(Continued)

*Primary Examiner* — Quang Pham
(74) *Attorney, Agent, or Firm* — Obion, McClelland, Maier & Neustadt, L.L.P.

(57) ABSTRACT

A system includes a urination data storage unit, an absorbent article information storage unit, a changeable time storage unit, and a changing schedule proposal unit. The changing schedule proposal unit includes a changing schedule computation unit and a changing schedule outputting unit. The changing schedule computation unit finds, on the basis of urination amount data and urination time instant data stored in the urination data storage unit, a total urination amount within a predetermined time period selected from changeable time instants stored in the changeable time storage unit, and performs, by comparing the total urination amount that has been found and the urine absorption capacity of an
(Continued)

US 11,721,436 B2

Page 2 absorbent article, computation for finding the absorbent article or the predetermined time period such that the urine absorption capacity does not fall below the total urination amount.

12 Claims, 18 Drawing Sheets

(51) Int. Cl.
*G16H 20/00* (2018.01)
*A61B 5/20* (2006.01)
*A61F 13/42* (2006.01)
*A61F 13/15* (2006.01)

(52) U.S. Cl.
CPC ..... *A61F 13/49* (2013.01); *A61F 2013/15471* (2013.01); *A61F 2013/424* (2013.01)

(56) References Cited

U.S. PATENT DOCUMENTS

| | | | | |
|---|---|---|---|---|
| 5,463,377 | A * | 10/1995 | Kronberg | G08B 21/20 340/592 |
| 5,649,914 | A * | 7/1997 | Glaug | A61F 13/42 607/114 |
| 5,903,222 | A * | 5/1999 | Kawarizadeh | G01N 27/223 340/573.5 |
| 6,093,869 | A | 7/2000 | Roe et al. | |
| 6,348,640 | B1 * | 2/2002 | Navot | A61F 13/42 604/385.18 |
| 6,559,772 | B2 * | 5/2003 | Zand | A61F 13/42 604/361 |
| 6,583,722 | B2 * | 6/2003 | Jeutter | A61F 13/42 340/941 |
| 6,774,800 | B2 * | 8/2004 | Friedman | A61B 5/6804 340/573.5 |
| 7,141,715 | B2 * | 11/2006 | Shapira | A61F 13/84 340/573.6 |
| 7,250,547 | B1 * | 7/2007 | Hofmeister | G01N 27/121 340/573.5 |
| 7,294,105 | B1 * | 11/2007 | Islam | A61B 5/0006 128/903 |
| 7,522,477 | B1 * | 4/2009 | Sheldon | G04G 11/00 368/10 |
| 7,700,821 | B2 * | 4/2010 | Ales, III | A61F 13/42 604/361 |
| 8,191,187 | B2 * | 6/2012 | Brykalski | A47C 21/044 607/104 |
| 8,421,636 | B2 * | 4/2013 | Collette | A61F 13/42 340/573.5 |
| 8,428,605 | B2 * | 4/2013 | Pedersen | H04W 72/04 455/450 |
| 8,454,550 | B2 * | 6/2013 | Koenig | A61M 1/3653 600/362 |
| 8,471,715 | B2 * | 6/2013 | Solazzo | A61F 13/42 340/573.5 |
| 8,682,952 | B2 * | 3/2014 | Kutzik | G16H 40/67 709/200 |
| 8,878,676 | B2 * | 11/2014 | Koblasz | G16H 40/67 342/450 |
| 8,914,923 | B2 * | 12/2014 | Smith | A47C 27/008 5/699 |
| 8,989,837 | B2 * | 3/2015 | Weinstein | A61B 8/4254 600/407 |
| 9,165,449 | B2 * | 10/2015 | Ribble | A61B 5/746 |
| 9,322,797 | B1 * | 4/2016 | Lastinger | G01N 27/12 |
| 9,366,644 | B1 * | 6/2016 | Lastinger | G01N 27/07 |
| 9,506,886 | B1 * | 11/2016 | Woodbury | G01N 27/12 |
| 9,517,012 | B2 * | 12/2016 | Lane | G16H 40/63 |
| 9,649,230 | B1 * | 5/2017 | Li | A61F 13/42 |
| 9,675,496 | B1 * | 6/2017 | Alkhamis | A61F 13/42 |
| 9,681,996 | B2 * | 6/2017 | Prioleau | A61F 13/42 |
| 10,022,277 | B2 * | 7/2018 | Heil | A61F 13/42 |
| D826,740 | S * | 8/2018 | Stevens | D24/126 |
| 10,134,489 | B2 * | 11/2018 | Lai | G16H 40/63 |
| 10,159,607 | B2 * | 12/2018 | Monson | G06K 7/10356 |
| 10,349,881 | B1 * | 7/2019 | Monson | G06K 7/10366 |
| 10,458,876 | B1 * | 10/2019 | Billman | G01M 3/40 |
| 10,470,689 | B2 * | 11/2019 | Kilcran | A61B 5/002 |
| 10,481,105 | B2 * | 11/2019 | Advani | G01N 22/00 |
| 10,489,661 | B1 * | 11/2019 | Rush | G06F 18/25 |
| 10,527,487 | B2 * | 1/2020 | Pretorius | H04N 5/04 |
| 10,624,795 | B2 * | 4/2020 | Christiansen | A61F 13/42 |
| 10,624,804 | B2 * | 4/2020 | Williams | A61G 7/02 |
| 10,653,567 | B2 * | 5/2020 | Weidman | G06K 7/10366 |
| 10,716,715 | B2 * | 7/2020 | Severns | G06K 7/10158 |
| 10,945,892 | B2 * | 3/2021 | Severns | G01N 27/048 |
| 10,950,340 | B2 * | 3/2021 | Ranta | G08B 21/20 |
| 10,970,991 | B1 * | 4/2021 | Alovert | G08B 21/20 |
| 11,039,530 | B2 * | 6/2021 | Hanazawa | H05K 1/0283 |
| 11,083,636 | B2 * | 8/2021 | Potter | A61F 13/42 |
| 11,147,490 | B2 * | 10/2021 | Stevens | A61B 5/202 |
| 11,173,073 | B2 * | 11/2021 | MacNaughton | G08B 21/20 |
| 11,173,074 | B2 * | 11/2021 | Love | A61F 13/0209 |
| 11,197,785 | B2 * | 12/2021 | Mehta | A61F 13/42 |
| 11,229,557 | B2 * | 1/2022 | Kurt | A61F 13/51456 |
| 11,278,457 | B2 * | 3/2022 | Benz | A61F 13/42 |
| 11,311,436 | B2 * | 4/2022 | Corbin | A61F 13/42 |
| 11,457,848 | B2 * | 10/2022 | Harmeyer | A61B 5/369 |
| 2002/0021220 | A1 * | 2/2002 | Dreyer | G09B 19/0076 340/573.1 |
| 2003/0063135 | A1 * | 4/2003 | Liu | G16H 20/60 715/864 |
| 2003/0114807 | A1 * | 6/2003 | Underhill | A61F 13/536 604/361 |
| 2003/0137425 | A1 * | 7/2003 | Gabriel | G16H 40/67 340/573.5 |
| 2004/0122744 | A1 * | 6/2004 | Heki | A61F 13/84 705/3 |
| 2004/0153443 | A1 * | 8/2004 | McDonald | G16H 50/70 |
| 2004/0220538 | A1 * | 11/2004 | Panopoulos | A61F 13/42 604/361 |
| 2005/0033250 | A1 * | 2/2005 | Collette | A61F 13/42 604/361 |
| 2005/0156744 | A1 * | 7/2005 | Pires | A61F 13/42 340/573.5 |
| 2005/0225335 | A1 * | 10/2005 | Filipkowski | G01N 27/048 324/696 |
| 2007/0035405 | A1 | 2/2007 | Wada et al. | |
| 2007/0083174 | A1 * | 4/2007 | Ales, III | A61F 13/42 604/361 |
| 2007/0252714 | A1 * | 11/2007 | Rondoni | A61B 5/0002 340/573.5 |
| 2007/0270774 | A1 * | 11/2007 | Bergman | G16H 40/60 604/361 |
| 2008/0036614 | A1 * | 2/2008 | Gabriel | A61F 13/42 340/604 |
| 2008/0243099 | A1 * | 10/2008 | Tippey | A61F 13/15699 604/361 |
| 2008/0297325 | A1 | 12/2008 | Torstensson et al. | |
| 2009/0315720 | A1 * | 12/2009 | Clement | H01Q 1/2225 340/573.5 |
| 2010/0176827 | A1 * | 7/2010 | Yamazaki | G01R 27/08 324/699 |
| 2011/0095884 | A1 * | 4/2011 | Xu | A61F 13/42 340/539.11 |
| 2011/0137274 | A1 * | 6/2011 | Klofta | A61L 15/56 604/361 |
| 2011/0172625 | A1 * | 7/2011 | Wada | A61F 13/42 604/385.01 |
| 2011/0263952 | A1 * | 10/2011 | Bergman | A61F 13/42 604/361 |
| 2011/0319845 | A1 * | 12/2011 | Kuo | A61F 13/42 604/361 |
| 2012/0157947 | A1 * | 6/2012 | Nhan | A61F 13/42 604/361 |
| 2012/0245542 | A1 | 9/2012 | Suzuki et al. | |
| 2013/0018231 | A1 | 1/2013 | Hong et al. | |
| 2013/0036802 | A1 | 2/2013 | Johnson et al. | |

(56) References Cited

U.S. PATENT DOCUMENTS

| | | | |
|---|---|---|---|
| 2013/0053754 A1* | 2/2013 | Heppe | A61M 1/3653 604/6.16 |
| 2013/0076509 A1* | 3/2013 | Ahn | A61F 13/42 340/539.12 |
| 2013/0109929 A1* | 5/2013 | Menzel | A61B 5/6824 600/301 |
| 2013/0110061 A1* | 5/2013 | Abraham | A61F 13/42 604/342 |
| 2013/0110063 A1* | 5/2013 | Abraham | G16H 40/67 604/361 |
| 2013/0110064 A1* | 5/2013 | Richardson | A61F 13/42 340/573.5 |
| 2013/0123726 A1* | 5/2013 | Yu | H01Q 1/273 235/492 |
| 2013/0254141 A1* | 9/2013 | Barda | A61F 13/42 706/46 |
| 2013/0303867 A1 | 11/2013 | Elfstrom et al. | |
| 2013/0307570 A1* | 11/2013 | Bosaeus | A61F 13/42 324/694 |
| 2014/0039351 A1* | 2/2014 | Mix | A61G 7/057 600/587 |
| 2014/0148772 A1* | 5/2014 | Hu | A61F 13/42 604/385.01 |
| 2014/0182051 A1 | 7/2014 | Tanimoto et al. | |
| 2014/0200538 A1* | 7/2014 | Euliano | A61F 13/42 604/361 |
| 2014/0292520 A1 | 10/2014 | Carney et al. | |
| 2014/0327546 A1* | 11/2014 | Carney | A61F 13/42 340/573.5 |
| 2014/0333442 A1 | 11/2014 | Carney | |
| 2014/0358099 A1* | 12/2014 | Durgin | A61F 13/42 340/573.5 |
| 2015/0032668 A1* | 1/2015 | Sazuka | G06N 5/02 706/11 |
| 2015/0080819 A1 | 3/2015 | Charna et al. | |
| 2015/0148762 A1 | 5/2015 | Johnson et al. | |
| 2015/0165313 A1* | 6/2015 | Thompson | A61B 5/02055 463/7 |
| 2015/0173968 A1* | 6/2015 | Joseph | A61F 13/532 604/361 |
| 2015/0206151 A1* | 7/2015 | Carney | A61B 5/0002 705/304 |
| 2015/0294549 A1* | 10/2015 | Ribble | A61G 7/0524 340/573.5 |
| 2015/0319486 A1* | 11/2015 | Wang | H04M 1/72412 725/62 |
| 2016/0078176 A1* | 3/2016 | Ranta | G16H 10/60 705/2 |
| 2016/0120473 A1* | 5/2016 | Linton | A61B 5/6808 600/362 |
| 2016/0174892 A1* | 6/2016 | Benson | A61B 5/01 600/300 |
| 2016/0284036 A1* | 9/2016 | Sampson | G16H 10/20 |
| 2016/0310329 A1* | 10/2016 | Patel | A61B 5/1118 |
| 2017/0098044 A1* | 4/2017 | Lai | G06K 19/07745 |
| 2017/0112681 A1* | 4/2017 | Mancini | A61F 13/42 |
| 2017/0119308 A1* | 5/2017 | Fuh | A61B 5/7275 |
| 2017/0156594 A1* | 6/2017 | Stivoric | A61B 5/0008 |
| 2017/0236398 A1* | 8/2017 | Eddy | A61B 5/202 340/573.5 |
| 2017/0325345 A1* | 11/2017 | Teng | A61F 13/42 |
| 2018/0014981 A1* | 1/2018 | Schiavenato | A61F 13/505 |
| 2018/0279910 A1* | 10/2018 | Jensen | G16Z 99/00 |
| 2018/0333306 A1* | 11/2018 | Ahong | A61F 13/42 |
| 2019/0110938 A1* | 4/2019 | Chiu | G01N 27/121 |
| 2019/0307405 A1* | 10/2019 | Terry | G16H 10/60 |
| 2020/0175836 A1* | 6/2020 | Rogers | G08B 5/36 |
| 2020/0330021 A1* | 10/2020 | Samadani | A61B 5/053 |
| 2021/0093244 A1* | 4/2021 | Monson | G16H 40/20 |
| 2021/0316145 A1* | 10/2021 | Offutt | A61B 5/202 |

FOREIGN PATENT DOCUMENTS

| | | |
|---|---|---|
| CN | 101340876 A | 1/2009 |
| CN | 102054334 A | 5/2011 |
| CN | 202650203 U | 1/2013 |
| CN | 104224448 A | 12/2014 |
| EP | 1 219 273 A2 | 7/2002 |
| EP | 2 091489 A1 | 8/2009 |
| JP | 2002-73805 A | 3/2002 |
| JP | 3666479 B2 | 6/2005 |
| JP | 4101432 B2 | 6/2008 |
| JP | 2012-105839 A | 6/2012 |
| JP | 2012-152249 A | 8/2012 |
| JP | 2013-39158 A | 2/2013 |
| JP | 2015-506192 A | 3/2015 |
| JP | 2015-119784 A | 7/2015 |
| JP | 2015-534153 A | 11/2015 |
| JP | 2016-32519 A | 3/2016 |
| JP | 2016-32520 A | 3/2016 |
| JP | 2016-195792 A | 11/2016 |
| JP | 2017-189340 A | 10/2017 |
| JP | 2017-189348 A | 10/2017 |
| JP | 2017-207317 A | 11/2017 |
| TW | 410155 B | 11/2000 |
| TW | 201130468 A1 | 9/2011 |
| TW | 201302174 A1 | 1/2013 |
| TW | 201312104 A1 | 3/2013 |
| TW | M515376 U | 1/2016 |
| WO | WO 97/42613 A2 | 11/1997 |
| WO | WO 98/01227 A1 | 1/1998 |
| WO | WO 02/101679 A1 | 12/2002 |
| WO | WO 2007/128038 A1 | 11/2007 |
| WO | WO-2007128038 A1 * | 11/2007 ............. A61F 13/42 |
| WO | WO 2008/075227 A1 | 6/2008 |
| WO | WO 2009/001229 A2 | 12/2008 |
| WO | WO 2009/027871 A1 | 3/2009 |
| WO | WO 2010/001274 A2 | 1/2010 |
| WO | WO 2011/156862 A1 | 12/2011 |
| WO | WO 2013/022742 A1 | 2/2013 |
| WO | WO 2013/095230 A1 | 6/2013 |
| WO | WO 2013/095231 A1 | 6/2013 |
| WO | WO 2014/035302 A1 | 3/2014 |
| WO | WO 2014/064680 A1 | 5/2014 |
| WO | WO 2014/178763 A1 | 11/2014 |

OTHER PUBLICATIONS

Omli et al., Pad per day usage, urinary incontinence and urinary tract infections in nursing home residents (Year: 2010).*

Rice et al., Rationale and Design of a Novel Method to Assess the Usability of Body-Worn Absorbent Incontinence Care Products by Caregivers (Year: 2018).*

McDaniel, Urinary Incontinence in Older Adults Takes Collaborative Nursing Efforts to Improve (Year: 2020).*

Santini et al., The impact of the absorbent products distribution system on family caregivers of older people with incontinence in Italy perception of the support received (Year: 2019).*

International Search Report dated Aug. 21, 2018 in PCT/JP2018/020615 filed on May 29, 2018, 1 page.

International Search Report dated Aug. 21, 2018 in PCT/JP2018/020606 filed on May 29, 2018, 1 page.

Extended European Search Report dated Feb. 2, 2021 in corresponding European Patent Application No. 18809794.3, 5 pages.

* cited by examiner

Fig. 4
(a)
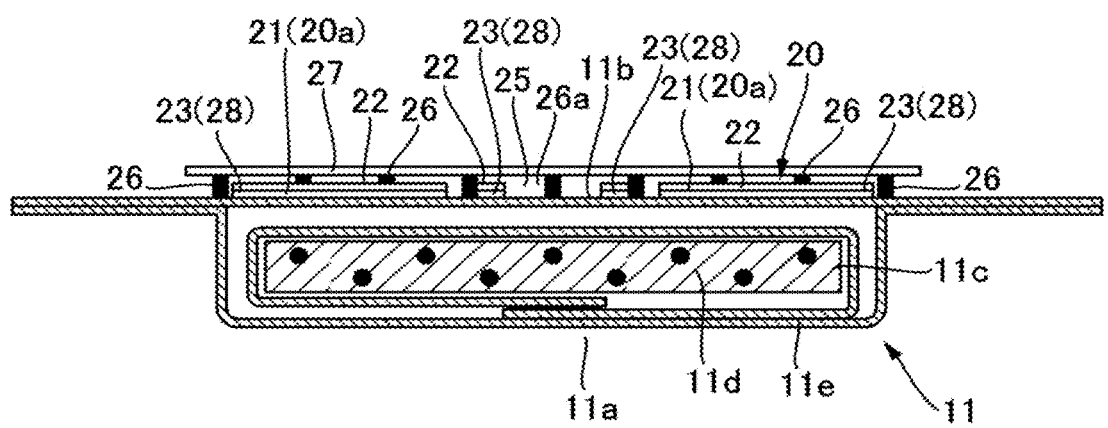
(b)
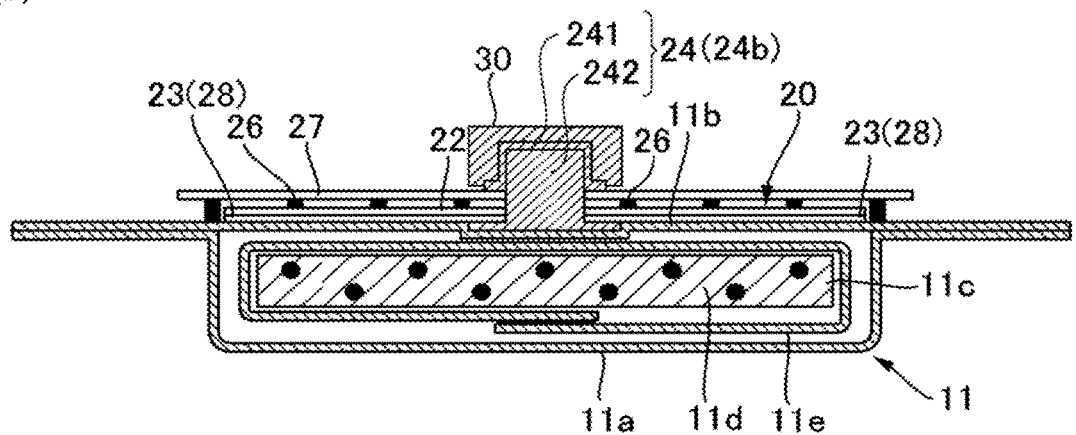

| Type of diaper | 9:00~13:00 | 13:00~16:00 | 16:00~21:00 | 21:00~9:00 |
|---|---|---|---|---|
| | Absorbent article B<br>Absorption capacity<br>600mL | Absorbent article A<br>Absorption capacity<br>300mL | Absorbent article C<br>Absorption capacity<br>900mL | Absorbent article E<br>Absorption capacity<br>1500mL |

(b)

| Type of diaper | 9:00~13:00 | 13:00~16:00 | 16:00~21:00 | 21:00~9:00 |
|---|---|---|---|---|
| | Medium-small | Small | Medium | Large |

| Type of diaper | Small | Medium-small | Medium | Medium-large | Large | Extra large |
|---|---|---|---|---|---|---|

CARE SCHEDULE PROPOSAL DEVICE

CROSS REFERENCE TO RELATED APPLICATIONS

This application is a national phase application of PCT/JP2018/020615, filed May 29, 2018, which claims priority to Japanese Patent Application No. 2017-107253, filed May 30, 2017, wherein the entire content and disclosure of each of the foregoing applications is incorporated by reference into the present application.

TECHNICAL FIELD

The present invention relates to a care schedule proposal device, a care schedule proposal method, and a care schedule proposal system.

BACKGROUND ART

In caring for senior care-receivers or infants that use absorbent articles such as diapers, it is desirable to reduce the burden on caregivers or child-care specialists who perform the tasks of changing absorbent articles. To meet such a demand, there have been proposed techniques for providing absorbent articles, such as diapers, with functions for detecting urination etc. For example, Patent Literature 1 discloses a wetness monitoring system wherein: a sensor for detecting urination is attached to an absorbent article such as a diaper; the occurrence and the number of times of urination are monitored; and an alarm is sounded in accordance with, for example, the number of times of urination.

Patent Literature 2 discloses a moisture monitoring system including an absorbent article to which a sensor is attached, and a processor for processing a sensor signal and deriving a urination pattern. The Literature describes an embodiment wherein, by using the system, wetness of an absorbent article is monitored for three to five days, to create an excretion care plan for the wearer of the absorbent article.

Patent Literature 3 discloses a method for monitoring use of an absorbent article, and providing a caregiver with recommendation to switch the currently worn absorbent article to another absorbent article having a larger absorption capacity than the currently worn product. The Literature describes that the method involves a step for evaluating the movement of the wearer and predicting the urination amount.

Patent Literature 4 discloses a method for providing recommendations or advice to a caregiver to switch to a different type of absorbent article when performing toilet training in accordance with the growth of a child, the method employing a wetness detection system provided to an absorbent article, and a void volume indicator. The Literature describes that, in the method, for example, increases in void volume over time and/or increases in the time interval between voids are detected, and such information is provided as feedback to the caregiver.

CITATION LIST

Patent Literature

Patent Literature 1: International Publication WO2009027871A1
Patent Literature 2: International Publication WO2007128038A1
Patent Literature 3: International Publication WO2013095230A1
Patent Literature 4: International Publication WO2010001274A2

SUMMARY OF INVENTION

The present invention is a care schedule proposal device including: a urination data storage unit that stores, together with urination time instant data, urination amount data of a wearer as acquired from a urine absorption amount of an absorbent article that absorbs urine; an absorbent article information storage unit that stores article information including a urine absorption capacity of the absorbent article; a changeable time storage unit that stores a changeable time instant or a changeable time period that can serve as a candidate for a changing time instant for changing the absorbent article; and a changing schedule proposal unit that proposes a changing schedule for changing the absorbent article. The changing schedule proposal unit includes a changing schedule computation unit and a changing schedule outputting unit. The changing schedule computation unit finds, on the basis of the urination amount data and the urination time instant data stored in the urination data storage unit, a total urination amount within a predetermined time period defined by a wearing-start candidate time instant and a wearing-end candidate time instant which are selected from the changeable time instant or the changeable time period stored in the changeable time storage unit. The changing schedule computation unit performs, by comparing the total urination amount that has been found and the urine absorption capacity of the absorbent article stored in the absorbent article information storage unit, computation for finding at least either the absorbent article or the predetermined time period in a manner that the urine absorption capacity of the absorbent article does not fall below the total urination amount. The changing schedule outputting unit presents schedule information including at least either the absorbent article or the predetermined time period found by the changing schedule computation unit.

The present invention is also a care schedule proposal system including: the aforementioned care schedule proposal device; a urination sensor that measures spreading of urine by employing impedance; and a data acquisition unit that acquires data from the urination sensor.

The present invention is also a care schedule proposal method for proposing at least either an absorbent article to be worn or a changing time instant for changing an absorbent article, by using urination data—including urination amount data and urination time instant data corresponding to the urination amount data—and urine absorption capacity data including a urine absorption capacity of an absorbent article to be used, in circumstances where there are limitations in terms of changeable time instants or changeable time periods that can serve as the changing time instant for changing the absorbent article. The care schedule proposal method involves: a total urination amount computation step of temporarily determining a wearing-start time instant, which is one changing time instant, and a wearing-end time instant, which is a next changing time instant, from the changeable time instants or the changeable time periods, and finding, from the urination data, a total urination amount in a predetermined time period defined by the temporarily determined one changing time instant and next changing time instant; and a schedule computation step of comparing the total urination amount that has been found and the urine absorption capacity of the absorbent article, and finding at least either the predetermined time period or the absorbent article by which the urine absorption capacity does not fall below the total urination amount.

BRIEF DESCRIPTION OF DRAWINGS

FIG. 4 illustrates the urine absorption pad with the urination sensor and the cover sheet attached thereto, wherein FIG. 4(a) is an enlarged schematic cross-sectional view taken along line A-A of FIG. 3, and FIG. 4(b) is an enlarged schematic cross-sectional view taken along line B-B of FIG. 3.

FIGS. 8(a) and 8(b) are diagrams illustrating display examples of care schedules, including absorbent article information etc., which are outputted by the care schedule proposal system according to the first embodiment.

DESCRIPTION OF EMBODIMENTS

Figure 1:
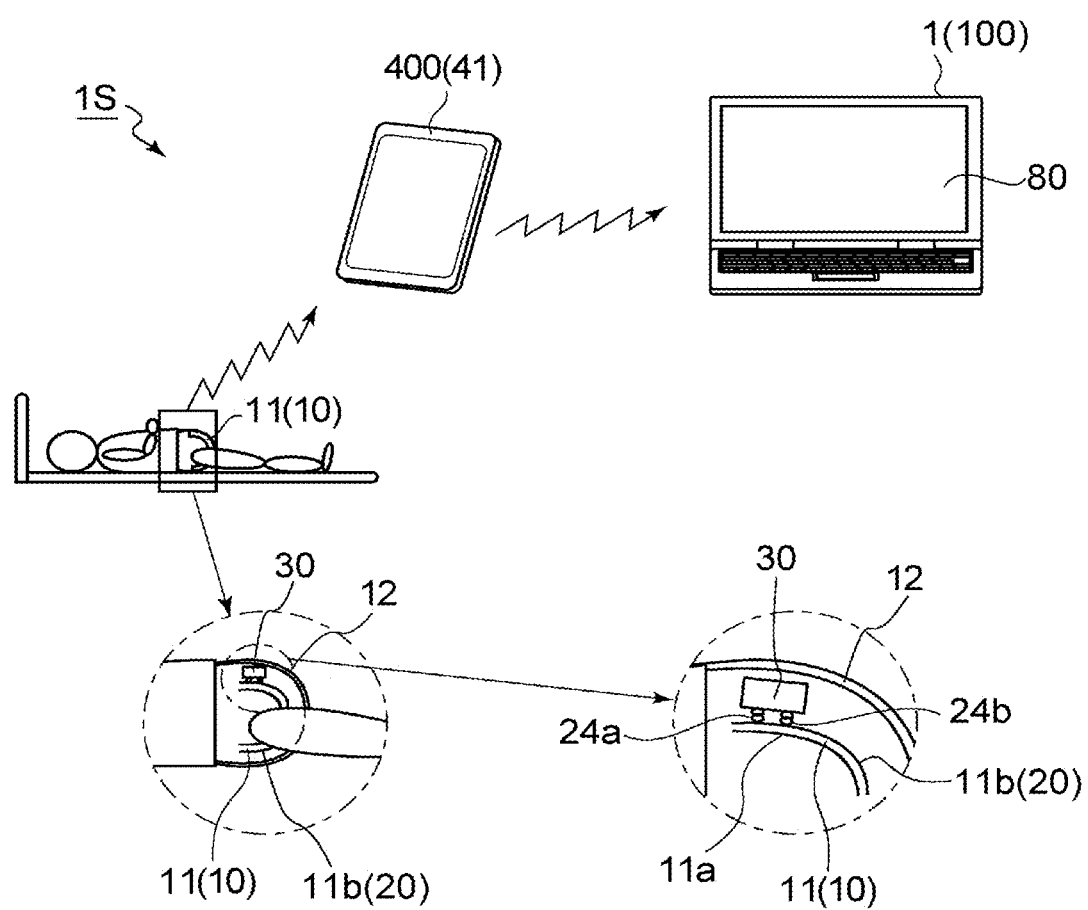
FIG. 1 is a schematic diagram illustrating a care schedule proposal system according to a preferred first embodiment of the present invention.

In hospitals, nursing-care facilities and the like, absorbent articles such as diapers used by care-receivers are changed usually a plurality of times a day at predetermined time instants. The urination amount of a care-receiver differs depending on various time periods, such as in the morning, the afternoon, or the nighttime. Thus, a caregiver predicts the urination amount that can be absorbed by an absorbent article until the next changing time, and uses an absorbent article having an absorption capacity that is equal to or greater than the predicted urination amount. In such use, it is desirable to use an absorbent article having an appropriate absorbency corresponding to the urination amount until the next changing time. However, a caregiver may worry about leakage of urine occurring in cases where the urination amount exceeds the absorption capacity of an absorbent article, and may thus use an absorbent article that has an absorbency greatly exceeding the actual urination amount and is thus bulkier than necessary. This, however, often impairs the quality of life (QOL) of a care-receiver who is made less easy to move. In view of such circumstances, it is desirable to use a small-as-possible absorbent article that has an absorption capacity sufficient for absorbing the urination amount until the next changing time and has an absorption capacity not excessively exceeding the urination amount, and that has a moderate absorbency corresponding to the urination amount until the next changing time.

The situation is the same also in cases where a care-receiver is cared for in an ordinary household. More specifically, in an ordinary household, stocking many types of absorbent articles may become a burden in many ways, and thus, often an excessively-large absorbent article having a large-as-possible absorption capacity is purchased and used to prevent leakage of urine occurring when the urination amount exceeds the absorption capacity. This results in common use of an absorbent article that is bulkier than necessary, which also often impairs the QOL of a care-receiver. Further, in ordinary households, absorbent articles on hand are often used by being superposed on one another as a countermeasure against leakage of urine from the absorbent article. The use of multiple absorbent articles further impairs QOL, given that even the use of a single piece of absorbent article impairs QOL.

The technique disclosed in Patent Literature 1, however, cannot suggest an absorbent article having an absorbency corresponding to the urination amount until the next changing time. The technique disclosed in Patent Literature 2 describes the derivation of a wearer's urination pattern, but as in Patent Literature 1, cannot suggest an absorbent article having an absorbency corresponding to the urination amount until the next changing time. The technique disclosed in Patent Literature 3 evaluates the movement of a wearer and predicts the urination amount, and thus, there is a possibility that the actual urination amount is different from the predicted urination amount. The technique disclosed in Patent Literature 4 is applicable to children during toilet training, and thus is difficult to apply to care-receivers that require absorbent article changing at predetermined time instants.

Further, the technique disclosed in Patent Literature 1 is for notifying a caregiver of the need to change absorbent articles, and is not for predicting the next time instant for changing the absorbent article in accordance with the condition of the care-receiver and the performance of the absorbent article. Thus, even when a caregiver is caring for another care-receiver or performing other tasks, the caregiver may need to respond by using an alarm etc. Further, although the technique disclosed in Patent Literature 2 focuses on the care-receiver, the technique merely makes the caregiver take care of urination with higher priority, thus impairing the degree of freedom in the caregiver's work.

The technique of Patent Literature 3 also involves the same problems as the technique of Patent Literature 4.

The present invention therefore relates to a care schedule proposal device, a care schedule proposal method, and a care schedule proposal system capable of efficiently employing an absorbent article that has an absorption capacity sufficient for absorbing an urination amount until the next changing time and has an absorption capacity not excessively exceeding the urination amount, and that has a moderate absorbency corresponding to the urination amount until the next changing time.

The present invention is a care schedule proposal device including: a urination data storage unit that stores, together with urination time instant data, urination amount data of a wearer as acquired from a urine absorption amount of an absorbent article that absorbs urine; an absorbent article information storage unit that stores article information including a urine absorption capacity of the absorbent article; a changeable time storage unit that stores a changeable time instant or a changeable time period that can serve as a candidate for a changing time instant for changing the absorbent article; and a changing schedule proposal unit that proposes a changing schedule for changing the absorbent article. The changing schedule proposal unit includes a changing schedule computation unit and a changing schedule outputting unit. The changing schedule computation unit finds, on the basis of the urination amount data and the urination time instant data stored in the urination data storage unit, a total urination amount within a predetermined time period defined by a wearing-start candidate time instant and a wearing-end candidate time instant which are selected from the changeable time instant or the changeable time period stored in the changeable time storage unit. The changing schedule computation unit performs, by comparing the total urination amount that has been found and the urine absorption capacity of the absorbent article stored in the absorbent article information storage unit, computation for finding at least either the absorbent article or the predetermined time period in a manner that the urine absorption capacity of the absorbent article does not fall below the total urination amount. The changing schedule outputting unit presents schedule information including at least either the absorbent article or the predetermined time period found by the changing schedule computation unit.

Figure 7:
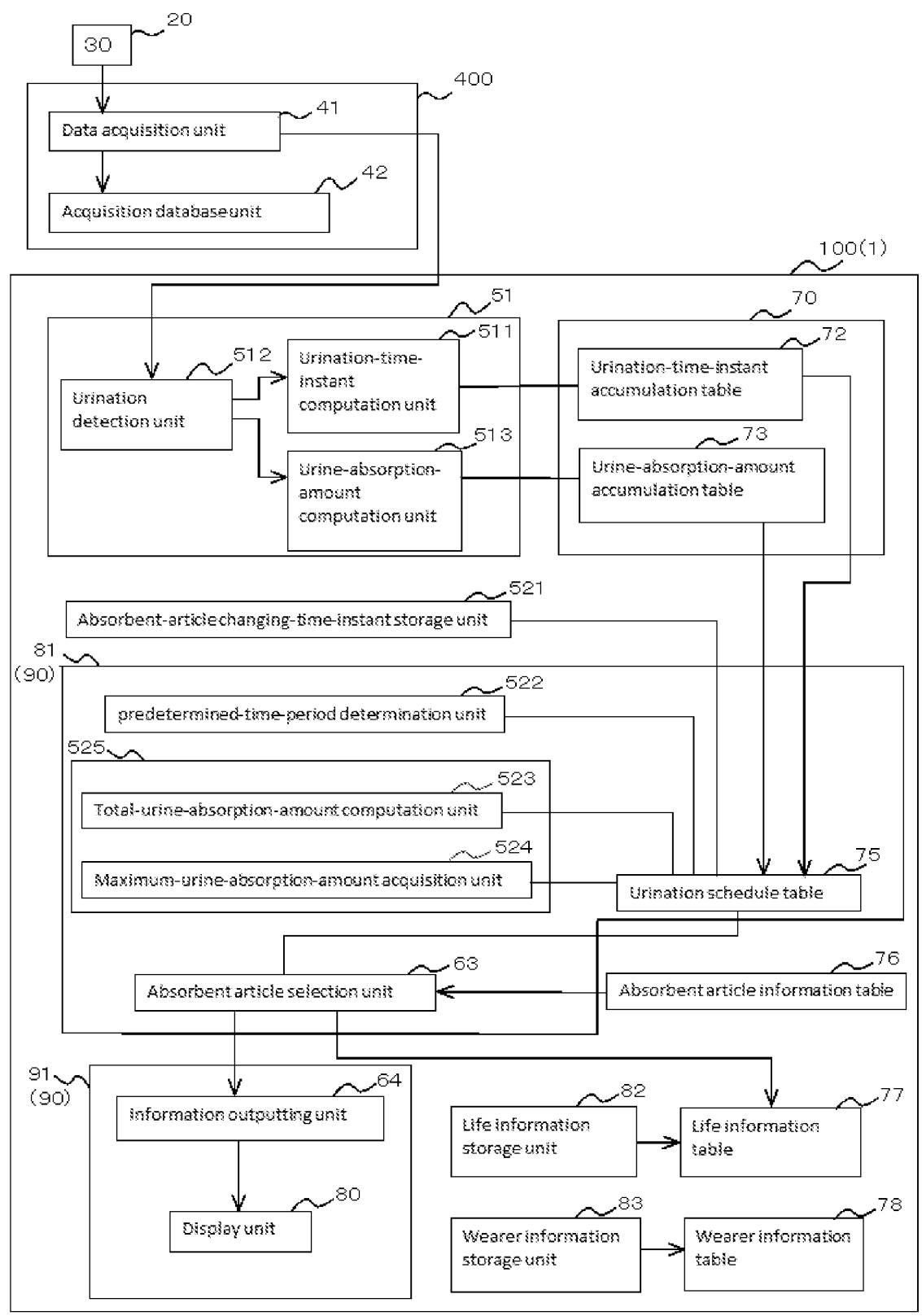
FIG. 7 is a schematic diagram illustrating a configuration example of the care schedule proposal system according to the first embodiment illustrated in FIG. 1.

An embodiment of a care schedule proposal system 1S of the present invention is described below according to a preferred first embodiment with reference to the drawings. As illustrated in FIGS. 1 and 7, the care schedule proposal system 1S according to the preferred first embodiment of the present invention includes: a urination sensor 20 (see FIGS. 1 and 3) that is attached to an absorbent article for absorbing urine, and that measures the spreading of urine by employing impedance; a urination data acquisition unit 41 that acquires urination data of a wearer from a urine absorption amount of the absorbent article on the basis of changes-over-time in impedance caused by wetting/spreading of urine in the absorbent article as measured by the urination sensor 20; and a care schedule proposal device 1 including a changing schedule proposal unit 90 that selects and proposes an absorbent article in accordance with the urination data. The care schedule proposal system 1S of the present embodiment is used, for example, in a hospital or a nursing-care facility to acquire urination information related to urination amounts and urination time instants of bedridden care-receivers, and to propose, to caregivers such as nurses, absorbent articles suitable for the respective wearers to be used in time periods determined in advance (predetermined time periods).

Figure 2:
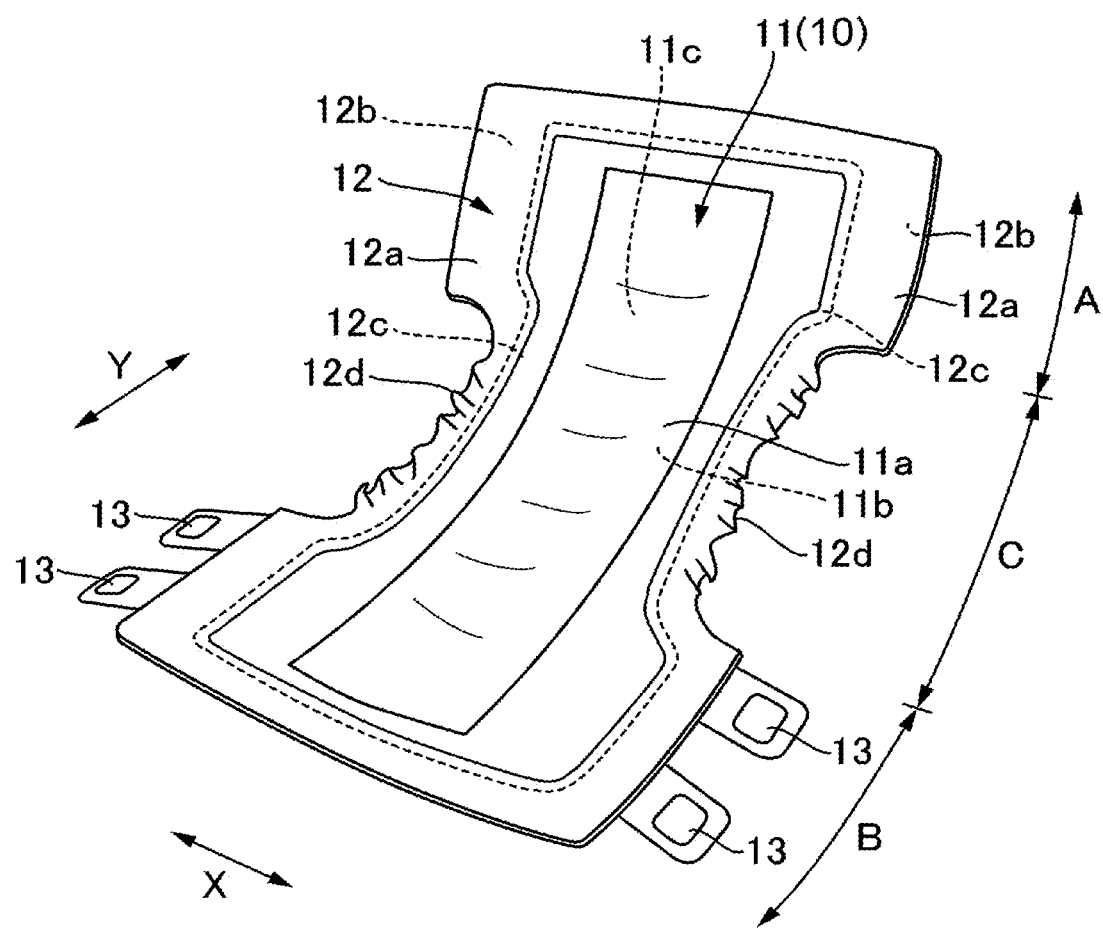
FIG. 2 is a perspective view of an absorbent article constituting the care schedule proposal system according to the first embodiment illustrated in FIG. 1.

An absorbent article 10 includes a urination sensor 20 attached to a urine absorption pad 11 which is an absorbent article having absorbency, and may be used in combination with a disposable diaper 12. As illustrated in FIG. 2, the absorbent article 10 can be divided into a front region A, a rear region B, and a crotch region C. Herein, the front region A is a section located on the wearer's front side when worn, the rear region B is a section located on the wearer's rear side when worn, and the crotch region C is a section arranged between the front region A and the rear region B.

In the figures, "Y direction" is the direction extending from the front region A to the rear region B, or from the rear region B to the front region A, and is also the same direction as the longitudinal direction of the urine absorption pad 11 or the disposable diaper 12. In the figures, "X direction" is a direction orthogonal to the Y direction, and is also the same direction as the width direction of the urine absorption pad 11 or the disposable diaper 12.

In the present Description, the "skin-facing surface" is the surface—among the front and back surfaces of the respective components, such as the later-described topsheet 11a constituting the urine absorption pad 11, for example—that is arranged on the wearer's skin side when worn, and the "non-skin-facing surface" is the surface—among the front and back surfaces of the respective components, such as the later-described topsheet 11a constituting the urine absorption pad 11, for example—that faces the opposite side from the wearer's skin side when worn.

In the present first embodiment, the absorbent article 10 is the urine absorption pad 11 to which the urination sensor 20 is attached, and can be used in combination with the diaper main body (disposable diaper) 12. As illustrated in FIG. 2, the diaper main body 12 has a structure similar to the disposable diaper disclosed in JP 2015-119784A. In FIG. 2, the urine absorption pad 11, serving as an inner member, is used in combination with the diaper main body (disposable diaper) 12, serving as an outer member. The diaper main body 12 includes: a main-body topsheet 12a having the urine absorption pad 11 attached to the inner, skin-facing surface side; a main-body backsheet 12b arranged most toward the non-skin-facing surface side; and a main-body absorbent member 12c arranged between the two sheets 12a, 12b. On the respective outer sides of the main-body absorbent member 12c in the width direction X, the diaper main body 12 also includes main-body leg elastic members (not illustrated) which are for forming leg gathers and which are arranged in a stretched state in the longitudinal direction Y. The contraction of the main-body leg elastic members (not illustrated) forms leg gathers 12d. The top-surface side of the main-body topsheet 12a may be provided with auxiliary side sheets (not illustrated) etc for forming leak-proof cuffs (not illustrated), for example.

The main-body topsheet 12a and the main-body backsheet 12b both extend outward from the main-body absorbent member 12c's lateral side edge portions extending along the longitudinal direction Y and the main-body absorbent member's end edge portions extending along the width direction X. The main-body topsheet 12a and the main-body backsheet 12b are joined together by, for example, an adhesive or fusion-bonding in extension portions that extend outward from the peripheral edge of the main-body absorbent member 12c, and inside, the main-body absorbent member 12c is provided in a sandwiched and fixed state.

The diaper main body 12 formed as described above has, as a whole, a shape in which the central portion, in the longitudinal direction Y, is narrowed inwardly. The diaper main body 12 is a so-called open-type diaper, and two pairs of fastening tapes 13 are provided at the left and right lateral side edge portions in the rear region B. A landing tape (not illustrated) where the fastening tapes 13 are fastened is provided on the outside surface (non-skin-facing surface) in the front region A. Note that, other than a disposable diaper, the outer member used in combination with the urine absorption pad 11 as the inner member may be cloth underpants or adult pull-up pants. Also, other than a urine absorption pad 11 equipped with a sensor sheet, the sensor-equipped absorbent article 10 may be a sensor-equipped disposable diaper (tape-fastening diaper or adult pull-up pants).

Figure 3:
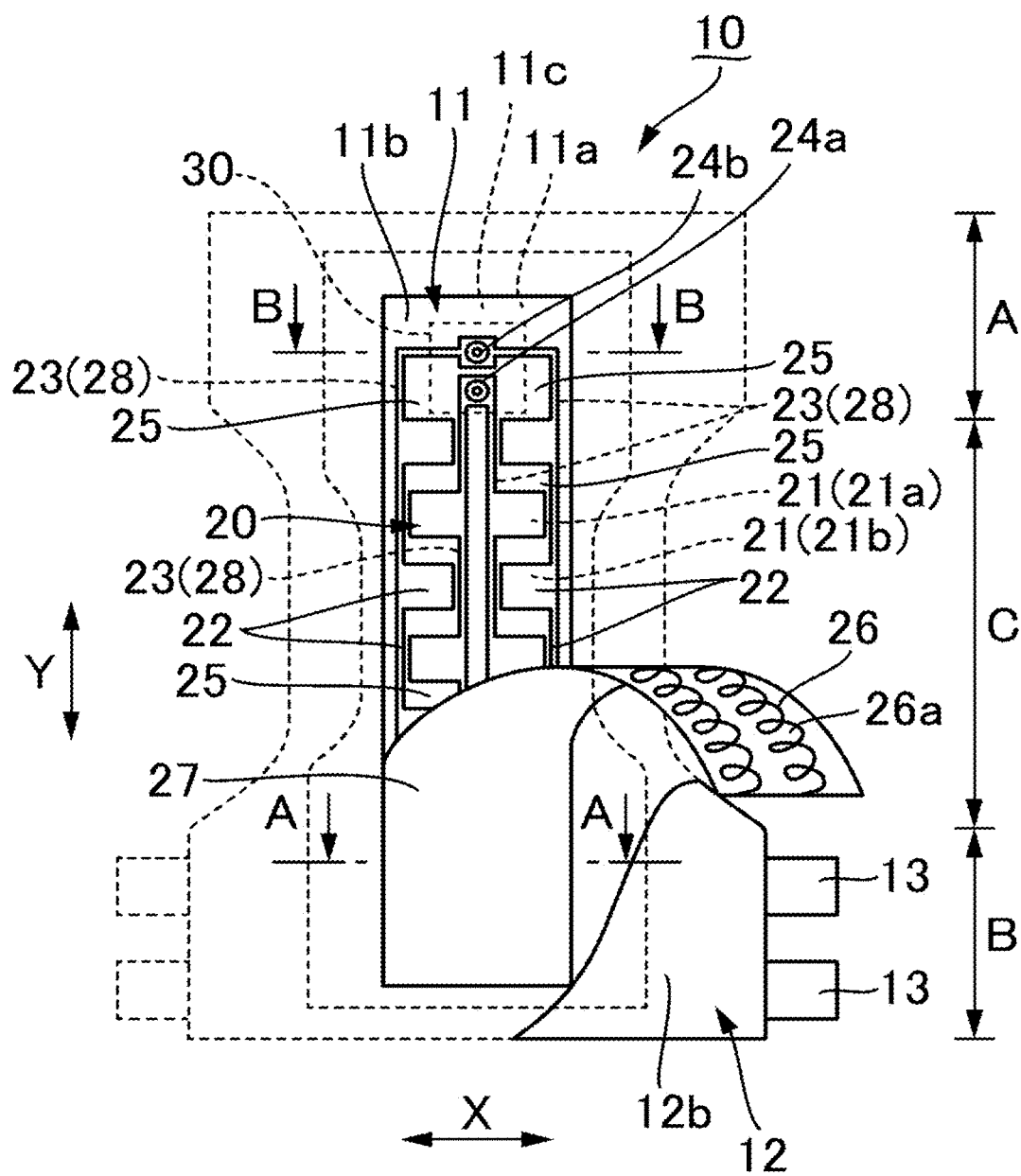
FIG. 3 is a back-side view of a urination sensor attached to a urine absorption pad illustrated in FIG. 2, the urination sensor being illustrated in a state where a portion of a cover sheet covering the urination sensor has been peeled, the urine absorption pad being viewed from the non-skin-facing surface side.

The urine absorption pad 11 of the absorbent article 10 in the present first embodiment includes: a liquid-permeable topsheet 11a arranged on the skin-facing surface side; a sparingly liquid-permeable backsheet 11b arranged on the non-skin-facing surface side; and an absorbent member 11c arranged between the two sheets 11a, 11b. More specifically, in the urine absorption pad 11, the topsheet 11a, the backsheet 11b, and the absorbent member 11c have a rectangular shape that is long in the longitudinal direction (Y direction) of the urine absorption pad 11 or the disposable diaper 12, as illustrated in FIGS. 2 and 3. The topsheet 11a and the backsheet 11b both extend outward from the absorbent member 11c's left and right lateral side edge portions extending along the longitudinal direction (Y direction) and the absorbent member's front and rear end edges in the longitudinal direction (Y direction). As illustrated in FIG. 2, the topsheet 11a's dimension in the longitudinal direction (Y direction) is the same as the backsheet 11b's dimension in the longitudinal direction (Y direction), but the dimension in the width direction (X direction) is smaller than the backsheet 11b's dimension in the width direction (X direction), as illustrated in FIG. 3. The topsheet 11a and the backsheet 11b are joined together, either directly or with another member interposed therebetween, by, for example, an adhesive or fusion-bonding in extension portions that extend outward from the peripheral edge of the absorbent member 11c, and thereby the absorbent member 11c is sandwiched and fixed. Note that, as illustrated in FIG. 4, the absorbent member 11c is formed by covering, with a single core-wrap sheet 11e, an absorbent core 11d in which water-absorbent polymer particles are retained in an aggregate of fibers, such as pulp fibers.

As illustrated in FIG. 3, the urine absorption pad 11 includes an absorbent member 11c which is oblong in the longitudinal direction (see FIGS. 4(a) and 4(b)). The urination sensor 20 is attached to the backsheet 11b constituting the urine absorption pad 11, and more specifically, is attached on the backsheet 11b's outer side (the non-skin-facing surface side) on the opposite side from the skin-facing surface side which comes into contact with the wearer's skin. In this way, the urination sensor 20 is attached to one of the plurality of sheets constituting the absorbent article 10.

The urination sensor 20 includes sensor elements 20a constituted by a plurality of printed electrodes 21 (see FIG. 4(a)) formed by applying an electroconductive ink to a printing substrate 22. The urination sensor 20 can detect the spreading of urine absorbed by the urine absorption pad 11 on the basis of changes in impedance between the plurality of printed electrodes 21.

As illustrated in FIGS. 2 to 4, the urination sensor 20 includes: a printing substrate 22; a plurality of printed electrodes 21 that constitute sensor elements 20a and that are made by an electroconductive ink applied to a surface of the printing substrate 22; conducting wire portions 23 that connect the plurality of printed electrodes 21; and terminal portions 24 to which the conducting wire portions 23 are connected. The printing substrate 22 is, for example, formed of an electrically insulating polyethylene terephthalate film. The printed electrodes 21 are in tight contact with the surface of the backsheet 11b of the urine absorption pad 11. The urination sensor 20 is covered by a cover sheet 27 made of a nonwoven fabric to which an adhesive 26 is applied (see FIGS. 3 and 5), and is bonded to the surface of the backsheet 11b of the urine absorption pad 11 by the adhesive 26 applied to the cover sheet 27. The adhesive 26 is applied in a discretionary application pattern, such as a spiral-shaped application pattern. The cover sheet 27 includes: applied sections where the adhesive 26 is applied; and non-application sections 26a where the adhesive is not applied. By providing the cover sheet 27 with the non-application sections 26a, sections of the urination sensor 20 other than the printed electrodes 21 and the conducting wire portions 23 of the printing substrate 22 form air-passage openings 25 that retain an air-passage function. The backsheet 11b is an electrically insulating, sparingly liquid-permeable sheet, and the printing substrate 22 is an electrically insulating substrate. The printed electrodes 21 and the conducting wire portions 23 are covered by the backsheet 11b and the printing substrate 22. The top-surface side of the urine absorption pad 11 may be provided with auxiliary side sheets (not illustrated) for forming leak-proof cuffs (not illustrated), for example. Although the urination sensor 20 of the present embodiment includes air-passage openings 25, the air-passage openings 25 do not have to be provided.

Preferably, the electroconductive ink is an ink made by blending a metal powder, such as silver powder, as an electroconductive substance. In the present first embodiment, like the printed electrodes 21, the conducting wire portions 23 are made of a printed electroconductive layer 28 (see FIGS. 4(a) and 4(b)) formed by the electroconductive ink applied to the surface of the printing substrate 22.

In the present first embodiment, a plurality of sensor elements 20a are formed in the urination sensor 20 by the plurality of printed electrodes 21 made by the electroconductive ink applied to the surface of the printing substrate 22. More specifically, the plurality of printed electrodes 21 include a plurality of positive electrodes 21a and a plurality of negative electrodes 21b, and the plurality of positive electrodes 21a and the plurality of negative electrodes 21b constitute the plurality of sensor elements 20a. By employing the sensor elements 20a constituted by the positive electrodes 21a and the negative electrodes 21b, the urination sensor 20 detects changes in impedance of the sensor elements 20a. On the basis of the detected changes in impedance, the care schedule proposal system 1S can detect whether or not a wearer has urinated and/or detect the spreading of urine absorbed by the urine absorption pad 11 upon urination. Further, the system can measure, for example, the urine absorption amount (urination amount) from the spreading of urine.

From the viewpoint of improving detection accuracy, it is preferable that the urination sensor 20 includes a plurality of sensor elements 20a formed by the plurality of printed electrodes 21.

Figure 5:
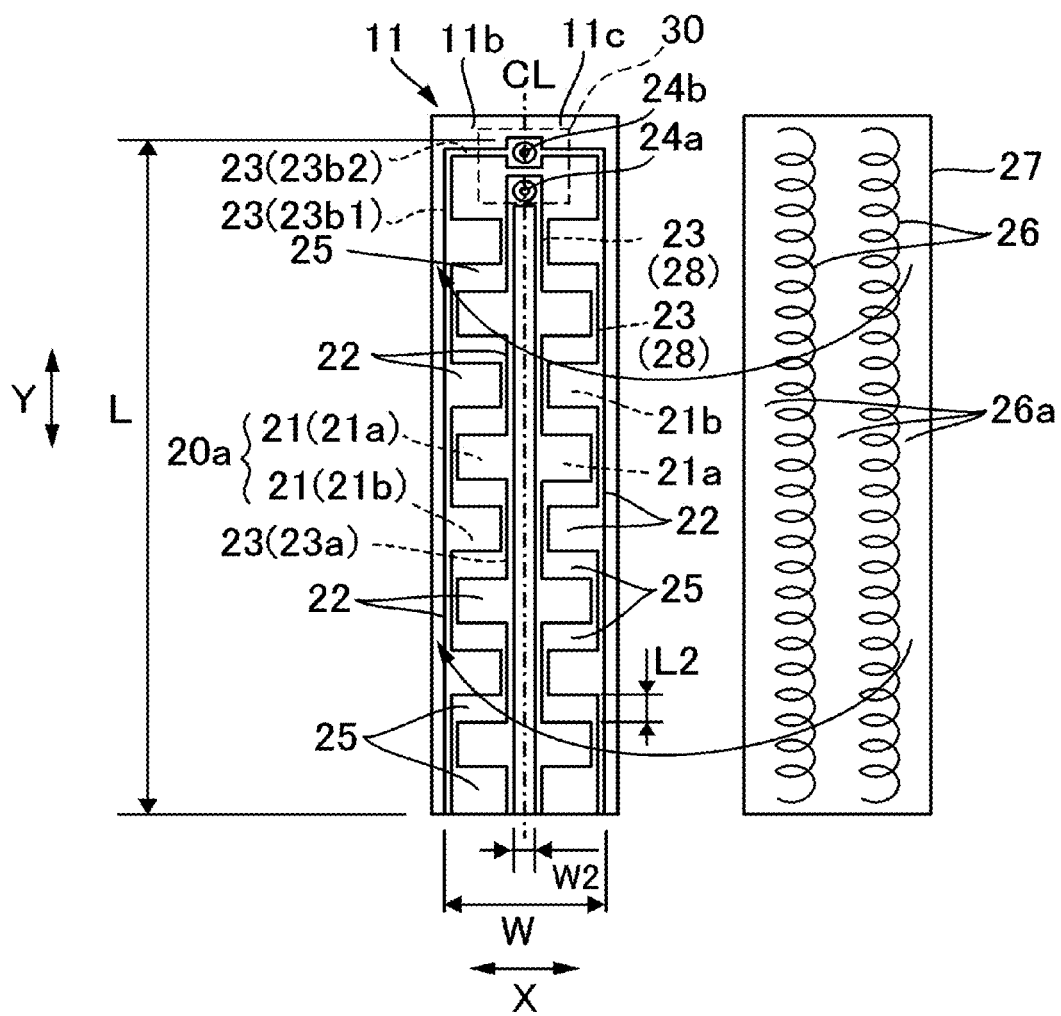
FIG. 5 is a back-side view of the cover sheet and the urine absorption pad in a state before the cover sheet is attached, the back-side view illustrating the urination sensor provided to the urine absorption pad and the cover sheet to be attached so as to cover the urination sensor.

In the present first embodiment, the plurality of printed electrodes 21 are formed in a planar form by applying the electroconductive ink to the surface of the printing substrate 22, and as illustrated in FIG. 5, the printed electrodes 21 are arranged at eight places along the longitudinal direction Y of the urine absorption pad 11 with intervals therebetween. The printed electrodes 21 located in eight places are referred to hereinbelow as an electrode array. The electrode array is configured such that the positive electrodes 21a and negative electrodes 21b are arranged alternately, and the positive electrode 21a and the negative electrode 21b adjacent to one another in the longitudinal direction Y constitute the aforementioned sensor element 20a. There are two of these electrode arrays with a predetermined interval therebetween in the width direction X. Stated differently, the sensor elements 20a, as a whole, are configured such that there are printed electrodes 21 in sixteen places, dispersedly arranged uniformly in the width direction X and the longitudinal direction Y. As for two printed electrodes 21 adjacent to one another in the width direction X, a positive electrode may be paired with a negative electrode, and a negative electrode may be paired with a positive electrode; in the present first embodiment, however, a positive electrode is paired with a positive electrode, and a negative electrode is paired with a negative electrode. It should be noted that the number of places where the printed electrodes 21 are arranged is preferably from six to twelve in the longitudinal direction Y of the urine absorption pad 11.

As described above, the plurality of printed electrodes 21 are arranged longitudinally in two rows along the longitudinal direction Y of the urine absorption pad 11, and the electrodes are arranged at a total of sixteen places, eight in each electrode array (see FIG. 5). In the printed electrodes 21 arranged at eight places in each electrode array, the positive electrodes 21a and the negative electrodes 21b, which are arranged alternately at four places each in the longitudinal direction Y, are connected respectively by the conducting wire portions 23. More specifically, the positive electrodes 21a arranged at four places in each electrode array are connected by conducting wire portions 23a arranged so as to extend linearly along the longitudinal direction Y on the inner side in the width direction X—i.e., closer to the center line CL; one end portion of the conducting wire portion 23a is connected to a terminal portion 24a provided at an end section in the longitudinal direction Y. Note that the center line CL illustrated in FIG. 5 is the center line of the urine absorption pad 11 or the disposable diaper 12 extending along the longitudinal direction (Y direction).

The negative electrodes 21b at four places in the respective electrode arrays are connected by conducting wire portions 23b1 arranged so as to extend linearly along the longitudinal direction Y on both lateral sides along the longitudinal direction Y, and one end portion, in the longitudinal direction Y, of the respective conducting wire portions 23b1 is connected to one end portion of respective conducting wire portions 23b2 arranged so as to extend linearly in the width direction X. The other end of each conducting wire portion 23b2 is connected to a terminal portion 24b provided at an end section in the longitudinal direction Y. As described above, the plurality of positive electrodes 21a, the conducting wire portions 23a and the terminal portion 24a are configured so as to be arranged on the urination sensor 20's inner side (i.e., closer to the center line CL) in a planar view of the urination sensor 20. On the other hand, the plurality of negative electrodes 21b, the conducting wire portions 23b1, 23b2 and the terminal portion 24b are configured so as to be arranged on the outer sides of the plurality of positive electrodes 21a so as to surround the plurality of positive electrodes 21a in a planar view of the urination sensor 20.

In the present first embodiment, the urination sensor 20's negative electrodes 21b arranged on the outer sides are grounded. From the viewpoint of reducing the intrusion of external noise and improving measurement accuracy, it is preferable that the plurality of negative electrodes 21b are grounded via the terminal portion 24b.

In the present first embodiment, the urination sensor 20's printed electrodes 21—i.e., the positive electrodes 21a and the negative electrodes 21b are all formed in the same rectangular shape. However, from the viewpoint of reducing the amount of usage of the electroconductive ink and cutting down on costs, the printed electrodes 21 may be formed by applying the electroconductive ink in, for example, a lattice form having non-application sections. The shape (design), size, and arrangement/formation of the printed electrodes 21 are not limited to those of the present embodiment, and can be designed as appropriate.

In the urination sensor 20 of the present first embodiment, like the printed electrodes 21, the conducting wire portions 23 (conducting wire portions 23a, 23b) for connecting the respective electrode groups, each including the printed electrodes 21 at four places, to the respective terminal portions 24 (terminal portions 24a, 24b) are formed by the printed electroconductive layer 28 (see FIGS. 4(a) and 4(b)) formed by the electroconductive ink applied to the surface of the printing substrate 22. From the viewpoint of easy provision onto the backsheet 11b of the urine absorption pad 11, it is preferable to form the conducting wire portions 23 by the electroconductive layer 28 as described above.

In the present first embodiment, a metal snap having electroconductivity is used for the terminal portion 24 (terminal portion 24a, 24b) as a known terminal portion. As illustrated in FIG. 4(b), the metal snap 24 is constituted by a female hook 241 and a male hook 242. The female hook 241 and the male hook 242 are fit together in a state where the cover sheet 27, the conducting wire portions 23, and the printing substrate 22 are sandwiched between these metal hooks 241, 242 in the thickness direction Z. The terminal portion 24 (terminal portion 24a, 24b) may be made by using any one of a metal connector, a zipper, a hook-and-loop fastener (e.g. Magic Tape (registered trademark)), a screw, a hook, or a meshing-type fastening means.

In the present first embodiment, the printed electrodes 21 and the conducting wire portions 23 (the printed electroconductive layer 28) constituting the urination sensor 20 are formed by applying the electroconductive ink to the surface of the printing substrate 22 according to a predetermined arrangement/form (see FIG. 5).

The printing substrate 22 preferably has physical properties that can withstand shrinking at the time of drying the applied electroconductive ink, and more preferably, is an electrically insulating resin film. Examples of such materials include materials having a melting point of 200° C. or higher, such as polyethylene terephthalate or polyimides. The thickness of the printing substrate 22 is preferably from 35 to 75 μm.

For the electroconductive ink to be applied to the printing substrate 22, it is possible to use a material obtained by blending, for example, a carbon powder or a metal powder such as silver or copper, as an electroconductive substance, to an ink which is a mixture including, for example, a dispersing agent, a binder, resin, and a curing agent. The electroconductive ink is preferably an ink in which a silver powder is blended as a metal powder.

When applying the electroconductive ink to the printing substrate 22 to form the printed electrodes 21 and the conducting wire portions 23 by the printed electroconductive layer 28, the electroconductive ink may be printed (applied) only once, but from the viewpoint of increasing the sensitivity for detecting urination, the electrodes and the conducting wire portions may be formed by overlaying and printing (applying) the ink a plurality of times. In this case, it is preferable to perform overlaying and printing one to ten times. As for the method for applying and printing the electroconductive ink, it is possible to employ one of various known methods such as inkjet printing, rotary printing, flexographic printing, screen printing, or gravure printing.

In the present first embodiment, sections of the printing substrate 22 where the electroconductive ink is not applied—i.e., substantially the entirety of the printing substrate 22 in regions other than the printed electrodes 21 and the conducting wire portions 23—are absent. More specifically, the regions between the positive electrodes 21*a* and the negative electrodes 21*b* forming the sensor elements 20*a*—i.e., the sections other than the printed electrodes 21 and the conducting wire portions 23 of the printing substrate 22—form air-passage openings 25 which function as air-passage regions through non-application sections 26*a* where the adhesive is not applied (see FIG. 5). From the viewpoint of retaining air permeability of the backsheet 11*b* of the urine absorption pad 11 to which the urination sensor 20 is attached, it is preferable to provide the printing substrate 22 with the air-passage openings 25 as illustrated in FIG. 5. It should be noted that the printed electrodes 21 and the conducting wire portions 23 may first be printed on the printing substrate 22 according to a desired printing pattern, and then sections where the electroconductive ink is not applied may be cut. Alternatively, the electroconductive ink may be printed in advance onto the entire surface of the printing substrate 22 made of a resin film, and then the printed electrodes and the conducting wire portions may be formed by cutting the printing substrate 22, to which the electroconductive ink has been printed, into a shape according to a desired printing pattern. The periphery of the air-passage opening 25, serving as air-passage regions, only needs to be substantially surrounded by a rim, and a portion of the peripheral rim may be discontinuous.

In the present first embodiment, the printed electrodes 21 and the printed electroconductive layer 28 formed by applying the electroconductive ink to the printing substrate 22 are attached to the backsheet 11*b* by using a cover sheet 27 which is made of an air-permeable nonwoven fabric and which is bonded to the backsheet 11*b* of the urine absorption pad 11 while covering the urination sensor 20. It is preferable that, on the non-skin-facing surface side of the backsheet 11*b* (on the side where the cover sheet 27 is to be bonded), a marking for accurately bonding the cover sheet 27 to the backsheet 11*b* is printed in a position where the cover sheet 27 is to be bonded.

The printed electrodes 21 and the printed electroconductive layer 28 are attached, together with the printing substrate 22, to the backsheet 11*b* by using the cover sheet 27 in a state where they are placed in tight contact with a surface (surface on the opposite side from the skin-facing surface side) of the backsheet 11*b* of the urine absorption pad 11. The adhesive 26 is applied to the cover sheet 27 on the inside surface thereof, which is the skin-facing surface side. By causing the adhesive to bond to the backsheet 11*b* of the urine absorption pad 11 through the air-passage openings 25—which are formed in the removed-and-absent sections of the printing substrate 22—and on the outside of the outer periphery of the printing substrate 22, the cover sheet 27 is attached so as to cover the urination sensor 20 in a state where the urination sensor 20 is sandwiched between the cover sheet and the backsheet 11*b*. Thus, the urination sensor 20 which includes the printing substrate 22, the plurality of printed electrodes 21 formed by the electroconductive ink, the conducting wire portions 23 constituted by the printed electroconductive layer 28 formed by the electroconductive ink, and the terminal portions 24—is superposed on and provided to the backsheet 11*b* along the backsheet 11*b* of the urine absorption pad 11 in a state where the printed electrodes 21 are in tight contact with the surface of the backsheet 11*b* of the urine absorption pad 11.

For the backsheet 11*b*, the topsheet 11*a*, and the absorbent member 11*c* of the urine absorption pad 11, it is possible to use, without particular limitation, materials conventionally used in absorbent articles such as disposable diapers, urine absorption pads 11, and sanitary napkins. For the backsheet 11*b*, it is possible to use, for example, an insulating, sparingly liquid-permeable sheet (e.g. a moisture-permeable resin film) used in absorbent articles, or a layered sheet in which a nonwoven fabric made by one of various manufacturing methods (e.g., an air-through nonwoven fabric, a spun-bonded nonwoven fabric, a spun-laced nonwoven fabric, or a needle-punched nonwoven fabric) is layered on the aforementioned insulating sheet. For the topsheet 11*a*, it is possible to use, for example, a hydrophilic liquid-permeable nonwoven fabric or three-dimensional porous film. For the absorbent core constituting the absorbent member 11*c*, it is possible to use, for example, a member in which absorbent polymer particles are retained in an aggregate of fibers, such as pulp fibers. For the core-wrap sheet constituting the absorbent member 11*c*, it is possible to use a hydrophilic sheet, such as a core-wrap sheet made of water-permeable thin paper (tissue paper) or a water-permeable nonwoven fabric.

Further, in the present first embodiment, for the nonwoven fabric constituting the cover sheet 27, it is possible to use a material conventionally used in absorbent articles such as diapers.

Further, in the present embodiment, for the adhesive 26 applied to the cover sheet 27, it is possible to preferably use an adhesive for use with the skin. Examples of such adhesives include acrylic-based adhesives and rubber-based adhesives, and it is possible to preferably use a rubber-based adhesive.

In the present first embodiment, for the application pattern including non-application sections 26*a* where the adhesive 26 is not applied, it is possible to employ one of known application patterns such as spiral-shaped, summit-shaped, omega-shaped, curtain-shaped or stripe-shaped application patterns. From the viewpoint of retaining air permeability of the sheet to which the urination sensor 20 is attached, it is preferable to employ an application pattern in which there are non-application sections 26*a* in the air-passage openings 25, and more preferably a spiral-shaped pattern.

In the present first embodiment, a data collection unit 30 is connected to the urination sensor 20, as illustrated in FIG. 1. The data collection unit 30: applies a voltage that changes periodically with time—for example, a rectangular-wave voltage with a predetermined frequency—to the plurality of positive electrodes 21*a* and the plurality of negative electrodes 21*b* (i.e., the plurality of sensor elements 20*a*) illustrated in FIG. 5; acquires changes in impedance corresponding to the amount of urine absorbed by the absorbent member 11*c*; and transmits the acquired data to a later-described data acquisition unit (urination data acquisition unit) 41 of the care schedule proposal system 1S.

Figure 6:
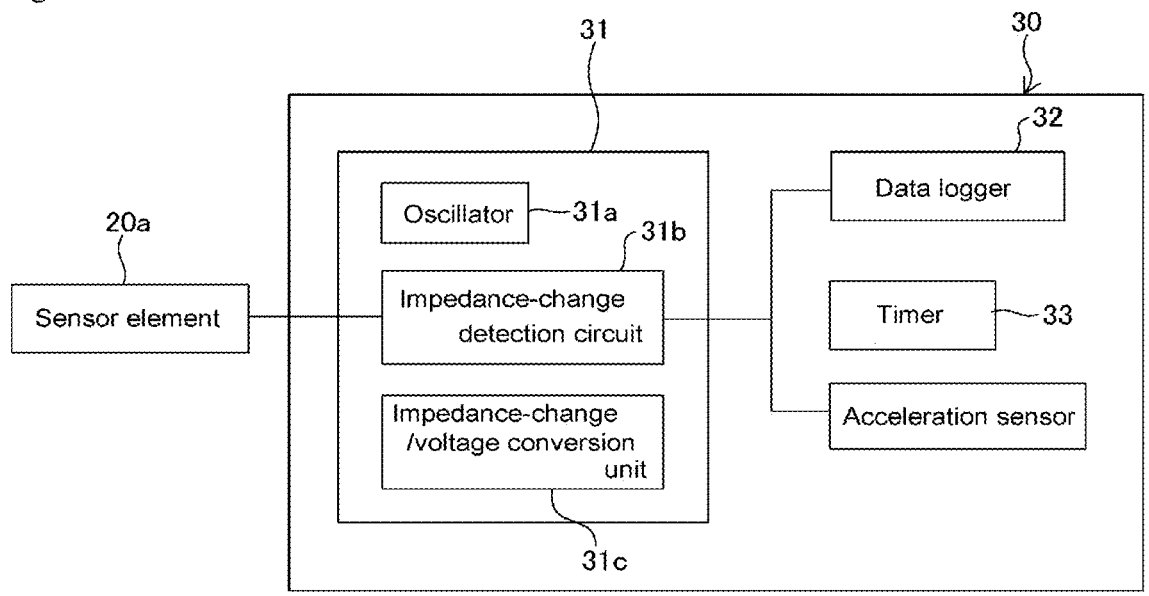
FIG. 6 is a block diagram of a data collection unit that detects and acquires changes in impedance.

As illustrated in FIG. 6, the data collection unit 30 includes: an impedance detection unit 31 that detects changes in impedance; a data logger 32 that stores impedance change data detected by the impedance detection unit 31; and a timer 33 that outputs time data.

The impedance detection unit 31 applies a voltage to the entire circuit constituted by the plurality of sensor elements 20a of the urination sensor 20 attached to the urine absorption pad 11, and detects changes in impedance of the plurality of sensor elements 20a. More specifically, as illustrated in FIG. 6, the impedance detection unit 31 includes: an oscillator 31a that oscillates a predetermined frequency signal; an impedance-change detection circuit 31b that detects the total amount of change in impedance of the sensor elements 20a by using the frequency signal from the oscillator 31a; and an impedance-change/voltage conversion unit 31c that converts the total amount of change in impedance detected by the impedance-change detection circuit 31b into voltage-change data.

For example, the impedance-change detection circuit 31b configures a bridge circuit by employing impedance Zx of the sensor elements 20a and impedance elements Z1 to Z3 with known resistance values. In the impedance detection unit 31, the oscillator 31a is used to apply a predetermined frequency signal (e.g., a 600 KHz rectangular wave between 0 and 1.8 V) to the input terminal of the impedance-change detection circuit 31b. The impedance-change/voltage conversion unit 31c detects a difference in voltage between the divided voltage by the impedance elements Z1 and Z2 and the divided voltage by the impedance element Z3 and the impedance Zx of the sensor elements 20a, and outputs, to the data logger 32, voltage data of a voltage value corresponding to the magnitude of the impedance Zx.

The voltage data outputted to the data logger 32 are outputted, per given time, and stored together with time data outputted from the timer 33. The time interval for outputting is preferably from 0.1 to 60 seconds, more preferably from 0.1 to 10 seconds.

The data logger 32 stores data acquired from the impedance detection unit 31. The data logger 32 transmits, in a wireless manner, stored data to a later-described data acquisition unit 41 in response to a request from the data acquisition unit 41 or upon detecting connection with the data acquisition unit 41.

The data collection unit 30 also includes a power supply (a battery in the present embodiment) for generating the voltage to be applied to the printed electrodes 21 (the positive electrodes 21a and the negative electrodes 21b). As illustrated in FIG. 4(b), the data collection unit 30 is attached to the urination sensor 20 so as to cover the terminal portions 24a, 24b. In the present first embodiment, the data collection unit 30 applies a voltage to the positive electrodes 21a via the terminal portion 24a, and grounds the negative electrodes 21b.

In the present first embodiment, the data collection unit 30 transmits, via wireless communication, the data stored by the data logger 32 to a tablet-type personal computer which is the data acquisition unit 41. The data transmitted from the data logger 32 to the data acquisition unit 41 is voltage data of a voltage value corresponding to the magnitude of the impedance Zx, and the voltage data is transmitted, via wireless communication, to the data acquisition unit 41 together with time instant data. Hereinbelow, the voltage data is also referred to as impedance-change-amount data.

Note that data transmission from the data collection unit 30 to the data acquisition unit 41 may be done in a wired manner.

The data acquisition unit 41 acquires, for every predetermined time, the impedance-change-amount data stored in the data logger 32 of the data collection unit 30, and temporarily stores the data in an acquisition database unit 42. The data acquisition unit 41 then supplies the acquired impedance-change-amount data to a urination data computation unit 51 of the care schedule proposal device 1 by wired or wireless communication. The data acquisition unit 41 supplies, to the urination data computation unit 51, the acquired impedance-change-amount data at least once per hour, preferably a plurality of times per hour, more preferably of times per 15 minutes, even more preferably once every 1 to 10 seconds.

In the present first embodiment, as illustrated in FIG. 1, the data acquisition unit (urination data acquisition unit) 41 is configured by using an information processing device 400, which is a tablet-type personal computer (referred to also as "PC"). The information processing device 400 includes an LCD as a display device, and includes a touch panel as an input device. As described above, a known general-purpose computer can be used for the data acquisition unit 41. A general-purpose computer includes a central processing unit (CPU), a read only memory (ROM), a random access memory (RAM), a hard disk drive (HDD), a display unit, an input unit, etc. Examples of general-purpose computers include personal computers, such as desktop PCs, laptop PCs, notebook-sized PCs, netbook PCs, handheld PCs and tablet PCs, server machines, and mobile terminals (smartphones, etc.). Examples of display units include liquid crystal displays (LCDs), cathode-ray tubes (CRTs), and electroluminescence displays (EL displays). Examples of input units include keyboards and touch panels.

In the present first embodiment, an information processing device 100 constituting the care schedule proposal device 1 is a device different from the information processing device 400 constituting the data acquisition unit 41. The information processing device 100 is a notebook-type PC, which is one of the aforementioned general-purpose computers, and includes an LCD as a display device and a keyboard as an input device.

Predetermined programs are installed in the information processing device 100 constituting the care schedule proposal device 1 illustrated in FIG. 1, and thereby, as illustrated in FIG. 7, the information processing device 100 functionally achieves: a urination data storage unit 70 including a urination-time-instant accumulation table 72 and a urine-absorption-amount accumulation table 73; an absorbent article information table 76 serving as an absorbent article information storage unit; an absorbent-article changing-time-instant storage unit 521 serving as a changeable time storage unit; and a total-urine-absorption-amount computation unit 523, a maximum-urine-absorption-amount acquisition unit 524, and an absorbent article selection unit 63 which constitute a changing schedule computation unit 81. Stated differently, the care schedule proposal device 1 can be configured by installing predetermined programs to the information processing device 100. In cases where the information processing device 100 includes an input/output interface, the predetermined programs can be read in from another device, as necessary, through a medium usable by the input/output interface. Herein, "medium" refers, for example, to a recording medium attachable/detachable to/from the input/output interface, or a communication medium such as a wired, wireless or optical network, or a medium such as a carrier wave or a digital signal propagating through the network. A portion, or the entirety, of the functions achieved by the programs may be achieved by a hardware circuit, for example.

By installing the predetermined programs, the care schedule proposal device 1 of the present first embodiment is configured to include: a urination data storage unit 70 that stores, together with urination time instant data, urination amount data of a wearer as acquired from a urine absorption amount of an absorbent article 10 that absorbs urine; an absorbent article information storage unit (absorbent article information table) 76 that stores article information including a urine absorption capacity of the absorbent article 10; a changeable time storage unit (absorbent-article changing-time-instant storage unit) 521 that stores a changeable time instant or a changeable time period that can serve as a candidate for a changing time instant for changing the absorbent article 10; and a changing schedule proposal unit 90 that proposes a changing schedule for changing the absorbent article 10. The changing schedule proposal unit 90 includes a changing schedule computation unit 81 and a changing schedule outputting unit 91. The changing schedule outputting unit 91 includes an information outputting unit 64 and a display unit 80. The changing schedule computation unit 81 finds, on the basis of the urination amount data and the urination time instant data stored in the urination data storage unit 70, a total urination amount within a predetermined time period defined by a wearing-start candidate time instant and a wearing-end candidate time instant, which are selected from the changeable time instant or the changeable time period stored in the changeable time storage unit 521 (in the present first embodiment, changeable time instants which are time instants when the absorbent article can be changed) and which are temporarily-determined one changing time instant and next changing time instant. The changing schedule computation unit 81 performs, by comparing the total urination amount that has been found and the urine absorption capacity of the absorbent article 10 stored in the absorbent article information storage unit 76, computation (information processing) for finding at least either the absorbent article or the predetermined time period in a manner that the urine absorption capacity of the absorbent article 10 does not fall below the total urination amount that has been found. The changing schedule outputting unit 91 presents schedule information including at least either the absorbent article or the predetermined time period found by the changing schedule computation unit 81.

Further, in the present first embodiment, the absorbent article information storage unit 76 stores article information including respective urine absorption capacities for a plurality of types of absorbent articles 10. The absorbent article selection unit 63 of the changing schedule computation unit 81 performs computation for: comparing the respective urine absorption capacities of the plurality of types of absorbent articles 10 stored in the absorbent article information table 76, which serves as the absorbent article information storage unit, with the total urination amount within a predetermined time period defined by a wearing-start time (data collection start time) and a wearing-end time (data collection end time), which are preferably selected from absorbent-article changing time instants, serving as changeable time instants, preferably stored in the absorbent-article changing-time-instant storage unit 521 serving as the changeable time storage unit; and determining an absorbent article in a manner such that the urine absorption capacity of the absorbent article 10 does not fall below the total urination amount and such that the urine absorption capacity of the absorbent article 10 becomes closest to the total urination amount. The changing schedule outputting unit 91 presents, together with the wearing-start time, the absorbent article that has been determined. More specifically, the absorbent article information storage unit 76 stores article information including respective urine absorption capacities for a plurality of types of absorbent articles, and the changing schedule outputting unit 91 presents, together with at least the wearing-start time, the absorbent article selected from the plurality of types of absorbent articles.

Further, in the present first embodiment, the changing schedule computation unit 81 preferably performs schedule computation for finding at least either the absorbent article 10 or the predetermined time period for at least 24 hours; and the changing schedule outputting unit 91 presents a daily changing schedule for changing the absorbent article.

Further, in the present first embodiment, the changeable time storage unit 521 preferably stores a plurality of changeable time instants that can serve as candidates for changing time instants for changing the absorbent article. The changing schedule computation unit 81 performs computation for finding a total urination amount for each of a plurality of predetermined time periods each being defined by the plurality of changeable time instants that are stored, and selecting, from the plurality of types of the absorbent articles 10, the absorbent article 10 to be used in each of the plurality of predetermined time periods.

The data acquisition unit 41 acquires data on the amount of change in impedance measured over time by the urination sensor 20. In the present first embodiment, the impedance-change amount corresponds to voltage data outputted to the data logger 32 in the aforementioned data collection unit 30, and also corresponds to the amount of urine absorbed by the absorbent article 10 at various time instants, i.e., the urine absorption amount. Changes-over-time in impedance are supplied, as impedance-change-amount data, from the data collection unit 30's data logger 32 to the urination data computation unit 51 through the data acquisition unit 41.

A urination detection unit 512 detects urination timing—i.e., the urination time instant—from a change in impedance. More specifically, the urination detection unit 512 determines whether the measured impedance change is caused by urination or by noise. In cases where it is detected that the change is caused by urination, the urination data computation unit 51 supplies information indicating the time instant at which urination was detected to a urination-time-instant computation unit 511, and supplies the impedance-change amount to a urine-absorption-amount computation unit 513.

In order to determine the urine absorption amount accurately, it is preferable to provide an acceleration sensor to the data collection unit 30, thereby making it possible to detect the inclination of the diaper with the acceleration sensor and correct the impedance-change-amount data on the basis of the detected diaper inclination.

On the basis of the change-over-time in impedance caused by wetting/spreading of urine in the absorbent article 10 as measured by the urination sensor 20 attached to the absorbent article 10, the urination data computation unit 51 computes the urine absorption amount of the absorbent article 10, i.e., the urine absorption amount absorbed by the absorbent member 11c as a result of the wearer's urination. In the present first embodiment, the urine-absorption-amount data computed by the urination data computation unit 51 is transmitted to the urination data storage unit 70 to be stored together with the urination time instant data.

In the present first embodiment, the urination data storage unit 70 of the care schedule proposal device 1 stores, together with urination time instant data, the wearer's urination amount data as acquired from the urine absorption amount of the absorbent article that absorbs urine. The urination data computation unit 51 includes a urination-time-instant computation unit 511 and a urine-absorption-amount computation unit 513 (see FIG. 7). As described above, in the present embodiment, the urination data storage unit 70 acquires and stores the urine absorption amount of the absorbent article 10 on the basis of changes-over-time in impedance caused by wetting/spreading of urine in the absorbent article 10. "Urination data" refers to data about the urination time instant when the wearer urinated and the urination amount; the urination data storage unit 70, however, does not need to directly store these two pieces of information. Data only needs to be in a form from which these two pieces of information can be found. For example, the data may be an impedance-change amount and the time instant when the impedance change occurred.

As illustrated in FIG. 7, the urination data storage unit 70 includes: a urination-time-instant accumulation table 72 that stores, for each wearer, urination time instants which are computation results of the urination-time-instant computation unit 511; and a urine-absorption-amount accumulation table 73 that stores, for each wearer, urine absorption amounts which are computation results of the urine-absorption-amount computation unit 513. In the present first embodiment, the urine-absorption-amount accumulation table 73 is configured such that the urination amount is reset to zero when the urine absorption pad 11, i.e., the absorbent article 10, is changed. More specifically, when the data collection unit 30 is removed from the terminal portions 24a, 24b of the urination sensor 20 including the electrode groups, the discontinuation of voltage application between the electrodes by the impedance detection unit 31 is detected, and, in the urine-absorption-amount accumulation table 73, the accumulation data on the urination amount, i.e., the urine absorption amount, is reset to zero. The information in the urination-time-instant accumulation table 72 and the urine-absorption-amount accumulation table 73 is converted into urination time instants and urination amounts, and is stored in a urination schedule table 75 before being reset to zero.

More specifically, in the present first embodiment, the data in the urination-time-instant accumulation table 72 and the urine-absorption-amount accumulation table 73 are computed in a data form wherein the urination amount and the urination time instant constitute a pair so that the data can be used directly for schedule computation, and are stored in a urination data area (not illustrated) in the urination schedule table 75. As described above, this computation and storage are performed immediately before resetting the urination-time-instant accumulation table 72 and the urine-absorption-amount accumulation table 73 to zero. Note, however, that it is possible to directly find the total urination amount within a predetermined time period from the urination time instant and the urine absorption amount stored in the urination-time-instant accumulation table 72 and the urine-absorption-amount accumulation table 73, without providing a urination data area in the urination schedule table 75.

The absorbent-article changing-time-instant storage unit 521 stores intended absorbent-article changing time instants at which a caregiver etc. changes the absorbent article 10. More specifically, the absorbent-article changing-time-instant storage unit 521 stores intended absorbent-article changing time instants which are inputted by, for example, a caregiver through the keyboard. A predetermined-time-period determination unit 522 selects, for example, two nearby intended absorbent-article changing time instants as time instants for defining a predetermined time period, and stores them in the urination schedule table 75.

In the present first embodiment, a predetermined time period of the invention for which a total urination amount is to be found is determined in advance before performing schedule computation, as described above, and a suitable absorbent article 10 is found for each predetermined time period that has been determined.

The total-urine-absorption-amount computation unit 523 calculates the total urination amount within each predetermined time period, such as the first time period. The "total urination amount" refers to the total urine absorption amount within a predetermined time period, or the total amount of urination voided to an absorbent article 10 worn within that predetermined time period—i.e., the accumulation amount of urination, or total urination amount, voided within that predetermined time period. For example, in a case where the first time period is from 9 a.m. to 1 p.m. and a wearer urinates 50 mL at 9:30 a.m., 70 mL at 10 a.m., and 30 mL at 12 noon, the total urination amount within the first time period is 150 mL. The total-urine-absorption-amount computation unit 523 finds the total urination amount within each predetermined time period from the urination schedule table 75 storing the urination time instants and urination amounts, and stores the total urination amount in a total urination amount area in the urination schedule table 75. Note that, in the present first embodiment, in cases where urination data for a plurality of days are stored in the urination data storage unit 70, a process is executed wherein the maximum-urine-absorption-amount acquisition unit 524 is activated as described further below, and a maximum value, among the total urination amounts within the same predetermined time period across the plurality of days, is stored in the urination schedule table 75 as the total urination amount for that predetermined time period.

In the present first embodiment, the absorbent article information table 76, which serves as the absorbent article information storage unit constituting the care schedule proposal device 1, stores information about various types of absorbent articles together with their respective urine absorption capacities.

Herein, "urine absorption capacity" refers to the maximum absorption amount of an absorbent article. In the present first embodiment, in cases where there is a value determined for a product, such as in cases where an absorption capacity determined by a manufacturer is described on the packaging or instruction leaflet of a commercially-available absorbent article, then that value is employed as the urine absorption capacity.

Other than the types of absorbent articles and their absorption capacities, examples of information on absorbent articles stored in the absorbent article information table 76, which serves as the absorbent article information storage unit, include: the types and sizes of absorbent articles such as urine absorption pads and diapers; and the types and sizes of outer members (for example, diapers or cloth underpants to be worn outside urine absorption pads) to be arranged on the non-skin-facing surface side of a urine absorption pad in a worn state. Examples of information on the types of absorbent articles include information on further subclassification, such as whether the diaper is a tape-fastening diaper or a pull-on diaper. The information on the absorbent articles may be updated as required via network channels.

In the present first embodiment, the absorbent-article changing-time-instant storage unit 521 constituting the care schedule proposal device 1 stores time instants for changing absorbent articles. The absorbent-article changing-time-instant storage unit 521 stores, for example, time instants for performing tasks for changing absorbent articles, which are inputted through an input unit, such as a keyboard, by a caregiver etc. The intended absorbent-article changing time instant may be a discretionary time instant that is set by being inputted by a caregiver etc. by using an input unit such as a keyboard. For example, in cases where absorbent articles are to be changed a plurality of times a day, such as at 9 a.m., 1 p.m., 4 p.m. and 7 p.m., then 9 a.m., which is for changing the absorbent article for the first time, is stored as the first changing time instant, 1 p.m. for changing the absorbent article for the second time is stored as the second changing time instant, 4 p.m. for changing the absorbent article for the third time is stored as the third changing time instant, and 7 p.m. for changing the absorbent article for the fourth time is stored as the fourth changing time instant. It should be noted that the absorbent article does not necessarily have to be actually changed exactly at the intended absorbent-article changing time instant, and may be slightly before or after the intended absorbent-article changing time instant. For example, the absorbent article may be changed within 10 minutes before or after the intended absorbent-article changing time instant.

In the present first embodiment, the care schedule proposal device 1 includes a predetermined-time-period determination unit 522 that finds a predetermined time period from the time instants stored in the absorbent-article changing-time-instant storage unit 521. The predetermined-time-period determination unit 522 determines, as the predetermined time period, a time period between an intended absorbent-article changing time instant stored in the absorbent-article changing-time-instant storage unit 521 and an absorbent-article changing time instant at which the absorbent article is to be changed the next time. However, the predetermined time period, which is determined by the predetermined-time-period determination unit 522, does not have to be determined at the stage of acquiring the urination data.

As described above, the predetermined-time-period determination unit 522 determines, as the predetermined time period, a time period between an intended absorbent-article changing time instant stored in the absorbent-article changing-time-instant storage unit 521 and an intended absorbent-article changing time instant at which the absorbent article is to be changed the next time. For example, the time period from the first changing time instant to the second changing time instant is a time period in which the wearer is wearing an absorbent article changed the first time, and this time period is determined as the first time period. Similarly, the time period from the second changing time instant to the third changing time instant is determined as the second time period, the time period from the third changing time instant to the fourth changing time instant is determined as the third time period, and the time period from the fourth changing time instant to the first changing time instant of the next day is determined as the fourth time period. The predetermined-time-period determination unit 522 stores the predetermined time periods that have been determined in the urination schedule table 75.

In the present first embodiment, the changing schedule computation unit 81 in the changing schedule proposal unit 90 includes: a total-urination-amount computation unit 525 constituted by the total-urine-absorption-amount computation unit 523 and the maximum-urine-absorption-amount acquisition unit 524; and an absorbent article selection unit 63 (see FIG. 7). The total-urine-absorption-amount computation unit 523 calculates the total urination amount, which is the total of urine absorption amounts within each predetermined time period. The "total urination amount" refers to the total of urine absorption amounts within a predetermined time period, or the total amount of urination voided to an absorbent article worn within that predetermined time period—i.e., the accumulation amount of urination within that predetermined time period. More specifically, the total-urine-absorption-amount computation unit 523 calculates the total urination amount within a predetermined time period defined by two time instants corresponding to the data collection start time and the data collection end time that are selected from changing time instants (intended changing time instants) which are an example of the changeable time instants or changeable time periods stored in the absorbent-article changing-time-instant storage unit 521 serving as the changeable time storage unit. For example, in a case where the first time period is from 9 a.m. to 1 p.m. and a wearer urinates 50 mL at 9:30 a.m., 70 mL at 10 a.m., and 30 mL at 12 noon, the total urination amount within the first time period is 150 mL. The total-urination-amount computation unit 525 finds the total urination amount within each predetermined time period from the urination schedule table 75 storing the urination time instants and urination amounts, and stores the total urination amount in a predetermined region in the urination schedule table 75.

In the present first embodiment, the absorbent article selection unit 63 in the changing schedule computation unit 81 performs computation for selecting and specifying a preferred absorbent article to be used within the predetermined time period by selecting an absorbent article having an absorption capacity that is greater than and near the total urination amount, from among information on the absorbent articles stored in the absorbent article information table 76. An absorbent article "having an absorption capacity that is greater than and near the total urination amount" refers to an absorbent article whose absorption capacity is greater than the total urination amount, and whose absorption capacity is the smallest (nearest) among the absorbent articles. For example, in cases where the absorbent article information table 76 stores information on an absorbent article A with an absorption capacity of 300 mL, an absorbent article B with 600 mL, an absorbent article C with 900 mL, an absorbent article D with 1200 mL, an absorbent article E with 1500 mL, and an absorbent article F with 1800 mL, if the total urination amount within the first time period is 600 mL, then the absorbent article selection unit 63 selects absorbent article C—whose absorption capacity is the smallest among the absorbent articles C to F having absorption capacities greater than 600 mL—as the absorbent article for the first time period. If the total urination amount within the second time period is 1000 mL, the absorbent article selection unit 63 selects absorbent article D—whose absorption capacity is the smallest among the absorbent articles D to F having absorption capacities greater than 1000 mL—as the absorbent article for the second time period. In the present first embodiment, schedule computation is performed for a day, i.e., for 24 hours, to find the absorbent articles to be used.

The changing schedule outputting unit 91 in the changing schedule proposal unit 90 outputs information on the absorbent articles selected by the absorbent article selection unit 63. In the present first embodiment, the care schedule proposal device 1 outputs information on the absorbent articles selected by the absorbent article selection unit 63 to the display unit 80 of the information processing device 100. As described above, in the present first embodiment, the result of schedule computation performed for a day, i.e., 24 hours, is displayed in the following manner. More specifically, as illustrated, for example, in FIG. 8(a), the display unit 80 displays and presents information that proposes the use of: the absorbent article B within the first time period, i.e., the time period from 9 a.m. to 1 p.m.; the absorbent article A within the second time period, i.e., the time period from 1 p.m. to 4 p.m.; the absorbent article C within the third time period, i.e., the time period from 4 p.m. to 7 p.m.; and the absorbent article E within the fourth time period, i.e., the time period from 7 p.m. to 9 a.m. the next morning. Instead of displaying the names of the types of the absorbent articles and the respective absorption capacities as illustrated in FIG. 8(a), the information on the absorbent articles outputted by the changing schedule outputting unit 91 may be letters, symbols, or colors that indicate, in a stepwise manner, the respective absorption capacities of the absorbent articles 10. For example, as illustrated in FIG. 8(b), the absorption capacities of the absorbent articles A to F may be displayed as small, medium-small, medium, medium-large, large, and extra large in the order from small to large.

Based on the information outputted and presented by the changing schedule outputting unit 91, a caregiver etc. can use the preferred absorbent article having an absorbency corresponding to the urination amount within each predetermined time period.

With the care schedule proposal system 1S and the absorbent article proposal device (care schedule proposal device) 1 of the present first embodiment, it is possible to select and use an absorbent article for use in a hospital, a nursing-care facility, or the like, that is capable of absorbing the urination amount within each predetermined time period and that has an absorbency that does not greatly exceed the urination amount—i.e., an absorbent article having an absorbency corresponding to the urination amount within each predetermined time period. The urination amount of a care-receiver within each predetermined time period differs for each care-receiver, and thus, it is possible to use an absorbent article corresponding to the urination amount of each care-receiver. Thus, leakage of urine—which may occur if the absorption capacity is small—can be suppressed effectively, thereby being able to reduce the burden on the caregiver. Further, the use of an absorbent article having an unnecessarily large absorption capacity can be prevented, thereby being able to reduce care costs.

From the viewpoint of proposing an absorbent article further matching the urination amount of a care-receiver, in the present first embodiment, the changing schedule computation unit 81 includes a maximum-urine-absorption-amount acquisition unit 524 that determines the maximum value among total urination amounts within a certain predetermined time period across a plurality of days. The maximum-urine-absorption-amount acquisition unit 524 stores the maximum value among total urination amounts within the predetermined time period across a plurality of days, together with a plurality of days' worth of urination data of a wearer of an absorbent article. The absorbent article selection unit 63 of the changing schedule computation unit 81 is configured to select an absorbent article having a greater absorption capacity than the maximum value among total urination amounts within the predetermined time period across a plurality of days. As illustrated in FIG. 7, the care schedule proposal device 1 constituting the care schedule proposal system 1S of the present first embodiment is capable of: acquiring a plurality of days' worth of the wearer's urination data; on the basis of the data, finding the maximum value among total urination amounts within a certain predetermined time period across a plurality of days; and proposing an absorbent article having a larger absorption capacity than the maximum value. The maximum-urine-absorption-amount acquisition unit 524 determines the maximum value among total urination amounts within a certain predetermined time period across a plurality of days, which are stored in the urination schedule table 75.

More specifically, in the present first embodiment, the urination data storage unit 70 stores a plurality of days' worth of the wearer's urination amount data; and the plurality of days' worth of the urination amount data stored in the urination data storage unit 70 can be transmitted to the urination schedule table 75, and be stored in a urination data area (not illustrated) of the urination schedule table 75. In cases where there are a plurality of days' worth of urination data, the changing schedule computation unit 81 activates the maximum-urine-absorption-amount acquisition unit 524 instead of the total-urine-absorption-amount computation unit 523; and, from the urination data at one or a plurality of urination time instants in each of the plurality of predetermined time periods, each time period being set from a data collection start time to a data collection end time, the maximum total urination amount is determined from among total urination amounts found over a plurality of days within each predetermined time period, and the maximum total urination amount that has been determined is stored in the urination schedule table 75 as the total urination amount of that predetermined time period. Further, the changing schedule computation unit 81 performs computation so as to: compare the total urination amount stored in the urination schedule table 75 with the urine absorption capacity of one or a plurality of types of absorbent articles selected from the plurality of types of absorbent articles stored in the absorbent article information storage unit 76; and specify each of the plurality of predetermined time periods and one or a plurality of types of absorbent articles to be selected, in a manner that the absorption capacity of each selected absorbent article does not fall below the maximum total urination amount calculated for each predetermined time period. Thus, in the present first embodiment, the urination data storage unit 70 stores a plurality of days' worth of the wearer's urination amount data; and the changing schedule computation unit 81 performs computation for determining at least either the absorbent article or the predetermined time period by employing a maximum total urination amount, among total urination amounts found over the plurality of days within the predetermined time period having been set, as the total urination amount within that predetermined time period.

A method for calculating the aforementioned maximum total urination amount is described in detail by using Table 1. Table 1 below is an example illustrating total urination amounts within each predetermined time period of a wearer who used absorbent articles, having the urination sensor 20 attached thereto, for three days. If the total urination amount within the first time period on the first day of using the absorbent article is 150 mL, the total urination amount within the first time period on the second day is 300 mL, and the total urination amount within the first time period on the third day is 250 mL, then the maximum-urine-absorption-amount acquisition unit 524 of the changing schedule computation unit 81 determines that 300 mL, which is the total urination amount on the second day, is the maximum total urination amount within the first time period over the first to third days. Similarly for the other time periods shown in Table 1 below, the maximum-urine-absorption-amount acquisition unit 524 determines 500 mL, 700 mL, and 1200 mL, respectively, as the maximum total urination amount for the second time period, the third time period, and the fourth time period over the first to third days. Data on the maximum values of the total urination amounts within the respective predetermined time periods over the plurality of days, which have been determined by the maximum-urine-absorption-amount acquisition unit 524, are stored in the urination schedule table 75 as the respective total urination amounts for each of the predetermined time periods.

TABLE 1

|  | First time period 9:00-13:00 | Second time period 13:00-16:00 | Third time period 16:00-19:00 | Fourth time period 19:00-9:00 |
| --- | --- | --- | --- | --- |
| First day | 150 mL | 500 mL | 600 mL | 1100 mL |
| Second day | 300 mL | 300 mL | 500 mL | 1200 mL |
| Third day | 250 mL | 450 mL | 700 mL | 1000 mL |
| Maximum value of total urine absorption amount from first to third days | 300 mL | 500 mL | 700 mL | 1200 mL |

On the basis of the total urination amount data—which is the maximum total urination amount within each predetermined time period over a plurality of days—determined as above and stored in the urination schedule table 75, the absorbent article selection unit 63 selects an absorbent article having the smallest absorption capacity from among absorbent articles having a greater absorption capacity than the total urination amount. For example, if the absorbent article information table 76 stores information on absorbent articles A to F respectively having absorption capacities of 300 mL, 600 mL, 900 mL, 1200 mL, 1500 mL, and 1800 mL, then the absorbent article B is selected for the first time period over the first to third days, the absorbent article B is selected for the second time period, the absorbent article C is selected for the third time period, and the absorbent article E is selected for the fourth time period, on the basis of the total urination amounts shown in Table 1 above.

Figure 9:
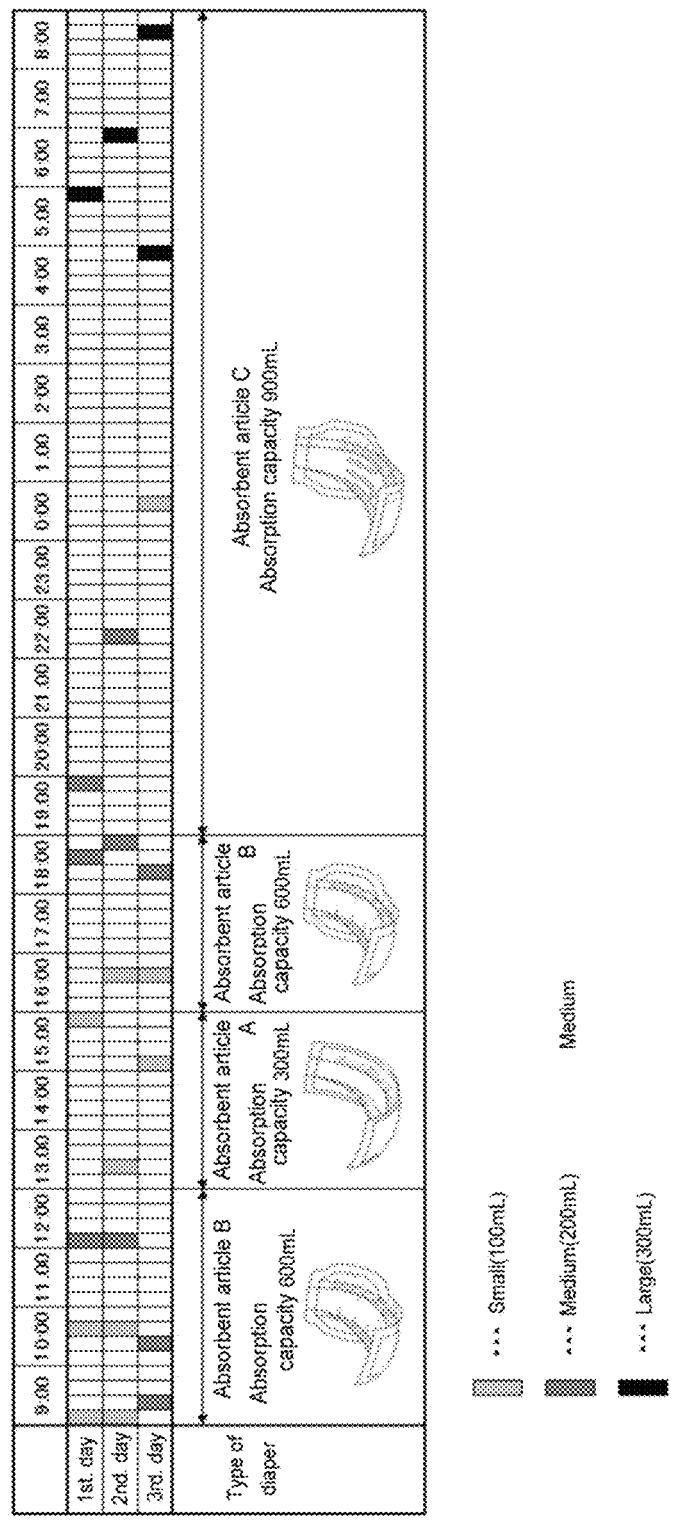
FIG. 9 is a diagram illustrating a display example of a care schedule, including absorbent article information and urination pattern data, which is outputted by the care schedule proposal system according to the first embodiment.

In the present first embodiment, the changing schedule proposal unit 90 includes a changing schedule outputting unit 91, and the changing schedule outputting unit 91 outputs information on absorbent articles selected by the absorbent article selection unit 63. The changing schedule outputting unit 91 may output data/information on the care-receiver's urination pattern together with information on the absorbent articles. The urination pattern data/information refers to data/information on urination time instants and urine absorption amounts. For example, as illustrated in FIG. 9, the urination pattern data/information may be outputted, together with information on the selected absorbent articles, to the display unit 80 etc. of the information processing device 100 serving as the care schedule proposal device 1. The urination pattern data/information illustrated in FIG. 9 illustrates the urine absorption amount per every 15 minutes in color shades corresponding to the respective amounts. More specifically, the urine absorption amounts are shown in color shades corresponding to "small", "medium" and "large", wherein 100 mL or less indicates "small", 200 mL or less indicates "medium", and 300 mL or less indicates "large". Stated differently, the darker the color, the larger the urine absorption amount, whereas the lighter the color, the smaller the urine absorption amount. For example, the total urination amount within the fourth time period from 19 p.m. to 9 a.m. is 500 mL on the first day, 500 mL on the second day, and 700 mL on the third day. In cases where the absorbent article information table 76 stores information on the absorbent articles A to F as described above, the care schedule proposal device 1 selects and proposes the absorbent article C, which has the smallest absorption capacity from among the absorbent articles C to F having absorption capacities exceeding 700 mL, since the maximum total urination amount within the fourth time period is 700 mL on the third day.

The urine absorption amounts may be indicated stepwise in color shades or colors corresponding to the respective amounts as illustrated in FIG. 9, or may be indicated stepwise with letters, symbols, etc., corresponding to the respective urine absorption amounts.

From the viewpoint of further improving the accuracy of measuring the total urination amount, it is preferable that the number of days for acquiring and storing data on the wearer's urine absorption amounts for finding the total urination amount is at least one day, more preferably at least three days, and preferably at most seven days, more preferably at most five days, and preferably from one to seven days, more preferably from three to five days.

From the viewpoint of allowing a caregiver to provide care smoothly, it is preferable that the care schedule proposal device 1 includes the absorbent article information storage unit 76 storing information on absorbent articles. A caregiver etc. can store information on absorbent articles in the absorbent article information table 76 serving as the absorbent article information storage unit of the care schedule proposal device 1. Examples of the information to be stored include information during use of the absorbent articles, such as the feel upon use of the absorbent articles.

From the viewpoint of facilitating care management of the care-receiver, in the present first embodiment, the care schedule proposal device 1 preferably displays wearer information about the wearer and life information about the life of the wearer, in addition to the information on the absorbent articles. A database including the aforementioned urination schedule table 75 etc. includes: a wearer information table 78 in which the wearer information is accumulated; and a life information table 77 in which the life information is accumulated. The wearer information table 78 stores the wearer information provided from a wearer information storage unit 83, and the life information table 77 stores the life information inputted by the life information storage unit 82. The wearer information and the life information are mainly provided to the wearer information storage unit 83 and the life information storage unit 82 by a caregiver etc. by using an input unit such as a keyboard.

Examples of the wearer information include the gender, age, height and weight of the wearer, the degree of care necessary, and the bed number and/or room number (hospital room number) of the wearer. Examples of the life information include: information on health, such as body temperature, blood pressure, and pulse count; information on feelings, such as happiness, anger, and sadness; information on defecation, such as whether or not there was defecation in the toilet or on the urine absorption pad, diaper, cloth underpants, etc., fecal condition, fecal amount, and defecation time instant; information on urination, such as whether or not there was urination in the toilet, urine condition, urination amount, and urination time instant; information such as whether or not there was urination on the diaper or urine absorption pad, weight of urine absorption pad measured with a balance scale etc., weight or urine amount of urine absorption pad including urine etc., and urinary condition; information on condition, amount, etc., of residual urine; information on the time instant of performing urinary catheterization and amount, condition, etc., of urine; leakage information, such as whether or not there was leakage of urine, feces, etc., from the urine absorption pad, diaper, cloth underpants, etc., and the amount of leakage of urine, feces, etc.; bathing information, such as whether or not bathing/foot bathing was performed, the time instant and time length that bathing was performed, and the time it took for bathing/foot bathing; meal information, such as the time instants and time lengths of meals, the amount and types of meals, and moisture content; beverage information, such as the time instants of intake of beverages such as drinking water, and the amount and types of beverages; water intake information, such as the amount and time instants of water intake; drip injection information, such as the time instants of performing drip injection and the types and amount of the drip; sleep information, such as the time instant of going to bed, the time instant of going to sleep, the time instant of falling asleep, the time instant of waking up, the hours in bed, and the hours of sleep; information on body movement etc.; activity status, such as the time instants, time lengths and types of activities performed for maintaining/improving activity and cognitive functions, such as rehabilitation and recreation; visitation situation information, such as the time instants and time lengths of visitations, and visitors; information on environmental temperature, humidity, etc.; information on the date and time the aforementioned life information was recorded; and the date and time recording was terminated.

From the viewpoint of sharing the care-receiver's urination pattern data among caregivers and caring for the care-receiver more appropriately, it is preferable that the care schedule proposal device 1 is configured so as to be able to display, on the display unit 80 etc. of the care schedule proposal device 1, at least one of information on the urination time instant, urine absorption amount (urination amount), total urination amount, a predetermined time period over a plurality of days, and the maximum total urination amount, absorbent article information, wearer information, and life information, which are stored in the database unit.

In the present first embodiment, the changing schedule outputting unit 91 makes the display unit 80 display the product names, product numbers, images, etc., of absorbent articles, to output information on the absorbent articles selected by the absorbent article selection unit 63. However, outputting can be achieved by lighting-up light-emitting elements having different colors for the different types of absorbent articles. An example of a light-emitting element is an LED. Also, outputting may be achieved by outputting an alarm sound or a voice guide with a sound generating device such as a speaker. As described above, for the implementation for outputting absorbent article information by the changing schedule outputting unit 91, it is possible to employ visual implementations such as images, letters, or light emission; also, absorbent article information can be outputted by auditory implementations such as voice, or a combination of visual and auditory implementations. Other than visual and auditory implementations, other discretionary implementations recognizable by a user of the care schedule proposal device 1 of the invention can be employed, such as tactile implementations by vibration, for example.

In the present first embodiment, the care schedule proposal device 1 may be configured in a manner that an absorbent article selected from the absorbent articles stored in the absorbent article information table 76, which is the absorbent article information storage unit, is displayed on an order information inputting screen on the display unit 80, so that the absorbent article can be purchased. An example may be a configuration wherein the care schedule proposal device 1 accesses, through a network channel, a webpage creating the order information inputting screen at the timing that the changing schedule outputting unit 91 outputs the absorbent article information to the display unit 80, to make the display unit 80 display the webpage. Note that the timing for outputting information for ordering the selected absorbent article may be a discretionary timing other than the timing of outputting the absorbent article information. An orderer can input order information through the order information inputting screen, and place an order for the absorbent article. Examples of order information include the address, name, age, gender, phone number, and email address of the orderer, the number of times ordered, the date of order, the product name of the absorbent article, the number of absorbent articles to be ordered, and destination.

The care schedule proposal system 1S of the present first embodiment can be used with the aim of proposing, to a caregiver, an absorbent article and/or a changing time instant suitable for each wearer in, for example, a nursing-care facility or an ordinary household, by acquiring urination information related to the care-receiver's urination amount and urination time instant by using a urination sensor 20 attached to the absorbent article absorbing urine.

A modified example of the care schedule proposal system 1S of the present first embodiment will be described. In this modified example of the care schedule proposal system 1S of the present first embodiment, the urination data computation unit 51 may acquire data on changes in impedance as measured by the urination sensor 20, calculate the urine absorption amount based on the data, and store the urine absorption amount in the urine-absorption-amount accumulation table 73 of the urination data storage unit 70 as urination amount data as in the foregoing first embodiment, but instead may calculate the urine absorption amount based on the weight (1) of the absorbent article before urine absorption and the weight (2) of the absorbent article having absorbed urine etc., and store the urine absorption amount in the urination data storage unit 70 as urination amount data. In this case, the urination data storage unit 70 finds, as the urine absorption amount, the difference by subtracting the weight (1) from the weight (2), and stores the urine absorption amount in the urine-absorption-amount accumulation table 73 of the urination data storage unit 70. The weights (1) and (2) can be measured with a known measurement means, such as a balance scale, which is separate from the care schedule proposal device 1. On the basis of information inputted by an operator, such as a caregiver, through an input unit, such as a keyboard, the urination data computation unit 51 acquires the weights (1) and (2). In cases of calculating the urine absorption amount based on the weight of the absorbent article as described above, it is possible to use an absorbent article not equipped with a urination sensor 20.

Further, for example, the system may be configured in a manner that: the urination data computation unit 51 calculates the urine absorption amounts at a plurality of timings from the changes in impedance measured over time for a day; then the changing schedule computation unit 81 finds the total urination amount within a predetermined time period from an absorbent-article changing time instant to the next changing time instant; and, on the basis of the quantity of the total urination amount, a predetermined-time determination unit of the changing schedule computation unit 81 shifts the end time instant of the time period, i.e., the absorbent-article changing time instant. In this way, the absorbent-article changing time instant can be set in accordance with the actual measurement value of the urine absorption amount, so as to match the absorption capacity of the absorbent article being used.

More specifically, in the modified example of the present first embodiment, the changing schedule computation unit 81 can perform computation for finding the predetermined time period in which the urine absorption capacity of the absorbent article does not fall below the total urination amount, by altering the wearing-start candidate time instant or the wearing-end candidate time instant while referring to the absorbent-article changing-time-instant storage unit 521 which is the changeable time storage unit.

Further, in the modified example of the present first embodiment, the data collection start time and the data collection end time, which serve as guides for the absorbent-article changing time, can be set discretionarily by a user, such as a caregiver. The changing schedule computation unit 81 may calculate the total urination amount within each predetermined time period from the urination data at one or a plurality of urination time instants within each of the plurality of predetermined time periods from the data collection start time to the data collection end time which have been set by the user. Further, the changing schedule computation unit 81 may: compare each calculated total urination amount with the urine absorption capacity of one or more types of absorbent articles selected from the plurality of types of absorbent articles stored in the absorbent article information storage unit 76; and specify an absorbent article in which the urine absorption capacity of the selected absorbent article is not below each calculated total urination amount and the urine absorption capacity is nearest to the total urination amount. The changing schedule outputting unit 91 can present a daily absorbent-article changing schedule, together with the types of specified absorbent articles, by employing, as guides for the absorbent-article changing timings, the data collection start time or the data collection end time for each of the plurality of predetermined time periods, which has been specified by the user in the changing schedule computation unit 81.

Further, for example: the urination data computation unit 51 may calculate the urine absorption amounts at a plurality of timings from the changes in impedance measured over time for a day; then the changing schedule computation unit 81 may find the total urination amount within a predetermined time period from an absorbent-article changing time instant to the next changing time instant; and, on the basis of the quantity of the total urination amount, the absorbent article selection unit 63 of the changing schedule computation unit 81 may select an absorbent article having an absorption capacity that is greater than and near the total urination amount. In this way, it is possible to set an absorbent article having an absorption capacity corresponding to the actual measurement value of the urine absorption amount, in accordance with the absorbent-article changing time instant having been set.

Further, in the modified example of the present first embodiment, the changing schedule computation unit 81 preferably includes an absorbent article limitation means (not illustrated) that limits absorbent articles that can be selected. For example, if there is a type of absorbent article that is out of stock among a plurality of types of absorbent articles, then, by letting an operator input this fact or by causing an inventory management system etc. to notify this fact to the care schedule proposal device 1, it is possible to limit the absorbent articles to be used for computation to the articles that are in stock. Stated differently, it is preferable that the changing schedule computation unit 81 includes an absorbent article limitation means that limits absorbent articles to be used for computation; and the changing schedule computation unit 81 can thereby perform computation for determining the predetermined time period by using the urine absorption capacities of the absorbent articles having been limited by the absorbent article limitation means.

In the present first embodiment, the urination data is acquired by using one absorbent article 10 per each predetermined time period. As a modified example, the urination data computation unit 51 may acquire the urination data for a plurality of absorbent articles 10 used in a plurality of predetermined time periods, and may calculate urine absorption amounts at a plurality of timings from the changes in impedance measured over time by the respective urination sensors 20 attached to the plurality of absorbent articles 10. Further, the number of absorbent articles 10 used for acquiring the urination data is not particularly limited, either in cases of measuring the urine absorption amount after setting the predetermined time period or in cases of setting the predetermined time period after measuring the urine absorption amount. In cases where a plurality of absorbent articles 10 are used for acquiring the urination data in a single predetermined time period, the total urination amount is the total of the urine absorption amounts found by using the plurality of absorbent articles 10. From the viewpoint of improving the accuracy of measuring the urine absorption amount, it is preferable that the time of usage of the absorbent article 10 used for acquiring the urination data is from 1 to 12 hours per absorbent article.

A care schedule proposal device 2 according to a second embodiment of the present invention is described below with reference to FIGS. 10 to 13. In the present second embodiment, the urination data is prepared separately in advance, and the system is constituted only by the care schedule proposal device 2 illustrated in FIG. 10, which does not include a urination sensor and a data acquisition unit for acquiring data from the urination sensor. Like the care schedule proposal device 1 constituting the care schedule proposal system 1S of the foregoing first embodiment, the care schedule proposal device 2 of the present second embodiment can be achieved by installing predetermined programs to a general-purpose information processing device such as a personal computer.

Figure 10:
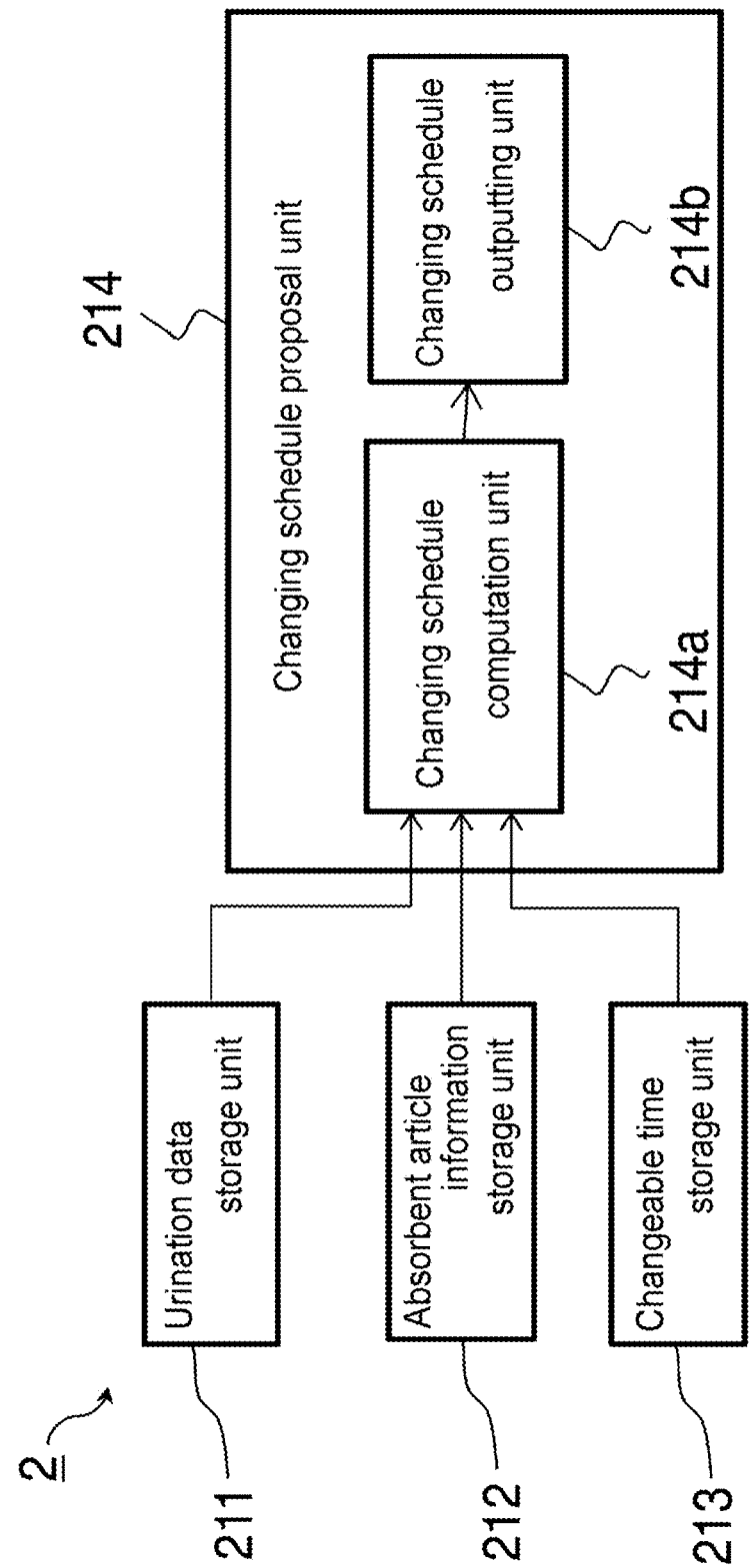
FIG. 10 is a block diagram describing a care schedule proposal device according to a second embodiment.

As illustrated in FIG. 10, the care schedule proposal device 2 includes: a urination data storage unit 211 for storing urination data; an absorbent article information storage unit 212 for storing information including at least a urine absorption capacity of an absorbent article which is also inputted from outside; a changeable time storage unit 213 that stores changeable time instants that can serve as candidates for changing time instants for changing the absorbent article; and a changing schedule proposal unit 214 including a changing schedule computation unit 214*a* and a changing schedule outputting unit 214*b*.

Figure 11:
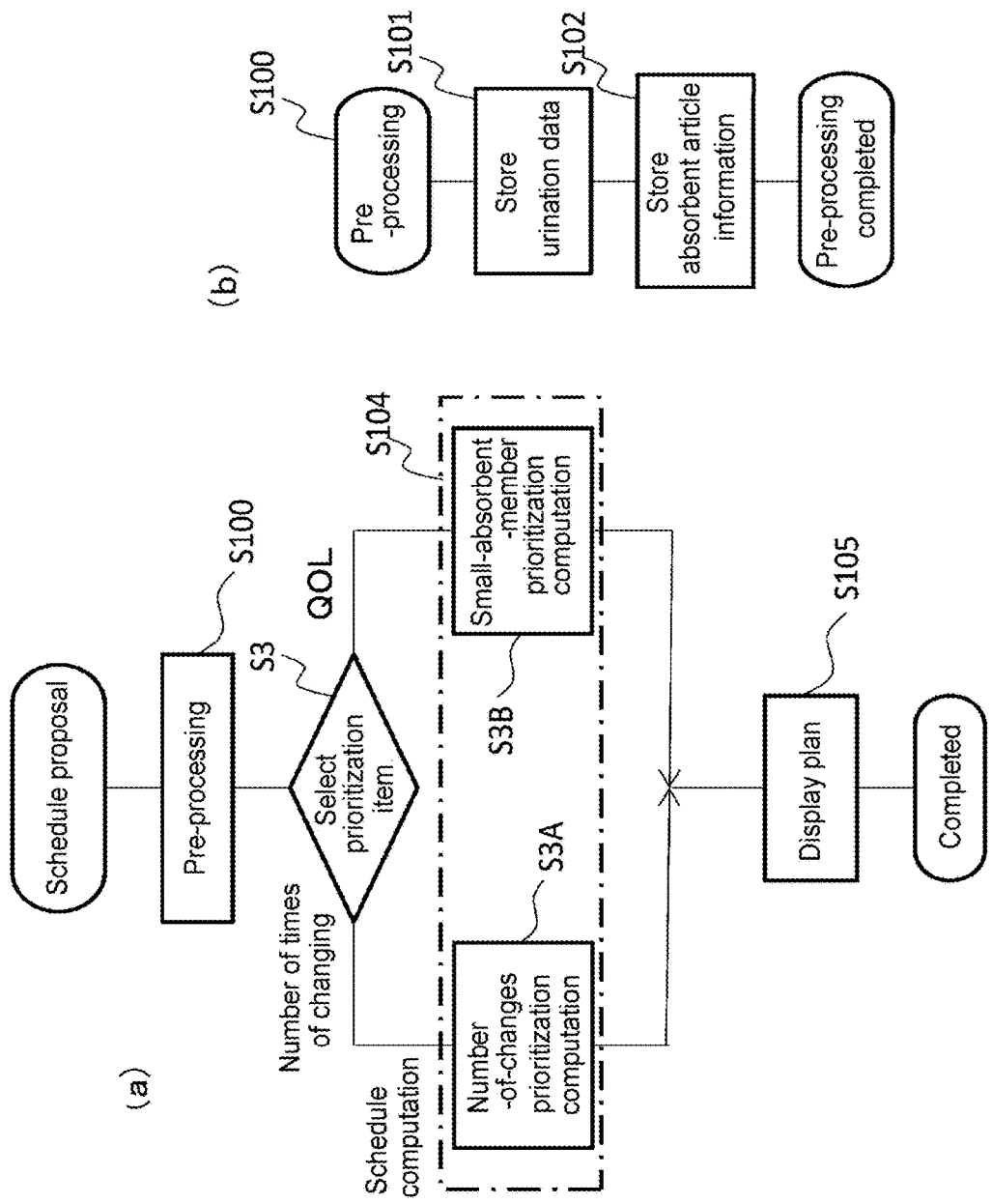
FIGS. 11(a) and 11(b) are flowcharts describing a schedule proposal flow.
Figure 12:
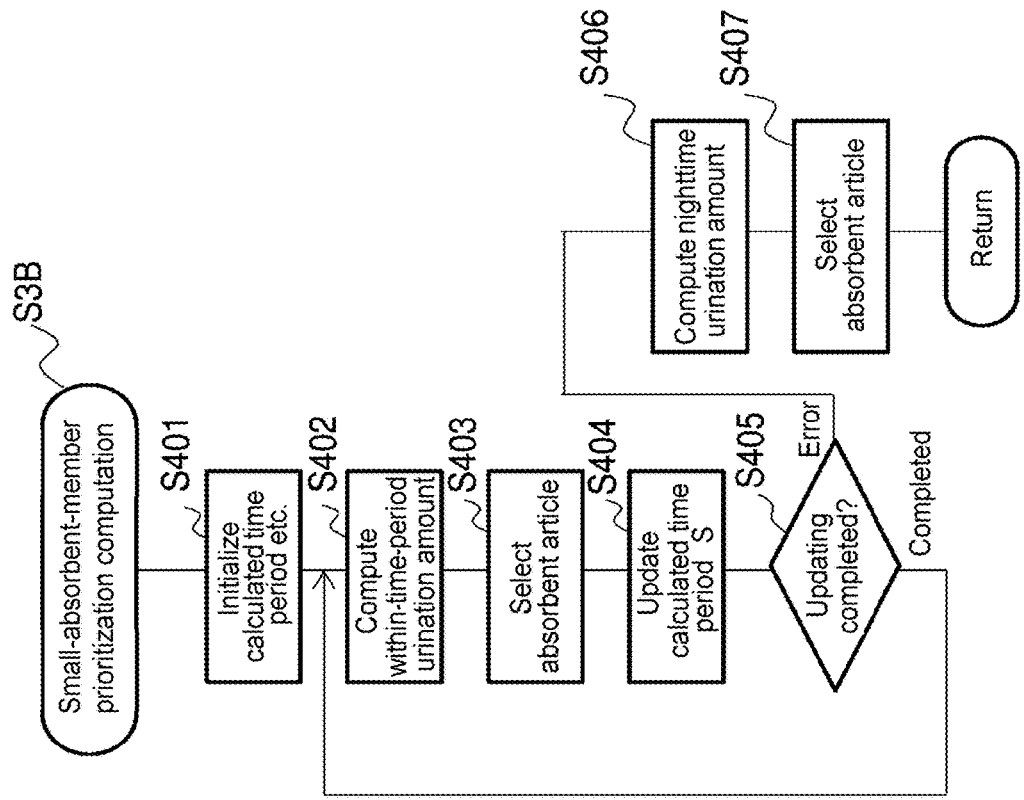
FIG. 12 is a flowchart describing small-absorbent-member prioritization computation.
Figure 13:
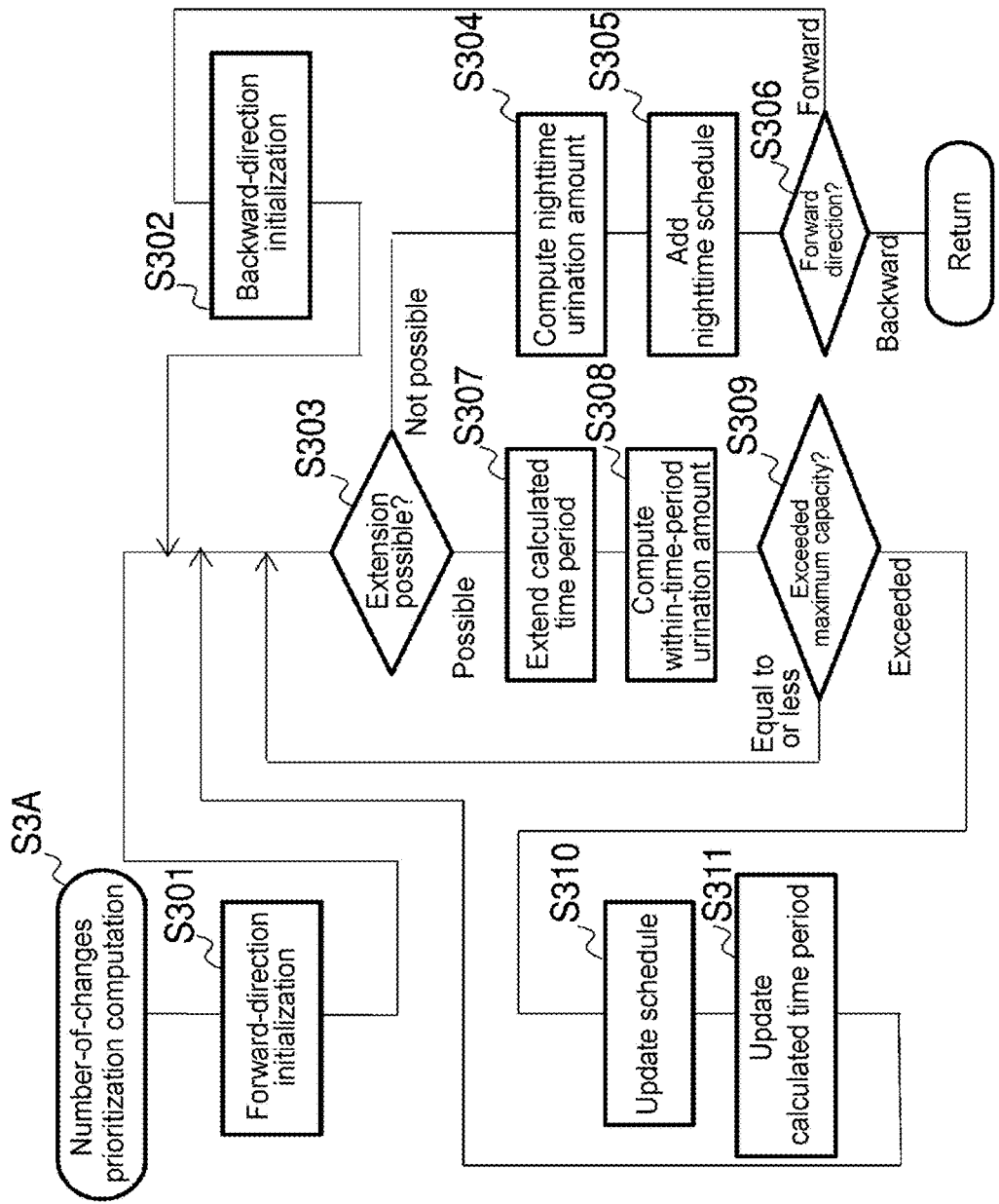
FIG. 13 is a flowchart describing number-of-changes prioritization computation.
Figure 14:
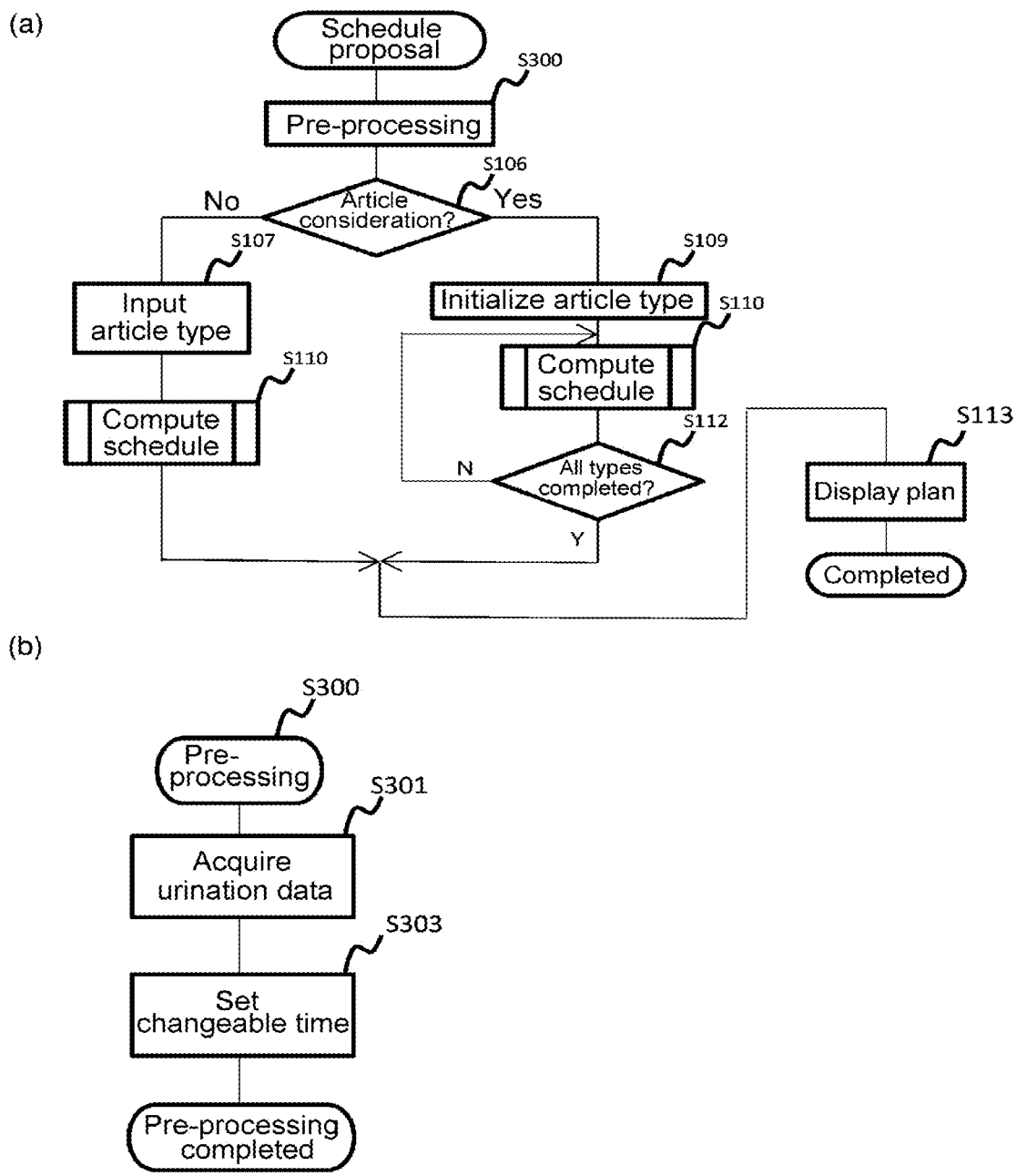
FIGS. 14(a) and 14(b) are flowcharts describing another embodiment of a schedule proposal flow.

The care schedule proposal device 2 of the present second embodiment operates according to the schedule proposal flow illustrated in FIGS. 11 to 13, and is thereby capable of executing a care schedule proposal method for proposing at least either an absorbent article to be worn or a changing time instant for changing an absorbent article, by using urination data including urination amount data and urination time instant data corresponding to the urination amount data, and urine absorption capacity data including a urine absorption capacity of an absorbent article to be used, in circumstances where there are limitations in terms of changeable time instants or changeable time periods that can serve as the changing time instant for changing the absorbent article. The flow illustrated in FIGS. 11(a) and 11(b) is an example of a care schedule proposal method for proposing, together with the type of absorbent article to be changed, a daily absorbent-article changing schedule suitable for a wearer on the basis of the wearer's urination data acquired together with the urination time instant data from the urine absorption amount of the absorbent article absorbing urine. The care schedule proposal method involves: a urination data storage step S101; an absorbent article information storage step S102; a schedule computation step S104; and a changing schedule outputting (plan displaying) step S105.

The urination data storage step S101 and the absorbent article information storage step S102 are pre-processing steps for preparing data necessary for proposing an absorbent article changing schedule. The urination data storage step S101 and the absorbent article information storage step S102 are referred to collectively as a pre-processing step S100 (see FIG. 11(b)).

In the urination data storage step S101, urination amount data (urination data) of a wearer acquired from the urine absorption amount of an absorbent article absorbing urine and urination time instant data (urination data), which have been prepared separately in advance, are stored. The urination amount data is preferably acquired, for example, by computation from impedance-change amounts measured by a urination sensor 20. Alternatively, it is possible to store urination amount data prepared by finding the urination amount by measuring the weight of a urine-including absorbent article every time the wearer urinates, and recording the urination amount together with the time instant.

In the absorbent article information storage step S102, article information including the urine absorption capacity of each of a plurality of types of absorbent articles is stored. In the present second embodiment, the absorbent article information storage step S102 is performed by writing in, to the absorbent article information storage unit 212 (see FIG. 10), data on absorbent articles acquired through a network from, for example, a database released by an absorbent article manufacturer.

In the care schedule proposal device 2 of the present second embodiment, a prioritization item selection step S3 is executed after executing the pre-processing step S100 and before executing the schedule computation step S104. The selection step S3 may be performed in accordance with an instruction inputted by an operator, or may be performed based on an instruction from an administrator through a communication channel. Inputting by an operator and instruction by an administrator are not required every time, and the device may be configured so that information for selection is stored in advance in the storage device, and the information is referenced. Depending on the selection performed at the prioritization item selection step S3, it is determined whether the computation executed at the schedule computation step S104 is a number-of-changes prioritization computation S3A or a small-absorbent-member prioritization computation S3B. When the schedule computation step S104 is completed, the changing schedule outputting step S105 is executed, wherein a care schedule is proposed by displaying, on a display unit, changing time instants and the type of absorbent article to be used at each changing time instant according to the computation result.

If the small-absorbent-member prioritization computation S3B is selected in the prioritization item selection step S3, the small-absorbent-member prioritization computation S3B is executed in the schedule computation step S104 according to the flow illustrated in FIG. 12.

In the small-absorbent-member prioritization computation S3B illustrated in FIG. 12, first, a calculated-time-period initialization step S401 is executed. In the calculated-time-period initialization step S401, all of the changing time instants recorded in the changeable time storage unit 213 (see FIG. 10) are acquired, and all of the changeable time instants are recorded as changing time instants in a schedule candidate table (also referred to as "schedule candidate") within the urination schedule table 75 (see FIG. 7). In the schedule candidate table, a period between changing time instants is recorded as a predetermined time period. The earliest changing time instant in that predetermined time period is employed as the start time instant of the time period for calculating urine amount (referred to hereinafter also as "time-period start time instant"), and the latest changing time instant in that predetermined time period is employed as the end time instant of the time period subjected to calculation (referred to hereinafter also as "time-period end time instant").

Next, a within-time-period urination-amount computation step S402 is executed. In this step, the urination amount within the time on or after the time-period start time instant and before the time-period end time instant is found as the total urination amount within that time period (referred to hereinafter also as "total urination amount") by summing up the urination amounts by referencing the urination schedule table 75. More specifically, the within-time-period urination-amount computation step S402 constitutes a total urination amount computation step of: temporarily determining a wearing-start time instant, which is one changing time instant, and a wearing-end time instant, which is a next changing time instant, from the changeable time instants or the changeable time periods stored in the changeable time storage unit 213 of the care schedule proposal device 2; and finding, from the urination data stored in the urination data storage unit 211, a total urination amount in the predetermined time period defined by the temporarily determined one changing time instant and next changing time instant. In the present second embodiment, the within-time-period urination-amount computation step S402, which is the total urination amount computation step, is executed in the schedule computation step S104.

Next, an absorbent article selection step S403 is executed. In the absorbent article selection step S403, an absorbent article having the smallest capacity among absorbent articles with absorption capacities equal to or greater than the total urination amount that has been found is selected from the absorbent article information table of the absorbent article information storage unit 212 (see FIG. 10). The selected absorbent article is recorded in the schedule candidate table in the urination schedule table 75 as the absorbent article at the time-period start time instant.

If all of the absorbent articles stored in the absorbent article information storage unit 212 have capacities below the total urination amount that has been found, then an absorbent article having the greatest capacity among the absorbent articles stored in the absorbent article information storage unit 212 is stored as a main absorbent article at the time-period start time instant, and the number of inner pads necessary is computed by using the capacity of the absorbent article and the capacity of an auxiliary absorbent article (referred to hereinafter as "inner pad") which have been stored. The computed number of inner pads is recorded in the schedule candidate table in the urination schedule table 75 after the type of absorbent article as the necessary number of inner pads at that time instant.

After the absorbent article selection step S403 is completed, a calculated-time-period updating step S404 is executed. Caution is required, as the operations in the calculated-time-period updating step S404 in the small-absorbent-member prioritization computation S3B are different from the operations in the calculated-time-period updating step S311 in the later-described number-of-changes prioritization computation S3A.

In the calculated-time-period updating step S404, the start time instant of a predetermined time period T2 is set as the time-period start time instant for the predetermined time period T2 and is also set as the time-period end time instant of the time period T1 immediately before the predetermined time period T2. Further, the next changing time instant after the time-period start time instant of the predetermined time period T2 is set as the time-period end time instant.

After the calculated-time-period updating step S404 is completed, an update-complete determination step S405 is executed. In the update-complete determination step S405, it is determined whether or not it is possible to set a time period T3 immediately after the predetermined time period T2 which has been set in the calculated-time-period updating step S404. More specifically, it is determined whether or not there is a time-period end time instant for setting the immediately-following time period T3. If there is an immediately-following time period T3, then the procedure returns to the within-time-period urination-amount computation step S402, and the steps S402 to S404 are executed for the next time period T3.

If, in the update-complete determination step S405, there is no changing time instant serving as the end time instant of the next time period T3, then the procedure proceeds to a nighttime urination amount computation step S406.

In the nighttime urination amount computation step S406, the urination amount during the night is calculated. More specifically, in the nighttime urination amount computation step S406, the total urination amount between the last changing time instant of the day and the first changing time instant of the next day is found as the nighttime urination amount.

Then, an absorbent article selection step S407 is executed by employing, as the total urination amount, the nighttime urination amount that has been found. The procedure executed in the absorbent article selection step S407 is the same as that in the aforementioned absorbent article selection step S403, and thus explanation is omitted.

When the absorbent article selection step S407 is completed, the small-absorbent-member prioritization computation S3B is completed, and the created schedule plan is presented to the caregiver in the changing schedule outputting step S105 illustrated in FIG. 11(a). Table 2 shows an example of a schedule plan created by the small-absorbent-member prioritization computation S3B, together with the urination data and the absorbent article information employed for the computation. Herein, "L+2I" in the cell of the "article used" at the changing time instant "21:30" (9:30 p.m.) indicates, in a simplified manner, that a large (L) size absorbent article is used as the main absorbent article and two auxiliary absorbent articles I (inner pads) are used in combination.

TABLE 2

| Contents of urination data storage unit | | | | | | | | | | | | | | |
|---|---|---|---|---|---|---|---|---|---|---|---|---|---|---|
| Time instant | 2:00 | 5:00 | 8:30 | 9:45 | 11:00 | 12:30 | 13:45 | 14:00 | 15:30 | 16:45 | 17:45 | 19:10 | 21:00 | 22:30 | Total |
| Amount | 200 | 350 | 150 | 200 | 150 | 200 | 200 | 100 | 200 | 150 | 100 | 200 | 150 | 150 | 2500 |
| Absorbent article information | | | | | | | | | | | | | | | |
| Article name | | L | | | M | | | S | | | Inner pad (I) | | | | |
| Capacity | | 500 | | | 300 | | | 200 | | | 100 | | | | |
| Proposed schedule | | | | | | | | | | | | | | | |
| Changing time instant | 6:00 | 9:00 | 10:45 | 13:30 | 14:30 | 16:00 | 17:30 | 19:15 | 20:00 | 21:30 | | | | | |
| Article used | S | S | L | M | S | S | M | S | S | L + 2I | | | | | |

In the present second embodiment, if the number-of-changes prioritization computation S3A is selected in the prioritization item selection step S3, then the number-of-changes prioritization computation S3A is executed according to the flow illustrated in FIG. 13. The number-of-changes prioritization computation S3A creates a changing schedule in which the number of times for changing absorbent articles is reduced while using small-as-possible absorbent articles.

If the number-of-changes prioritization computation S3A is selected in the prioritization item selection step S3, the schedule computation step S104 proposes, by the number-of-changes prioritization computation S3A, a schedule with a reduced number of times for changing absorbent articles. More specifically, if the number-of-changes prioritization computation S3A is selected, the schedule computation step S104 can make a proposal with a reduced number of times for changing absorbent articles, and not just create a schedule in which absorbent articles are changed at every intended changing time instant which are set by the changeable time storage unit 213 (see FIG. 10). By reducing the number of times for changing absorbent articles, it is not only possible to reduce the psychological burden on the care-receiver, but also reduce the burden on the caregiver. In consideration of environmental and other issues, however, it is not preferable to use a larger-than-necessary absorbent article to reduce the number of time of changing. Thus, in the present second embodiment, the number-of-changes prioritization computation S3A is performed with the aim of using an absorbent article having a small absorption capacity while reducing the number of times for changing absorbent articles.

In the number-of-changes prioritization computation S3A, a minimal number of time instants required for absorbent article changing is searched from the intended changing time instants stored in the changeable time storage unit 213. Note, however, that the result of a forward search, wherein the search is performed in the forward direction sequentially from the earliest time instant toward the later time instants, may be different from the result of a backward search, wherein the search is performed in the backward direction sequentially from the latest designated time instant toward the earlier time instants, and so, it is preferable to select the appropriate one from the two results.

So, in the present second embodiment, the minimal number of time instants required for absorbent article changing is searched in both the forward direction and backward direction, as described in detail below. It is, however, possible to propose a changing schedule with a reduced number of changes also by a configuration wherein only one of the forward or backward search is performed. Stated differently, it is possible to propose a changing schedule with a reduced number of changes, even by implementing "alteration", which is a variable indicating the searching direction and searching interval in the algorithm described below, in one direction, i.e., only in either the positive or negative direction.

As illustrated in FIG. 13, in the number-of-changes prioritization computation S3A, first, a forward-direction initialization step S301 is executed. In the forward-direction initialization step S301, a variable indicating the searching direction and searching interval is set, and the range of the predetermined time period for finding the total urination amount from the urination data is initialized. More specifically, an "alteration value", which is a parameter for gradually increasing the predetermined time in a later-described calculated-time-period extendibility determination step S303, is set to a positive value.

In the forward-direction initialization step S301, a "margin time 1" and a "margin time 2" for defining the range of a predetermined time period are both set as initial designated time instants. In a later-described within-time-period urination-amount computation step S308, the total urination amount within the predetermined time is found from the urination data; the margin time instants of the predetermined time used therein—i.e., the start time instant and the end time instant of the predetermined time—are the margin time 1 and margin time 2. When the searching direction is in the forward direction, the margin time 1 is the earliest time instant in the predetermined time, and the margin time 2 is the latest time instant in the predetermined time. When the searching direction is in the backward direction, the margin time 2 is the earliest time instant in the predetermined time, and the margin time 1 is the latest time instant in the predetermined time.

Next, a calculated-time-period extendibility determination step S303 is executed. In the calculated-time-period extendibility determination step S303, the "alteration value" is added to the "margin time 2", and the sum value is compared with the earliest time instant and the latest time instant among the intended changing time instants stored in the changeable time storage unit 213. The "alteration value" is a parameter for gradually increasing the predetermined time, and more specifically, is a discretionary value of around 10 to 30 minutes. The alteration value may be set in advance, or an operator-inputting step may be provided in the pre-processing step S100. If the aforementioned sum value is not a value between the earliest time instant and the latest time instant—i.e., if the sum value is earlier than the earliest time instant among the intended changing time instants stored in the changeable time storage unit 213 or later than the latest time instant—then it is determined that it is not possible to further extend the calculated time period, and the procedure proceeds to a nighttime urination amount computation step S304.

In the calculated-time-period extendibility determination step S303, if it is determined that it is possible to extend the calculated time period, then, in a calculated-time-period extension step S307, the sum value of the "margin time 2" and the "alteration value" as found in the calculated-time-period extendibility determination step S303 is set as a new "margin time 2", and thereby the calculated time period is extended. Stated differently, the "margin time 2" among the two time instants defining the predetermined time is gradually delayed (forward direction) or advanced (backward direction) to thereby widen the calculated time period, which is the range of the predetermined time.

Herein, in extending the calculated time period, addition of the "alteration value" is repeated until the "margin time 2" is included in an intended changing time stored in the changeable time storage unit 213.

In cases where only time instants are stored in the changeable time storage unit 213, the "margin time 1" and the "margin time 2" can be determined by referencing the changeable time storage unit 213 by using pointers. In this case, by increasing or decreasing the respective pointers by a unit value, the calculated time period can be widened within an effective range. Thus, it is not necessary to repeat the addition until the "margin time 2" is included in an intended changing time stored in the changeable time storage unit 213.

In the within-time-period urination-amount computation step S308, the total urination amount within the predetermined time period defined between the "margin time 1" and the "margin time 2" is computed by using the urination data. More specifically, the within-time-period urination-amount computation step S308 constitutes the total urination amount computation step of: temporarily determining a wearing-start time instant (margin time 1), which is one changing time instant, and a wearing-end time instant (margin time 2), which is the next changing time instant, from the changeable time instants or the changeable time periods stored in the changeable time storage unit 213 of the care schedule proposal device 2; and finding, from the urination data stored in the urination data storage unit 211, the total urination amount within the predetermined time period defined by the temporarily determined one changing time instant and next changing time instant. In the present second embodiment, the within-time-period urination-amount computation step S308, which is the total urination amount computation step, is executed in the schedule computation step S104.

Next, in a maximum capacity exceedance determination step S309, it is determined whether or not the total urination amount has exceeded the capacity of the absorbent article having the largest capacity; if the total urination amount has not exceeded the capacity, the procedure returns to the calculated-time-period extendibility determination step S303. More specifically, until it is determined that the range of the predetermined time has exceeded the range of the designated time in the calculated-time-period extendibility determination step S303 or it is determined that the total urination amount has exceeded the capacity of all of the absorbent articles in the maximum capacity exceedance determination step S309, the span of the predetermined time for calculating the total urination amount is widened gradually—more specifically, in increments of the time of the alteration value—toward the delaying side in forward searching, or toward the advancing side in backward searching. In this way, a time period is determined in which the limit of the absorbent article capacity is exceeded within the range of the designated time instants.

When a time period in which the limit of the absorbent article capacity is exceeded is found, then, in a schedule updating step S310, the time period is shortened so as not to exceed the limit of the absorbent article capacity, and the margin time 2 of the newly-determined time period is added to the schedule as a changing time instant candidate. Then, an absorbent article suitable for the urine absorption amount for the newly-determined time period is selected, and thereby an absorbent-article changing schedule is created.

More specifically, this step: extracts a changing time instant that is included in the time period immediately prior to exceeding the maximum absorption capacity of the absorbent article and that is near the "margin time 2", which is the margin on the side being extended; and newly adds the changing time instant to the schedule candidate table in the urination schedule table 75.

Then, the period between the changing time instant newly added to the schedule and the "margin time 1"—which is the non-extended fixed margin in the time period immediately prior to exceeding the maximum absorption capacity of the absorbent article—is employed as the predetermined time period, and the total urination amount is found therefor from the urination data in the urination data storage unit 211. On the basis of the total urination amount and the absorbent article information, an absorbent article having the smallest urine absorption amount is selected from among the absorbent articles whose urine absorption capacity exceeds the total urination amount. The selected absorbent article is added to the schedule plan as a wearable article candidate to be used for absorbent article changing at the changing time instant of "margin time 1" in case of forward searching, and the changing time instant of "margin time 2" in case of backward searching—i.e., the starting time instant of the predetermined time period.

Thus, in the present second embodiment, the schedule computation step S104: compares the total urination amount that has been found and the urine absorption capacity of the absorbent article; and finds at least either the predetermined time period or the absorbent article by which the urine absorption capacity does not fall below the total urination amount. Further, preferably, in the schedule computation step S104, for the absorbent article whose urine absorption capacity is to be compared with the total urination amount that has been found, searching is started from an absorbent article having the smallest urine absorption capacity, from among a plurality of types of the absorbent articles; in cases where the total urination amount is greater than the urine absorption capacity, the absorbent article is repeatedly altered until the total urination amount becomes smaller than the urine absorption capacity; and in cases where the total urination amount is smaller than the urine absorption capacity, the wearing-start time instant defining the predetermined time period and the absorbent article are proposed as the changing time instant and the absorbent article to be used for changing. Further, preferably, in the schedule computation step S104, the changing time instant for changing the absorbent article is found and proposed by altering either the one changing time instant (margin time 1) or the next changing time instant (margin time 2), to thereby search for the predetermined time period in which the urine absorption capacity of the absorbent article does not fall below the total urination amount.

When schedule updating is completed in the schedule updating step S310, the calculated-time-period updating step S311 is executed, and, in order to search for a changing time instant to be added next to the schedule, the "margin time 1", which defines the calculated time period, is updated to the most-recently-added changing time instant.

When the calculated-time-period updating process in the calculated-time-period updating step S311 is completed, the procedure returns to the calculated-time-period extendibility determination step S303. Then, the aforementioned steps S303 to S309 are repeated, in order to extend the next time period after the aforementioned calculated time period to set a new calculated time period, and also select an absorbent article suitable for the newly-set calculated time period.

If, in the calculated-time-period extendibility determination step S303, it is determined that extension of the calculated time period cannot be continued, then the procedure proceeds to the nighttime urination amount computation step S304.

In the nighttime urination amount computation step S304, the last changing time instant of the day is determined.

In the backward searching, the designated time instant added first to the schedule is the last changing time instant of the day—i.e., the latest changing time instant of the day.

In the forward searching, the period between the last changing time instant added to the schedule and the last time instant stored in the changeable time storage unit 213 is employed as the predetermined time period, and the total urination amount is found therefor from the urination data. Then, from among absorbent articles having a greater absorption capacity than the total urination amount that has been found, an absorbent article having the smallest capacity is selected and is set as the absorbent article to be used at the last changing time instant, and the last time instant stored in the changeable time storage unit 213 is set as the last changing time instant of the day.

If the total urination amount is zero—i.e., if there is no urination data between the last changing time instant in the urination schedule and the last time instant stored in the changeable time storage unit 213—then the last time instant stored in the changeable time storage unit 213 is set as the last changing time instant of the day. More specifically, a nighttime absorbent article found by using a nighttime total urination amount described below is set as the absorbent article to be used at the last changing time instant in the urination schedule.

The nighttime absorbent article is determined generally according to the following procedure.

First, a nighttime total urination amount, which is the total urination amount during the nighttime—i.e., the period from the last changing time instant of the day to the first changing time instant of the next day—is computed by using the urination data. Then, if the nighttime total urination amount is below the largest absorbent article capacity, then the absorbent article whose capacity is greater than the nighttime total urination amount and smallest among the absorbent articles is selected as the absorbent article for the last changing time instant, or the number of inner pads to be used in combination with the absorbent article having the largest capacity is found.

The changing time instant and the absorbent article found in the nighttime urination amount computation step S304 are added to the schedule plan in a nighttime schedule addition step S305.

Following the nighttime schedule addition step S305, it is determined whether or not only a schedule plan by forward searching was created. If only a schedule plan by forward searching was created, then the procedure proceeds to a backward-direction initialization step S302, and the aforementioned processes are performed according to backward searching.

When the forward searching and the backward searching are finished, the number-of-changes prioritization computation is completed, and in the changing schedule outputting step S105 illustrated in FIG. 11(a), the two schedule plans created for the forward direction and the backward direction, or one of the two schedule plans having a smaller number of changing times, are/is presented to the caregiver. An example of a schedule plan created by the number-of-changes prioritization computation S3A is shown in Table 3 together with the urination data and the absorbent article information that were employed.

TABLE 3

| Presented schedule plan | | | | | |
| --- | --- | --- | --- | --- | --- |
| Changing time instant | 6:00 | 10:45 | 13:30 | 17:30 | 21:30 |
| Absorbent member size | L | L | L | L | L |
| Number of additional inner pads | 0 | 0 | 0 | 0 | 2 |

| Contents of urination data storage unit | | | | | | | | | | | | | |
| --- | --- | --- | --- | --- | --- | --- | --- | --- | --- | --- | --- | --- | --- |
| Time instant | 2:00 | 5:00 | 8:30 | 9:45 | 11:00 | 12:30 | 13:45 | 14:00 | 15:30 | 16:45 | 17:45 | 19:10 | 21:00 | 22:30 |
| Amount | 200 | 350 | 150 | 200 | 150 | 200 | 200 | 100 | 200 | 150 | 100 | 200 | 150 | 150 |

| Absorbent article information | | | | |
| --- | --- | --- | --- | --- |
| Article name | L | M | S | Inner pad (I) |
| Capacity | 500 | 300 | 200 | 100 |

Thus, in the present second embodiment, the care schedule proposal method executed by the care schedule proposal device 2 is preferably a care schedule proposal method for proposing changing time instants for changing absorbent articles and the absorbent articles to be worn, by using at least a day's worth of urination amount data and urination time instant data corresponding to the urination amount data, the method involving: a step S401 of temporarily determining one changing time instant and the next changing time instant; a step S402 of finding the total urination amount between the two changing time instants from the urination amount data and the urination time instant data corresponding to the urination amount data; a step S403 of selecting one absorbent article and acquiring its absorption capacity; a step S403 of comparing the total urination amount with the absorption capacity; and steps S403 and S310, wherein, in cases where the total urination amount is greater than the absorption capacity, the absorbent article, or the temporarily-determined changing time instant, is repeatedly altered until the total urination amount becomes smaller than the absorption capacity, and in cases where the total urination amount is smaller than the urine absorption capacity, the earlier of the changing time instants corresponding to the aforementioned total urination amount and the absorbent article having the aforementioned absorption capacity are added to a care schedule as the changing time instant and the absorbent article to be used for changing. In this way, it is possible to determine or propose a care schedule.

In the care schedule proposal device 2 of the present second embodiment, the changing schedule computation unit 214a preferably includes an absorbent article limitation means that limits absorbent articles to be used for computation. For example, if there is a type of absorbent article that is out of stock among a plurality of types of absorbent articles, then, by letting an operator input this fact or causing an inventory management system etc. to notify this fact, it is possible to limit the absorbent articles to be used for computation to the articles that are in stock.

Further, in order to achieve the same function, it is preferable to make the inventory management system cooperate with the information on absorbent articles stored in the absorbent article information storage unit 212. In this way, if, for example, the stock amount falls below a certain amount, the information about that absorbent article can be deleted automatically from the absorbent article information storage unit 212, and the information can be restored after restocking. This can be easily understood by a person skilled in the art.

Also in the present second embodiment, as in the first embodiment, it is possible to add, to the care schedule proposal device 2: a urination sensor for measuring the spreading of urine by employing impedance; and a data acquisition unit for acquiring data from the sensor. Stated differently, it is possible to configure a care schedule proposal system including: the care schedule proposal device 2; a urination sensor for measuring the spreading of urine by employing impedance; and a data acquisition unit for acquiring data from the sensor.

Figure 17:
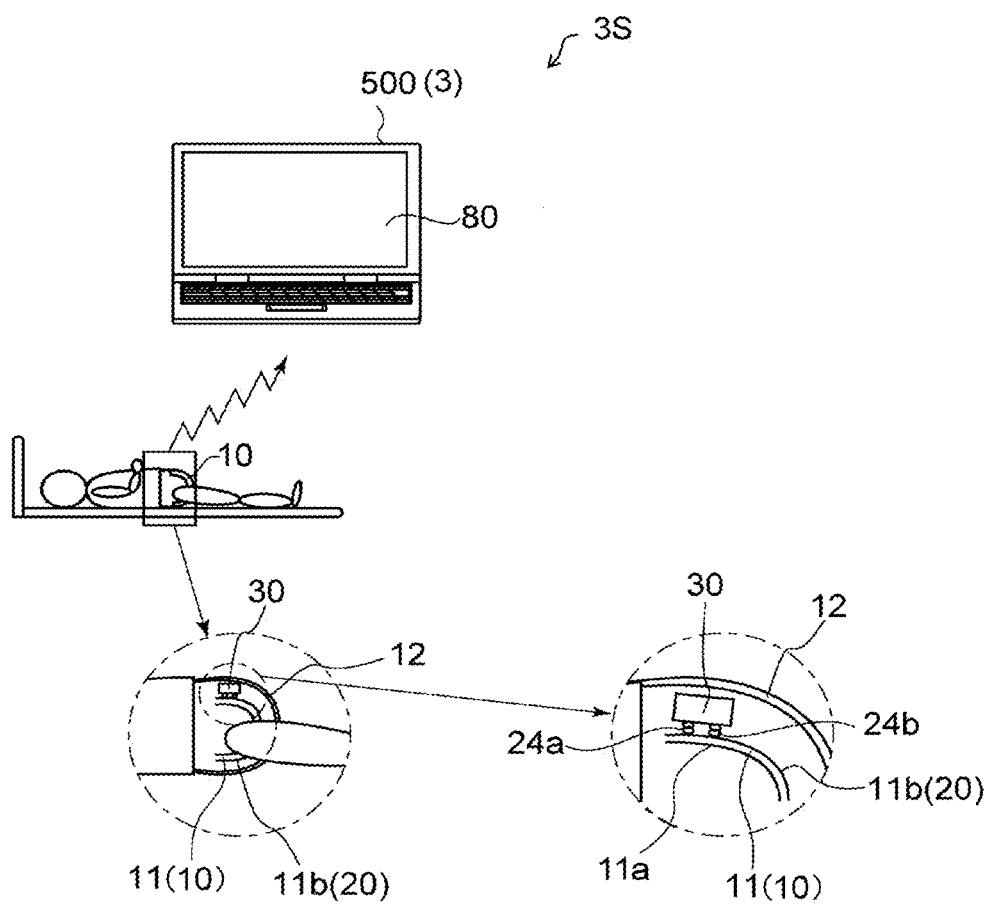
FIG. 17 is a schematic diagram illustrating an absorbent article proposal system according to a preferred third embodiment of the present invention.
Figure 18:
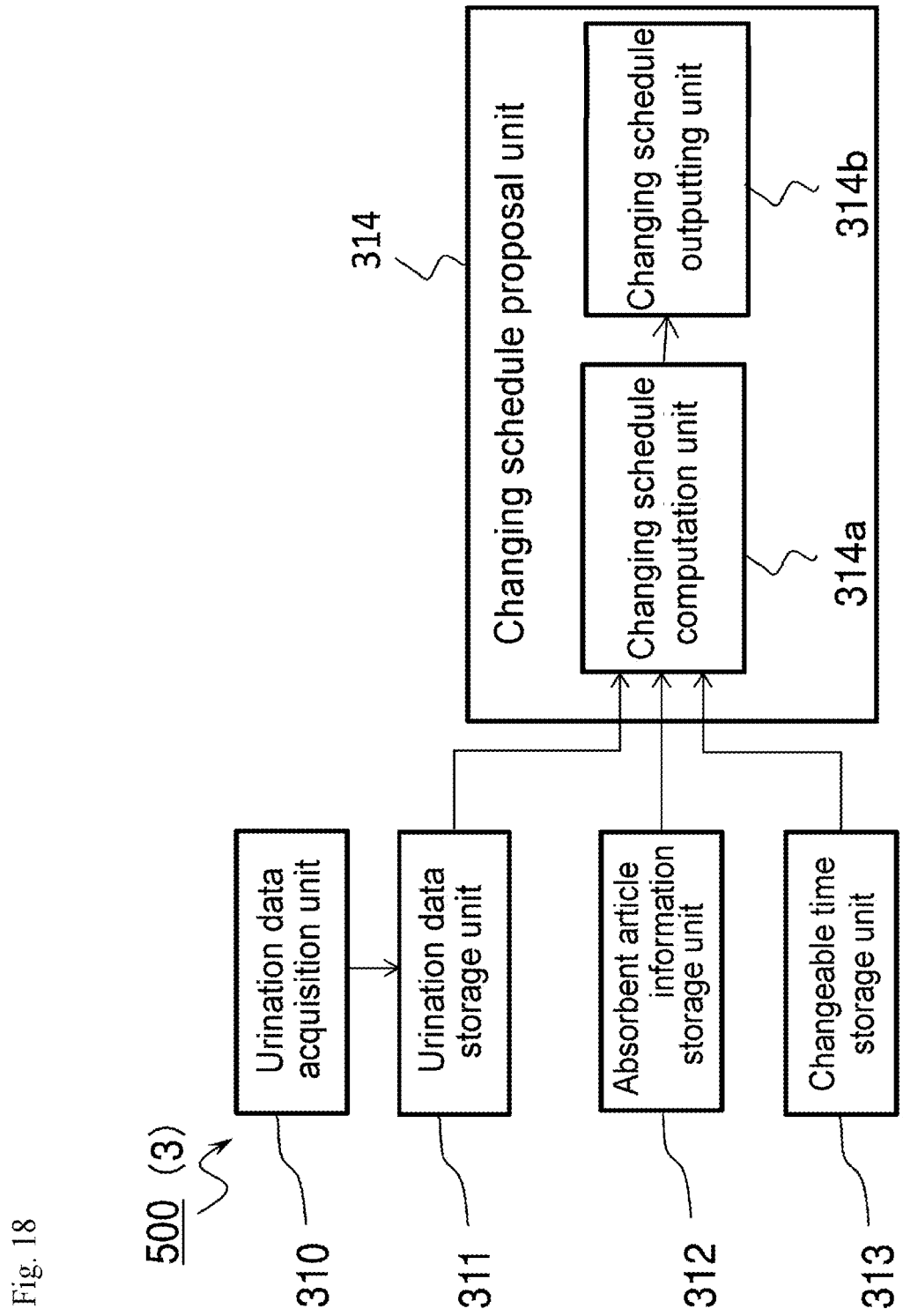
FIG. 18 is a block diagram illustrating an extended care schedule proposal device.

A care schedule proposal device 3 according to a third embodiment of the present invention is described below with reference to FIGS. 14 to 18. In the present third embodiment, the care schedule proposal device 3 illustrated in FIG. 16 may constitute a care schedule proposal system 3S by adding a urination sensor 20 and a urination data acquisition unit 310, as illustrated in FIGS. 17 and 18.

In the present third embodiment, the care schedule proposal device 3 preferably constitutes a portion of a care method proposal device, or a care method teaching device, for ordinary households.

In the present third embodiment, the care schedule proposal device 3 may employ a selected one or a plurality of types of absorbent articles as the absorbent article(s) discretionarily set by a caregiver in an ordinary household, who is the user. A changing schedule computation unit 314a can: employ, as a data collection start time and a data collection end time, time instants included in a changeable time period stored in a changeable time storage unit 313; calculate, from the urination data at one or a plurality of urination time instants, the total urination amount within each of the plurality of predetermined time periods from the data collection start time to the data collection end time which have been set; compare each calculated total urination amount with the urine absorption capacity of the absorbent article set by the user; and perform computation so as to specify a plurality of predetermined time periods such that the urine absorption capacity of the absorbent article that has been set does not fall below each calculated total urination amount. A changing schedule outputting unit 314b can present a daily absorbent-article changing schedule, together with the types of specified absorbent articles, by employing, as guides for the absorbent-article changing timings, the data collection start time or the data collection end time for each of the plurality of predetermined time periods, which has been specified in the changing schedule computation unit 314a.

In the care schedule proposal device 3 of the present third embodiment, the changeable time is designated as a time period, and not time instants. This operation is described below by using FIGS. 14(a) and 14(b).

When care is given in an ordinary household, there are only one or few caregivers, in contrast to care in a facility. Further, often, the caregiver performs other household chores, such as daily shopping. Thus, there are time periods in which the caregiver accompanies the care-receiver and mainly focuses on caregiving while doing other tasks, and time periods in which the caregiver does other tasks away from the care-receiver or accompanies the care-receiver to a hospital etc. and thus cannot change absorbent articles at all.

In view of such circumstances, the present third embodiment adopts an algorithm for proposing a care schedule wherein time periods where the caregiver does not go out but accompanies the care-receiver are set as changeable times.

In the present third embodiment, the care schedule proposal device 3 employs only one type of absorbent article and also an inner pad that can be used, considering that the device is intended for an ordinary household. This gives consideration to the fact that, in an ordinary household, it is difficult to prepare many types of absorbent articles from the viewpoint of cost and storage space, in contrast to nursing-care facilities.

On the other hand, the care schedule proposal device also has a function of presenting a schedule plan for changing articles with different capacities to aid the selection of what kind of size of absorbent article should be purchased. In this way, if the caregiver or an operator of the device determines that there is an article that is more suitable than the size that is currently being used, then it is possible to promote the purchase of the suitable article. It goes without saying that, by using a clear judgment criterion such as cost, it is possible to present only a schedule plan and the most appropriate article.

The care schedule proposal device 3 of the present third embodiment presents a changing schedule plan according to the flow illustrated in FIGS. 14(a) and 14(b). The care schedule proposal device 3 of the present third embodiment first executes pre-processing S300. As illustrated in FIG. 14(b), executed in the pre-processing S300 are: a urination data acquisition step S301 of storing, in a urination data storage unit 311 (see FIG. 18) within the device, urination data transmitted from outside or stored in a data storage region within the device; and a changeable time setting step S303 of storing, in a changeable time storage unit 313 (see FIG. 18), changeable times inputted by a caregiver or a device user.

Herein, for the urination data, it is possible to use data measured at, for example, a nursing-care facility where a care-receiver can stay for more than one night. In that case, the data can be acquired from the facility through a communication channel such as the Internet, or can be acquired through a storage medium such as a USB memory. In this way, it becomes unnecessary to use a sensor-equipped wearable article in an ordinary household, thus being able to reduce errors in urination data due to how the article is worn. Note that the urination amount measurement in a facility may be done by using a urination sensor or by weight measurement.

Further, to eliminate the inconvenience of inputting data every time, it is preferable that the changeable time setting step S303 is configured so that a plan based on past data, such as a changeable time used for a recent computation, is displayed, and the caregiver or user can change the plan as necessary.

When the pre-processing is completed, as illustrated in FIG. 14(a), in an article consideration/non-consideration selection step S106, a selection regarding whether or not to consider the absorption capacities of absorbent articles upon creating a schedule plan is inputted. Whether or not to perform consideration is selected by a caregiver or user, and is inputted to the device by a known method.

If it is inputted, in the selection step S106, that consideration is not to be made, then the operator reads, for example, a barcode on a packaging bag of the absorbent article with a camera (not illustrated) accompanying the device, and based on the information that has been read, an article-type inputting step S107 is executed. In the article-type inputting step S107, the maximum absorption capacity of the absorbent article for which the barcode has been read is acquired through the Internet, and is stored in an absorbent article information table by an absorbent article information storage unit 312. Then, a changing schedule is computed in a schedule computation step S110, and the changing schedule that has been found is displayed in a changing schedule outputting step S113 as a changing schedule plan.

The article-type inputting step S107 is a step for acquiring the maximum absorption capacity of an absorbent article. Instead of reading a barcode, the maximum absorption capacity may be acquired through other methods, such as by entering the product name or having the caregiver or user directly enter the value of the maximum absorption capacity.

If, in the selection step S106, it is selected that consideration is to be made, then an article-type initialization step S109 is executed. In the article-type initialization step S109, information on currently-available absorbent articles is acquired through the Internet etc. and stored by the absorbent article information storage unit 312. It is preferable that this information includes not only absorption capacity, but also such information as purchasing methods, to facilitate purchase after the care schedule plan is displayed.

Based on the information on absorbent articles as acquired in the article-type initialization step S109, the schedule computation step S110 is executed. The schedule computation step S110 is repeated until the article-type initialization step S109 is completed—i.e., is repeated for all absorbent articles for which information can be acquired by the step S109. When the schedule computation step S110 is completed, the procedure proceeds to the changing schedule outputting step S113, and schedule plans corresponding to the plurality of types of absorbent articles are displayed on a display unit.

Figure 15:
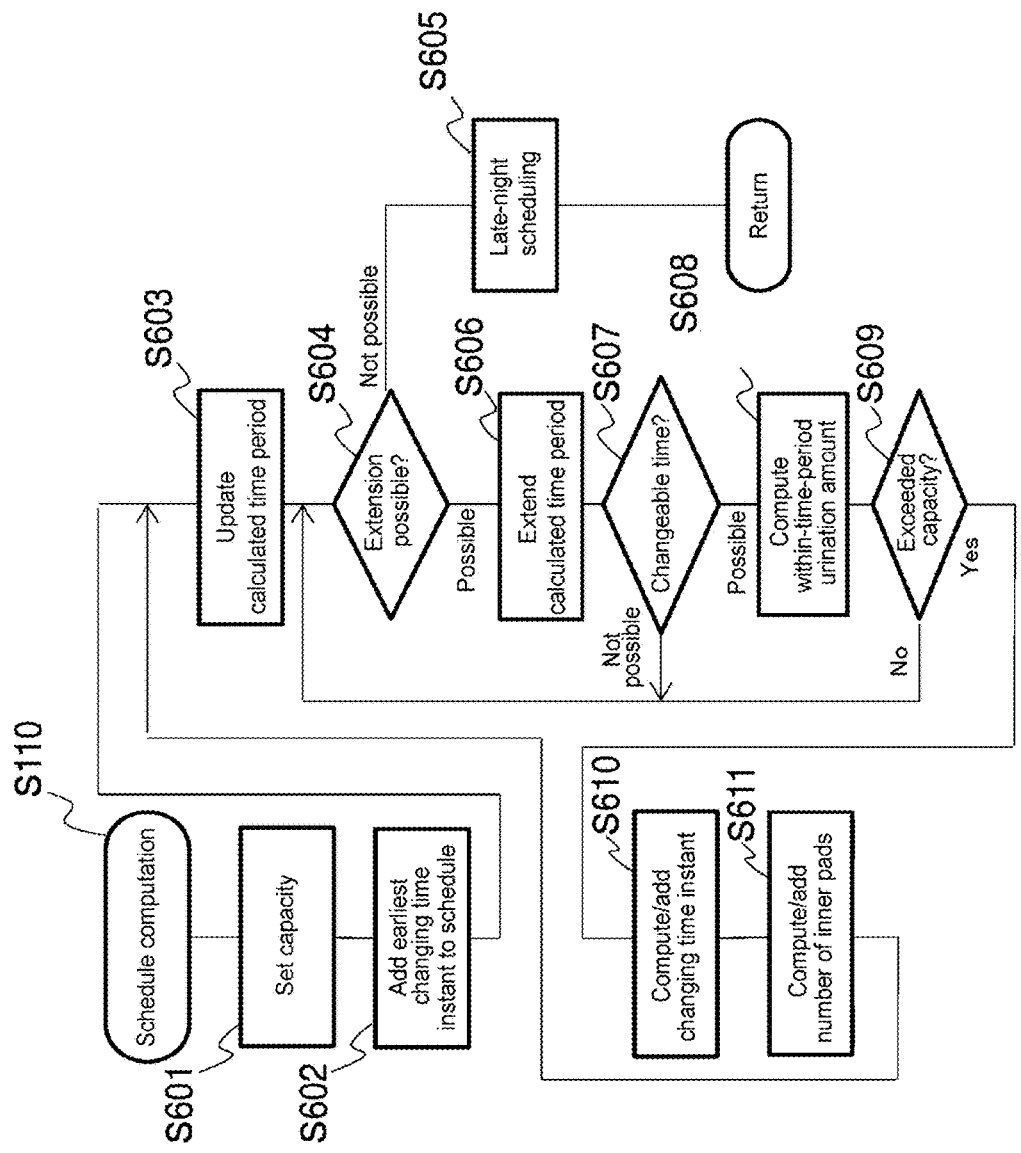
FIG. 15 is a flowchart describing an operation procedure of a schedule computation step in FIG. 14(a).
Figure 16:
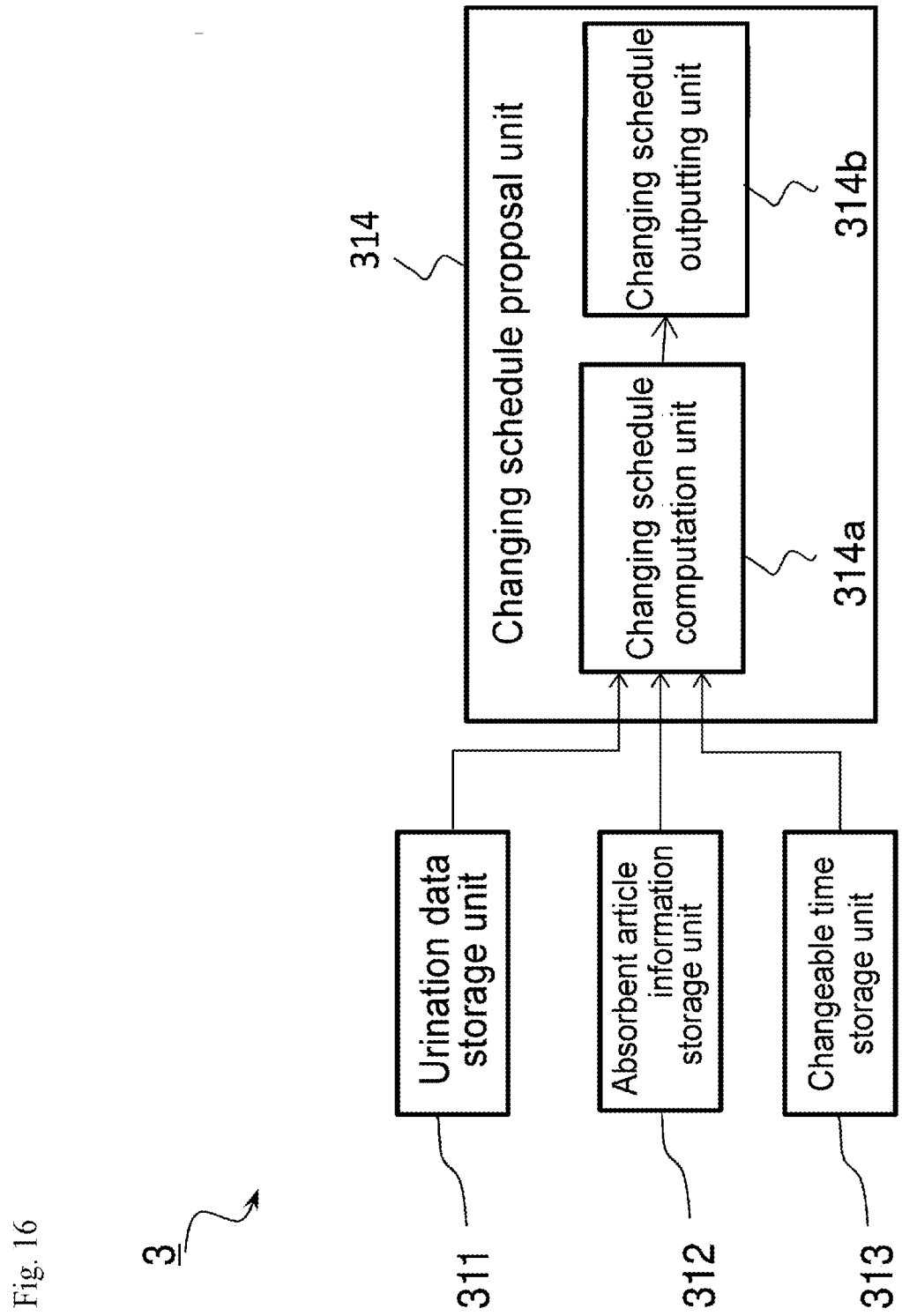
FIG. 16 is a block diagram illustrating a care schedule proposal device constituting an absorbent article proposal system according to a third embodiment.

Next, the operation procedure of the aforementioned schedule computation step S110 is described by employing FIG. 15. Note that the operations in the schedule computation step S110 are the same, regardless of whether or not to consider the absorption capacities of absorbent articles as selected in the article consideration/non-consideration selection step S106.

In the schedule computation step S110, first, in a urine-absorption-capacity setting step S601, the urine absorption capacities of the absorbent articles are set. In the present third embodiment, the urine absorption capacities are transferred by so-called argument passing from an upper-level routine, but the method is not limited thereto.

Next, in a first-changing-time-instant determination step S602, based on the urination schedule table 75 (see FIG. 7), the earliest changeable time is recorded in a candidate schedule as the initial changing time instant (first changing time instant) of the day. For example, in cases where the changeable time storage unit 313 (see FIG. 18) stores "6:00 to 9:00", "13:00 to 15:00" and "19:00 to 23:00" as changeable time periods, the earliest changeable time is "6:00", and thus, "6:00" is recorded in the schedule plan as the first changing time instant of the day.

Next, in a calculated-time-period updating step S603, the predetermined time period for calculating the total urination amount is initialized. More specifically, the most recently-recorded changing time instant is set to both the first and last time instants of the predetermined time period. Hereinbelow, the first time instant is described as "margin time 1" and the last time instant is described as "margin time 2".

Next, a calculated-time-period extendibility determination step S604 for determining whether or not the calculated time period can be extended is executed. In the calculated-time-period extendibility determination step S604, an "alteration value" is added to the "margin time 2", and the sum value is compared with the earliest time instant and the latest time instant of a designated time period stored in the changeable time storage unit. If the aforementioned sum value is not a value between the earliest time instant and the latest time instant—i.e., if the sum value is earlier than the earliest time instant of the designated time stored in the changeable time storage unit or later than the latest time instant—then it is determined that it is not possible to further extend the calculated time period, and the control proceeds to a late-night scheduling step S605. Herein, the "alteration value" is the smallest unit time in scheduling, and takes a positive value. More specifically, the alteration value is set in advance to a time from around 10 to 30 minutes.

In the calculated-time-period extendibility determination step S604, if it is determined that the calculated time period can be extended, then, in a calculated-time-period extension step S606, the sum value of the "margin time 2" and the "alteration value" is set as a new "margin time 2", and thereby the calculated time period is extended. Stated differently, the "margin time 2" among the two time instants defining the predetermined time is gradually delayed, to thereby widen the calculated time period, which is the range of the predetermined time.

Next, in a changeable time determination step S607, it is determined, by referring to data in the changeable time storage unit, whether the "margin time 2"—i.e., the end of the predetermined time—falls within a changeable time period. If it is not a changeable time, then extension is repeated until it falls within a changeable time.

When the "margin time 2", which is the latter terminal of the predetermined time, falls within a changeable time, a within-time-period urination-amount computation step S608 for calculating urination amounts within the predetermined time is executed, wherein the total urination amount within the predetermined time period defined between the "margin time 1" and the "margin time 2" is computed by using the urination data. More specifically, the within-time-period urination-amount computation step S608 constitutes the total urination amount computation step of: temporarily determining a wearing-start time instant (margin time 1), which is one changing time instant, and a wearing-end time instant (margin time 2), which is the next changing time instant, from the changeable time instants or the changeable time periods stored in the changeable time storage unit 313 of the care schedule proposal device 3; and finding, from the urination data stored in the urination data storage unit 311, the total urination amount within the predetermined time period defined by the temporarily determined one changing time instant and next changing time instant. In the present third embodiment, the within-time-period urination-amount computation step S608, which is the total urination amount computation step, is executed in the schedule computation step S110.

Next, in a maximum-absorption-capacity exceedance determination step S609, it is determined whether or not the total urination amount has exceeded the capacity of the absorbent article having the largest capacity; if the total urination amount has not exceeded the capacity, the procedure returns to the calculated-time-period extendibility determination step S604. More specifically, until it is determined that the range of the predetermined time has exceeded the range of the changeable time in the calculated-time-period extendibility determination step S604 or it is determined that the capacity of all of the absorbent members has been exceeded, the span of the predetermined time for calculating the total urination amount is widened gradually—more specifically, in increments of the time of the alteration value—toward the delaying side. In this way, a time instant is determined at which the limit of the absorbent article capacity is exceeded within the range of the changeable time.

When a time period in which the limit of the absorbent article capacity is exceeded is found, then, a changing-time-instant computation/addition step S610 for finding a changing time instant to be added to the schedule and adding it to the schedule is executed. More specifically, a changing time instant to be added is found according to the following procedure.

That is, the time instant found by subtracting the "alteration value" from the "margin time 2" at which the maximum capacity is exceeded is found as a "changing time instant candidate" to be newly added to the schedule. If the "changing time instant candidate" is included in a changeable time, the "changing time instant candidate" is added to the schedule as a changing time instant. If it is not included, then the "margin time 2" before subtraction is added to the schedule as a changing time instant.

Thus, in the present third embodiment, the schedule computation step S110: compares the total urination amount that has been found and the urine absorption capacity of the absorbent article; and finds at least either the predetermined time period or the absorbent article by which the urine absorption capacity does not fall below the total urination amount. Further, preferably, in the schedule computation step S110, the changing time instant for changing the absorbent article is found and proposed by altering either the one changing time instant (margin time 1) or the next changing time instant (margin time 2), to thereby search for the predetermined time period in which the urine absorption capacity of the absorbent article does not fall below the total urination amount.

Next, an inner-number computation/addition step S611 is executed.

In the inner-number computation/addition step S611, first, a period between the added changing time instant and an immediately-preceding changing time instant is employed as the predetermined time, and the total urination amount therefor is computed from the urination data. Then, the capacity of the absorbent article is subtracted from the total urination amount that has been found.

If the difference found by subtraction is negative—i.e., if the capacity of the absorbent article is greater than the total urination amount that has been found—then the number of inner pads is set to zero. If the difference found by subtraction is zero—i.e., if the capacity of the absorbent article is equal to the total urination amount that has been found—then the number of inner pads is set to one. This is because, when providing at-home care, it is preferable to reduce the risk of leakage. If the difference found by subtraction is positive—i.e., if the capacity of the absorbent article is smaller than the total urination amount that has been found—then the difference found by subtraction is divided by the capacity of the inner pad, and the rounded-up quotient is found as the number of inner pads.

The number of inner pads that has been found is added to the schedule plan as the number of inner pads recommended at the immediately-preceding changing time instant.

When the process of the inner-number computation/addition step S611 is completed, the procedure returns to calculated-time-period updating step S603 to find the next changing time instant.

By repeating the steps from the calculated-time-period updating step S603 to the inner-number computation/addition step S611, changing time instants and numbers of inner pads to be used are added sequentially to the schedule plan. When the terminal of the predetermined time goes beyond the last changeable time, the control proceeds to the late-night scheduling step S605, to schedule the last changing task of the day.

In the late-night scheduling step S605, first, the last changing time instant of the day is determined.

The total urination amount of a predetermined time period between the changing time instant which is the last time instant among those added to the schedule and the last time instant included in the changeable time is found by using the urination data. If the total urination amount that has been found is not zero, then the last time instant included in the changeable time is added to the schedule as the last changing time instant of the day, and also, the number of inner pads at the changing time instant immediately prior to the last changing time instant is set to zero and added to the schedule.

If the total urination amount is zero—i.e., if there is no urination data between the last changing time instant within the schedule and the last designated time instant—then the last changing time instant within the schedule becomes the last changing time instant of the day, and thus there is no need to add a changing time instant to the schedule.

Then, the number of inner pads at the last changing time instant of the day is determined according to the following procedure, and the determined number of inner pads is added to the schedule.

First, a nighttime total urination amount, which is the total urination amount during the nighttime—i.e., the period from the last changing time instant of the day to the first changing time instant of the next day—is computed by using the urination data.

Next, the capacity of the absorbent article is subtracted from the nighttime total urination amount that has been found.

If the difference found by subtraction is negative—i.e., if the capacity of the absorbent article is greater than the nighttime total urination amount that has been found—then the number of inner pads is set to one. Also, if the difference found by subtraction is zero—i.e., if the capacity of the absorbent article is equal to the total urination amount that has been found—then the number of inner pads is set to one. This is because, when providing at-home care, it is preferable to reduce the risk of leakage. If the difference found by subtraction is positive—i.e., if the capacity of the absorbent article is smaller than the total urination amount that has been found—then the difference found by subtraction is divided by the capacity of the inner pad, and the rounded-up quotient is found as the necessary number of inner pads.

The number of inner pads that has been found is added to the schedule plan as the number of inner pads recommended at the last changing time instant of the day, as described above.

An example (output example) of a result of computing absorbent-article changing schedule candidates found according to the aforementioned procedure is shown in Table 4. In this example, the changing time instants and the numbers of times of changes are shown simultaneously for when using an S-size article and when using an M-size article.

In addition to the number of times of changes, the outputted schedule candidate may be configured to show a value indicating the result of calculating the total capacity of absorbent articles to be used in each schedule candidate. Alternatively, it is possible to show only the schedule candidate in which the total capacity of absorbent articles to be used is smaller as a result of comparison.

TABLE 4

| | | Use S-size | | | | | | | | | | | |
|---|---|---|---|---|---|---|---|---|---|---|---|---|---|
| | Changing time instant | 5:30 | 8:40 | 9:55 | 11:30 | 12:40 | 13:55 | 14:20 | 15:40 | 16:55 | 17:55 | 19:20 | 22:40 |
| Change 12 times | Number of inner pads | 0 | 0 | 1 | 0 | 1 | 1 | 0 | 1 | 0 | 1 | 1 | 4 |
| | | Use M-size | | | | | | | | | | | |
| | Changing time instant | 5:30 | 8:40 | 9:55 | 11:30 | 12:40 | 13:55 | | 15:40 | | 17:55 | 19:20 | 22:40 |
| Change 10 times | Number of inner pads | 0 | 0 | 0 | 0 | 0 | 0 | | 0 | | 0 | 0 | 3 |

Further, items related to wearer information and life information can be inputted to the care schedule proposal device 3 of the present third embodiment whenever necessary at any of the timings in the aforementioned steps.

The care schedule proposal device 3 of the present third embodiment can output, on a display unit, information on absorbent articles outputted from the changing schedule outputting unit 314b, and also (although not illustrated): urination time instants accumulated in the urination-time-instant accumulation table 72 (see FIG. 7) of the database; urine absorption amounts accumulated in the urine-absorption-amount accumulation table 73 (see FIG. 7); total urination amounts accumulated in the urination schedule table 75 (see FIG. 7); wearer information accumulated in the wearer information table 78 (see FIG. 7); and life information accumulated in the life information table 77 (see FIG. 7). It is preferable that, in this way, the information on absorbent articles outputted from the changing schedule outputting unit 314b is outputted together with information such as urination time instants, urine absorption amounts, total urination amounts, wearer information, and life information.

Next, an absorbent article proposal system 3S, which is an expansion of the care schedule proposal device 3 of the present third embodiment, will be described. In the present third embodiment, the absorbent article proposal system 3S (see FIG. 17), which is an expansion of the care schedule proposal device 3, includes an absorbent-article selection/information-provision device 500 (care schedule proposal device 3) that: acquires, via a data collection unit 30, an amount of change-over-time in impedance, which is measured by a urination sensor 20 attached to an absorbent article for absorbing urine and which is caused by the spreading of urine in the absorbent article, or computed data based thereon; and selects and proposes an absorbent article on the basis of the acquired data. The absorbent article proposal system 3S is constructed by adding, for example, a urination sensor 20 to the care schedule proposal device 3, and constituent members similar to those of the aforementioned care schedule proposal device 3 are accompanied by the same reference signs, and explanation thereon is omitted. Further, unless specifically explained otherwise, the urination sensor 20 and the data collection unit 30 are the same as those in the care schedule proposal system 1S of the first embodiment, and explanation given in the first embodiment is applied as appropriate.

The absorbent-article selection/information-provision device 500 is achieved by adding, to the aforementioned care schedule proposal device 3, a urination data acquisition unit 310 that: receives an amount of change-over-time in impedance measured by the urination sensor 20 or computed data based thereon, which is transmitted from the data collection unit 30; converts the data into urination data; and records the same.

More specifically, as illustrated in FIG. 18, the absorbent-article selection/information-provision device 500 includes, for example: a urination data acquisition unit 310; a urination data storage unit 311; an absorbent article information storage unit 312; a changeable time storage unit 313; and a changing schedule proposal unit 314. A changing schedule computation unit 314a of the changing schedule proposal unit 314 selects an absorbent article having an absorption capacity greater than the total urination amount, which is the total of urine absorption amounts within a predetermined time period as calculated from the change-over-time in impedance. A changing schedule outputting unit 314b outputs the information on the absorbent article by displaying it on a screen (display unit) 80 together with a proposed changing time instant.

In the absorbent article proposal system 3S (see FIG. 17) of the present third embodiment, data from a urination information acquisition device (data collection unit) 30 is transmitted to the absorbent-article selection/information-provision device 500 via a communication channel. The communication channel may be a wired channel or a wireless channel.

At home, the mealtime and activity status of a care-receiver are different from those when he/she is in a facility. Thus, the amount and time of urination may greatly differ from those when the care-receiver is staying in a facility. In such cases, scheduling based on urination data collected in a facility may be problematic, as it may lead to leakage of urine from an absorbent article. In the absorbent article proposal system 3S of the present third embodiment, urination data acquired at home can be used, and thus, it is possible to select appropriate absorbent articles and changing time instants.

Further, even in cases where leakage of urine does not become a problem, by collecting urination data by using the urination sensor 20, it is possible to further improve QOL by selecting more appropriate absorbent articles and changing time instants in accordance with urination time and changes in urination amount.

In the present third embodiment, the absorbent-article selection/information-provision device 500 can be formed by using a notebook-sized PC, but it may be formed by using a general-purpose computer, such as a personal computer, e.g. desktop PC, laptop PC, netbook PC, handheld PC or tablet PC, a server machine, or a mobile terminal (smartphone, etc.).

In the present third embodiment, the changing schedule outputting unit 314b may output, to the display unit 80 of the absorbent-article selection/information-provision device 500, information related absorbent articles included in the proposed changing schedule, such as prices and purchasing methods, in addition to the computed changing schedule.

Further, other than the absorbent article information, it is preferable that the changing schedule outputting unit 314b outputs information stored in a life information table or a wearer information table, which are not illustrated. More specifically, it is preferable to provide a database that stores information similar to information stored in the urination schedule table 75, the life information table 77, or the wearer information table 78 in the care schedule proposal device 1 of the first embodiment, and allow the stored information to be outputted on the display unit 80.

In the present third embodiment, the absorbent article proposal system 3S may include a function with which it is possible to order and purchase, via the Internet etc., the absorbent article selected by the absorbent-article selection/information-provision device 500 based on data on the aforementioned urination pattern. For example, an order information inputting screen for ordering the absorbent article included in the proposed changing schedule may be displayed on the display unit 80 at the timing that the changing schedule outputting unit 314b outputs the absorbent article information onto the display unit 80 of the absorbent-article selection/information-provision device 500, so that the absorbent article can be ordered. The absorbent-article selection/information-provision device 500 may access a webpage creating the order information inputting screen, to make the display unit 80 display the webpage. An orderer can input order information through the order information inputting screen, and place an order for the absorbent article. Examples of order information include the address, name, age, gender, phone number, and email address of the orderer, the date of order, the product and the number thereof, and destination. Note that the timing for outputting the order information inputting screen for ordering the selected absorbent article may be a discretionary timing other than the timing of outputting the absorbent article information.

In the present third embodiment, it is preferable that the absorbent-article selection/information-provision device 500 of the absorbent article proposal system 3S is configured so as to include a function of determining the maximum value among total urination amounts within a certain predetermined time period across a plurality of days, like the maximum-urine-absorption-amount acquisition unit 524 of the first embodiment, and selecting an absorbent article having a greater absorption capacity than the maximum value among total urination amounts within the predetermined time period across a plurality of days.

In relation to the various embodiments of the present invention described above, the invention further discloses the following care schedule proposal devices, care schedule proposal systems, and care schedule proposal methods.

{1} A care schedule proposal device comprising:
a urination data storage unit that stores, together with urination time instant data, urination amount data of a wearer as acquired from a urine absorption amount of an absorbent article that absorbs urine;
an absorbent article information storage unit that stores article information including a urine absorption capacity of the absorbent article;
a changeable time storage unit that stores a changeable time instant or a changeable time period that can serve as a candidate for a changing time instant for changing the absorbent article; and
a changing schedule proposal unit that proposes a changing schedule for changing the absorbent article, wherein:
the changing schedule proposal unit includes a changing schedule computation unit and a changing schedule outputting unit;
the changing schedule computation unit finds, on the basis of the urination amount data and the urination time instant data stored in the urination data storage unit, a total urination amount within a predetermined time period defined by a wearing-start candidate time instant and a wearing-end candidate time instant which are selected from the changeable time instant or the changeable time period stored in the changeable time storage unit;
the changing schedule computation unit performs, by comparing the total urination amount that has been found and the urine absorption capacity of the absorbent article stored in the absorbent article information storage unit, computation for finding at least either the absorbent article or the predetermined time period in a manner that the urine absorption capacity of the absorbent article does not fall below the total urination amount; and
the changing schedule outputting unit presents schedule information including at least either the absorbent article or the predetermined time period found by the changing schedule computation unit.

{2} The care schedule proposal device as set forth in clause {1}, wherein:
the absorbent article information storage unit stores article information including respective urine absorption capacities for a plurality of types of the absorbent articles; and
the changing schedule outputting unit presents, together with at least a wearing-start time, the absorbent article selected from the plurality of types of the absorbent articles.

{3} The care schedule proposal device as set forth in clause {2}, wherein:
the changeable time storage unit stores a plurality of the changeable time instants that can serve as candidates for changing time instants for changing the absorbent article; and
the changing schedule computation unit performs computation for finding a total urination amount for each of a plurality of the predetermined time periods each being defined by the plurality of changeable time instants that are stored, and selecting, from the plurality of types of the absorbent articles, the absorbent article to be used in each of the plurality of predetermined time periods.

{4} The care schedule proposal device as set forth in clause {1} or {2}, wherein the changing schedule computation unit performs computation for finding the predetermined time period in which the urine absorption capacity of the absorbent article does not fall below the total urination amount, by altering the wearing-start candidate time instant or the wearing-end candidate time instant while referring to the changeable time storage unit.

{5} The care schedule proposal device as set forth in any one of clauses {1} to {4}, wherein:
the changing schedule computation unit performs schedule computation for finding at least either the absorbent article or the predetermined time period for at least 24 hours;
and the changing schedule outputting unit presents a 24-hour changing schedule for changing the absorbent article.

{6} The care schedule proposal device as set forth in any one of clauses {2} to {5}, wherein:
the care schedule proposal device includes an absorbent article limitation means that limits absorbent articles to be used for computation; and
the changing schedule computation unit performs computation for determining the predetermined time period by using the urine absorption capacity of the absorbent articles having been limited by the absorbent article limitation means.

{7} The care schedule proposal device as set forth in any one of clauses {1} to {6}, wherein:
the urination data storage unit stores a plurality of days' worth of the wearer's urination amount data; and
the changing schedule computation unit performs computation for determining at least either the absorbent article or the predetermined time period by employing a maximum total urination amount, among respective total urination amounts found over the plurality of days within the predetermined time period having been set, as the total urination amount within that predetermined time period.

{8} A care schedule proposal system comprising:
the care schedule proposal device as set forth in any one of clauses {1} to {7};
a urination sensor that measures spreading of urine by employing impedance; and
a data acquisition unit that acquires data from the urination sensor.

{9} A care schedule proposal method for proposing at least either an absorbent article to be worn or a changing time instant for changing an absorbent article, by using
urination data including urination amount data and urination time instant data corresponding to the urination amount data, and urine absorption capacity data including a urine absorption capacity of an absorbent article to be used, in circumstances where there are limitations in terms of changeable time instants or changeable time periods that can serve as the changing time instant for changing the absorbent article, the care schedule proposal method comprising:

a total urination amount computation step of temporarily determining a wearing-start time instant, which is one changing time instant, and a wearing-end time instant, which is a next changing time instant, from the changeable time instants or the changeable time periods, and finding, from the urination data, a total urination amount in a predetermined time period defined by the temporarily determined one changing time instant and next changing time instant; and a schedule computation step of comparing the total urination amount that has been found and the urine absorption capacity of the absorbent article, and finding at least either the predetermined time period or the absorbent article by which the urine absorption capacity does not fall below the total urination amount.

{10} The care schedule proposal method as set forth in clause {9}, wherein:

in the schedule computation step, for the absorbent article whose urine absorption capacity is to be compared with the total urination amount that has been found, searching is started from an absorbent article having the smallest urine absorption capacity, from among a plurality of types of the absorbent articles;

in cases where the total urination amount is greater than the urine absorption capacity, the absorbent article is repeatedly altered until the total urination amount becomes smaller than the urine absorption capacity; and in cases where the total urination amount is smaller than the urine absorption capacity, the wearing-start time instant defining the predetermined time period and the absorbent article are proposed as the changing time instant and the absorbent article to be used for changing.

{11} The care schedule proposal method as set forth in clause {9}, wherein, in the schedule computation step, the changing time instant for changing the absorbent article is found and proposed by altering either the one changing time instant or the next changing time instant and thereby searching for the predetermined time period in which the urine absorption capacity of the absorbent article does not fall below the total urination amount.

{12} The care schedule proposal method as set forth in clause {11}, wherein the schedule computation step involves:

a total urination amount computation step of finding a total urination amount in a predetermined time period defined by one candidate changing time instant and a next candidate changing time instant;

an amount comparison step of comparing the total urination amount found in the total urination amount computation step and an absorption capacity of an absorbent article to be used in the predetermined time period;

a predetermined time period increasing step wherein, in cases where the total urination amount is below the capacity of the absorbent article in the amount comparison step, the next candidate changing time instant is repeatedly increased by a given amount until it is included in the changeable time instant or the changeable time period; and a step wherein, in cases where the total urination amount exceeds the capacity of the absorbent article in the amount comparison step, the next candidate changing time instant is returned to the immediately-preceding value and the predetermined time period is determined.

{13} The care schedule proposal method as set forth in clause {11}, wherein the schedule computation step involves:

a total urination amount computation step of finding a total urination amount in a predetermined time period defined by one candidate changing time instant and a next candidate changing time instant;

an amount comparison step of comparing the total urination amount found in the total urination amount computation step and an absorption capacity of an absorbent article to be used in the predetermined time period;

a predetermined time period increasing step wherein, in cases where the total urination amount is below the capacity of the absorbent article in the amount comparison step, the one candidate changing time instant is repeatedly decreased by a given amount until it is included in the changeable time instant or the changeable time period; and a step wherein, in cases where the total urination amount exceeds the capacity of the absorbent article in the amount comparison step, the one candidate changing time instant is returned to the immediately-preceding value and the predetermined time period is determined.

{14} The care schedule proposal method as set forth in any one of clauses {9} to {13}, wherein:

the care schedule proposal method uses at least 24 hours' worth of the urination data including the urination amount data and the urination time instant data corresponding to the urination amount data; and the schedule computation step performs schedule computation for finding at least either the absorbent article or the predetermined time period for at least 24 hours. the schedule computation step performs schedule computation for finding at least either the absorbent article or the predetermined time period for at least 24 hours.

{15} The care schedule proposal method as set forth in clause {14}, further comprising:

a nighttime total urination amount computation step of finding a nighttime total urination amount which is the total urination amount between the last changing time instant of a day and the first changing time instant of a day; and a nighttime absorbent article selection step of selecting an absorbent article and computing the necessary number of auxiliary absorbent articles by using the nighttime total urination amount.

INDUSTRIAL APPLICABILITY

According to the care schedule proposal device, the care schedule proposal method, or the care schedule proposal system of the present invention, it is possible to efficiently employ an absorbent article that has an absorption capacity sufficient for absorbing the urination amount until the next changing time and has an absorption capacity not excessively exceeding the urination amount, and that has a moderate absorbency corresponding to the urination amount until the next changing time. Further, according to the care schedule proposal device, the care schedule proposal method, or the care schedule proposal system of the present invention, it is possible to propose an appropriate daily changing schedule that employs an absorbent article having an appropriate absorbency and that contributes to reduction in the burden on the caregiver and improvement in the QOL of the care-receiver in accordance with the situations and circumstances surrounding the care-receiver, who is the wearer.

The invention claimed is:

1. A care schedule proposal device comprising:
a urination data storage unit that stores, together with urination time instant data, urination amount data of a wearer as acquired from a urine absorption amount of an absorbent article that absorbs urine;
an absorbent article information storage unit that stores article information including a urine absorption capacity of the absorbent article;
a changeable time storage unit that stores a changeable time instant or a changeable time period that serve as a candidate for a changing time instant for changing the absorbent article; and
a changing schedule proposal unit that proposes a changing schedule for changing a proposed absorbent article to be worn by the wearer, wherein:
the changing schedule proposal unit includes a changing schedule computation unit and a changing schedule outputting unit;
the changing schedule computation unit finds, on the basis of the urination amount data and the urination time instant data stored in the urination data storage unit, a total urination amount within a proposed predetermined time period for wearing the proposed absorbent article defined by a wearing-start candidate time instant and a wearing-end candidate time instant which are selected from the changeable time instant or the changeable time period stored in the changeable time storage unit;
the changing schedule computation unit performs, by comparing the total urination amount that has been found and the urine absorption capacity of the proposed absorbent article stored in the absorbent article information storage unit, computation for finding the proposed absorbent article and the proposed predetermined time period in a manner that the urine absorption capacity of the proposed absorbent article does not fall below the total urination amount; and
the changing schedule outputting unit presents schedule information for a future point in time including the proposed absorbent article and the proposed predetermined time period found by the changing schedule computation unit.

2. The care schedule proposal device according to claim 1, wherein:
the absorbent article information storage unit stores article information including respective urine absorption capacities for a plurality of types of absorbent articles; and
the changing schedule outputting unit presents, together with at least a proposed wearing-start time, the proposed absorbent article selected from the plurality of types of the absorbent articles.

3. The care schedule proposal device according to claim 2, wherein:
the changeable time storage unit stores a plurality of changeable time instants that serve as candidates for changing time instants for changing the proposed absorbent article; and
the changing schedule computation unit performs computation for finding a total urination amount for each of a plurality of proposed predetermined time periods each being defined by the plurality of changeable time instants that are stored, and selecting, from the plurality of types of the absorbent articles, the proposed absorbent article to be used in each of the plurality of the proposed predetermined time periods.

4. The care schedule proposal device according to claim 1, wherein the changing schedule computation unit performs the computation for finding the proposed predetermined time period in which the urine absorption capacity of the proposed absorbent article does not fall below the total urination amount, by altering the wearing-start candidate time instant or the wearing-end candidate time instant while referring to the changeable time storage unit.

5. The care schedule proposal device according to claim 1, wherein:
the changing schedule computation unit performs schedule computation for finding the proposed absorbent article and the proposed predetermined time period for at least 24 hours; and
the changing schedule outputting unit presents a 24-hour changing schedule for changing the proposed absorbent article.

6. The care schedule proposal device according to claim 2, wherein:
the care schedule proposal device includes an absorbent article limitation means that limits absorbent articles to be used for the computation; and
the changing schedule computation unit performs the computation for determining the proposed predetermined time period by using the urine absorption capacity of the absorbent articles having been limited by the absorbent article limitation means.

7. The care schedule proposal device according to claim 1, wherein:
the urination data storage unit stores a plurality of days' worth of the wearer's urination amount data; and
the changing schedule computation unit performs the computation for determining the proposed absorbent article and the proposed predetermined time period by employing a maximum total urination amount, among respective total urination amounts found over the plurality of days within the proposed predetermined time period having been set, as the total urination amount within that proposed predetermined time period.

8. A care schedule proposal system comprising:
the care schedule proposal device according to claim 1;
a urination sensor configured to measure a spreading of urine by employing impedance; and
a data acquisition unit that acquires data from the urination sensor.

9. A care schedule proposal method for proposing a proposed absorbent article to be worn by a user and a proposed changing time instant for changing the proposed absorbent article, by using urination data including urination amount data and urination time instant data corresponding to the urination amount data, and urine absorption capacity data including a urine absorption capacity of an absorbent article to be used, in circumstances where there are limitations in terms of changeable time instants or changeable time periods that serve as the changing time instant for changing the proposed absorbent article, the care schedule proposal method comprising:
a total urination amount computation step of
temporarily determining a wearing-start time instant, which is one changing time instant, and a wearing-end time instant, which is a next changing time instant, from the changeable time instants or the changeable time periods, and finding, from the urination data, a total urination amount in a proposed predetermined time period for wearing the proposed absorbent article defined by the temporarily determined the one changing time instant and the next changing time instant;

a schedule computation step of comparing the total urination amount that has been found and the urine absorption capacity of the proposed absorbent article, finding the proposed predetermined time period and the proposed absorbent article by which the urine absorption capacity does not fall below the total urination amount; and a schedule presentation step of presenting schedule information for a future point in time including the proposed absorbent article and the proposed predetermined time period found by the schedule computation step.

10. The care schedule proposal method according to claim 9, wherein:
 in the schedule computation step, for the proposed absorbent article whose urine absorption capacity is to be compared with the total urination amount that has been found, searching is started from an absorbent article having the smallest urine absorption capacity, from among a plurality of types of absorbent articles;
 in cases where the total urination amount is greater than the urine absorption capacity, the proposed absorbent article is repeatedly altered until the total urination amount becomes smaller than the urine absorption capacity; and
 in cases where the total urination amount is smaller than the urine absorption capacity, the wearing-start time instant defining the proposed predetermined time period is proposed as the changing time instant and the proposed absorbent article is proposed as the absorbent article to be used for changing.

11. The care schedule proposal method according to claim 9, wherein, in the schedule computation step, the changing time instant for changing the proposed absorbent article is found and proposed by altering either the one changing time instant or the next changing time instant, to search for the proposed predetermined time period in which the urine absorption capacity of the proposed absorbent article does not fall below the total urination amount.

12. The care schedule proposal method according to claim 9, wherein:
 the care schedule proposal method uses at least 24 hours' worth of the urination data including the urination amount data and the urination time instant data corresponding to the urination amount data; and
 the schedule computation step performs schedule computation for finding at least either the proposed absorbent article or the proposed predetermined time period for at least 24 hours.

* * * * *